(12) United States Patent
Koops et al.

(10) Patent No.: US 6,664,444 B1
(45) Date of Patent: Dec. 16, 2003

(54) TRANSGENIC PLANTS PRESENTING A MODIFIED INULIN PRODUCING PROFILE

(75) Inventors: Andries Jurriaan Koops, Opheusden (NL); Robert Sevenier, Wageningen (NL); Arjen Johannes Van Tunen, Wageningen (NL); Lena De Leenheer, Tervuren (BE)

(73) Assignees: Tiense Suikerraffinaderij N.V. (BE); Plant Research International B.V. (NL)

( * ) Notice: Subject to any disclaimer, the term of this patent is extended or adjusted under 35 U.S.C. 154(b) by 0 days.

(21) Appl. No.: 09/673,492

(22) PCT Filed: Apr. 15, 1999

(86) PCT No.: PCT/EP99/02538

§ 371 (c)(1), (2), (4) Date: Oct. 16, 2000

(87) PCT Pub. No.: WO99/54480

PCT Pub. Date: Oct. 28, 1999

(30) Foreign Application Priority Data

Apr. 17, 1998 (EP) .............................. 98870084

(51) Int. Cl.$^7$ ........................ C12N 15/29; C12N 15/54; C12N 15/82; A01H 5/00; C12P 19/04

(52) U.S. Cl. ...................... 800/284; 800/278; 800/285; 800/289; 800/306; 800/312; 800/313; 800/317.2; 800/317.3; 800/317.4; 800/320; 800/320.1; 800/320.2; 800/320.3; 800/322; 435/69.1; 435/69.8; 435/101; 435/320.1; 435/468; 435/193; 536/23.2; 536/23.6

(58) Field of Search ............................... 536/23.6, 23.2; 435/69.1, 101, 320.1, 468, 419, 69.8, 193; 800/278, 284, 285, 289, 320, 320.1, 320.2, 320.3, 322, 306, 312, 313, 317.4, 317.3, 317.2

(56) References Cited

U.S. PATENT DOCUMENTS 6,365,800 B1 * 4/2002 Caimi ........................ 800/284

FOREIGN PATENT DOCUMENTS

| EP | 0822262 | 2/1998 | ........... C13K/11/00 |
| WO | WO 96/01849 | 1/1996 | ........... C08B/37/18 |
| WO | WO 96/01904 | 1/1996 | ........... C12N/15/82 |
| WO | WO 96/21023 | 7/1996 | ........... C12N/15/54 |
| WO | WO 97/29133 | 8/1997 | ........... C08B/37/18 |
| WO | WO 97/42331 | 11/1997 | ........... C12N/15/82 |
| WO | WO 98/05793 | 2/1998 | ........... C12P/19/14 |
| WO | WO 98/39460 | 9/1998 | ........... C12N/15/82 |
| WO | WO 99/24593 | 5/1999 | ........... C12N/15/82 |

OTHER PUBLICATIONS

Smeekens et al. Biochem. Soc. Trans. 19: 565–569, 1991.*
Turk et al. New Phytol. 136(1): 29–38, 1997.*
Van der Krol et al. Plant Cell 2: 291–299, Apr. 1990.*
Stam et al. Ann. Bot. 79: 3–12, 1997.*
Goblet et al. Accession No. U84398, Jan. 1997.*
Hall, R. et al, "A high efficiency technique for the generation of transgenic sugar beets from stomatal guard cells" Nature Biotechnology vol. 14, Sep. 1996, pps 1133–1138.
Koops et al, Purification and characterization of the enzymes of fructan biosynthesis in tubers of Helianthus tuberosus 'Columbia', Journal of Experimental Botany, vol. 45 No. 280, pp1623–1631, Nov. 1994.
Koops et al, Purification and characterization of the enzymes of fructan biosynthesis in tubers of Helianthus tuberosus Columbia, Plant Physio., (1996), pp 1167–1175, vol. 110.
De Leenheer, L., "Production and use of inulin: Industrial reality with a promising future" Carbohydrates as Organic Raw Material III, The Netherlands, Nov. 28–29, 1994, Bekkum et al, Eds, pp. 67–92.
van Engelen, F., et al, "pBINPLUS: an improved plant transformation vector based on pBIN 19", Transgenic Research 4, pps 288–290 (1995).
van der Meer, I., et al, "Cloning of the fructan biosynthesis pathway of Jerusalem artichoke" The Plant Journal, (1998), 15(4), pps 489–500.
Vijn, I., et al, "Fructan of the inulin neoseries is synthesized in trangenic chicory plants (Cichorium intybus L.) harbouring onion (Allium cepa L.) fructan: fructan 6G–fructosyltransferase" The Plant Journal, (1997) 11(3), PPS 387–398.
Visser, R., "Regeneration and transformation of potato by Agrobacterium tumefaciens" Plant Tissue Culture Manual B5, 1991, pps 1–9.
Wise, C.S. et al, "Determination of easily Hydrolyzable Fructose Units in Dextran Preparations" Analytical Chemistry, vol. 27, No. 1, Jan. 1955, pp. 33–36.

(List continued on next page.)

Primary Examiner—David T. Fox
(74) Attorney, Agent, or Firm—Hayes Soloway P.C.

(57) ABSTRACT

A method is disclosed for producing a transgenic plant with a modified inulin producing profile comprising in its genome a combination of one or more expressible 1-SST enzyme encoding genes and one or more expressible 1-FFT enzyme encoding genes, wherein either of these genes or both of them comprise one or more recombinant genes containing one or more 1-SST, respectively 1-FFT, enzyme encoding DNA sequences of plant origin or an expressible homologous sequence thereof. The invention also relates to a method for modifying and controlling the inulin profile of plants and to a method for producing inulin from said transgenic plants. Furthermore, a novel cDNA sequence of a 1-SST enzyme encoding gene of *Helianthus tuberosus* and a novel cDNA sequence of a 1-FFT enzyme encoding gene of *Cichorium intybus* are disclosed, novel recombinant DNA constructs and genes derived thereof, as well as novel combinations of expressible 1-SST and 1-FFT enzyme encoding genes. Moreover, the invention also relates to novel polypeptides, homologues thereof and fragments thereof, which have 1-SST activity of 1-FFT activity, and to antibodies capable of specifically binding one or more of them.

38 Claims, 20 Drawing Sheets

OTHER PUBLICATIONS

Sevenier, R., High Level fructan accumulation in a transgenic sugar beet Nature Biotechnology vol. 16, Sep. 1998, pp. 843–846.

Lazo, G., et al, "A DNA transformation–competent arabidopis genomic library in Agrobacterium" Biotechnology vol. 9, Oct. 1991 pps 963–967.

XP–002078408, FEBS Letters 385(1996) pp. 39–42 "Inulin Synthesis by a Combination of Purified Fructosyltransferases from Tubers of Helianthus Tuberosus" by Marcel Luscher, Christian Erdin, Norbert Sprenger, Urs Hochstrasser, Thomas Boller and Andres Wiemken.

* cited by examiner

Fig. 1  A33 Sequence

```
           10         20         30         40         50
      1234567890 1234567890 1234567890 1234567890 1234567890
      GCAAAAATCA CCATGGCTTC CACCCCCACC ACCCCTCTTA TTACTCACAA    50
                   M  A  S   T  P  T    T  P  L  I   T  H  N

TGACCTTGAA CAACGCCCGG AATCGACCGA GTCTCCACCC GGTCGATCAT   100
       D  L  E    Q  R  P  E   S  T  E   S  P  P   G  R  S  S

CCATCGTAAA GATCCTCACT GGATTATTTG TGTCCATTCT TGTTCTTTCA   150
       I  V  K    I  L  T   G  L  F  V   S  I  L    V  L  S

TCATTGGCTG CAATAACACA CCGGAAAACT CCCTTGCAGT CCACCACAGT   200
       S  L  A  A   I  T  H   R  K  T   P  L  Q  S   T  T  V

TGATATTGAA CCATCGACAA GCAGTCCGAA GGAGGTTGTG GGAGCGGATG   250
       D  I  E    P  S  T  S   S  P  K   E  V  V   G  A  D  D

ATAGCATTGA ATGGCAACGA TCTGCTTACC ATTTTCAACC CGATAAAAAT   300
       S  I  E    W  Q  R   S  A  Y  H   F  Q  P    D  K  N

TTCATTAGCG ATCCTGATGG TCCACTGTAT TACAAGGGAT GGTACCACTT   350
       F  I  S  D   P  D  G   P  L  Y   Y  K  G  W   Y  H  L

ATTCTACCAA TACAATCCGG GGTCAGCCAT TTGGGGCAAC ATAACATGGG   400
       F  Y  Q    Y  N  P  G   S  A  I   W  G  N   I  T  W  G

GTCATGCAGT CTCGAAAGAC CTCATCAATT GGTTCCACCT CCCTTTAGCC   450
       H  A  V    S  K  D    L  I  N  W   F  H  L   P  L  A

ATGGTTCCGG ATCACTGGTA CGACATCCAT GGTGTCATGA CTGGGTCCGC   500
       M  V  P  D   H  W  Y   D  I  H   G  V  M  T   G  S  A

CACCATCCTC CCCAATGGCC AAATCTTCAT GCTTTATAGC GGCAACGCCT   550
       T  I  L    P  N  G  Q   I  F  M   L  Y  S   G  N  A  Y

ACGACCTCTC TCAGCTTCAA TGCCTCGCGT ACCCCAAAAA TGCTTCTGAT   600
       D  L  S    Q  L  Q    C  L  A  Y   P  K  N   A  S  D

CCACTTCTTA TCGAATGGGT CAAATACGAA GGCAACCCAA TTCTCTTCCC   650
       P  L  L  I   E  W  V   K  Y  E    G  N  P  I   L  F  P

TCCTCCGGGC GTGGGTCTCA AAGACTTTAG GGACCCGTCA TCTCTTTGGA   700
       P  P  G    V  G  L  K   D  F  R    D  P  S    S  L  W  I

TTGGGCCCGA TGGGAAGTAC CGAATGGTTA TGGGCTCCAA GCACAATAAT   750
       G  P  D    G  K  Y    R  M  V  M   G  S  K    H  N  N

ACAATTGGTT GTGCTTTAAT TTACCACACC ACTAATTTCA CCCATTTTGA   800
       T  I  G  C   A  L  I    Y  H  T   T  N  F  T   H  F  E

ATTGTTGGAT GAGGTGCTCC ATTCGGTTCA GGGTACGGGT ATGTGGGAAT   850
       L  L  D    E  V  L  H   S  V  Q   G  T  G    M  W  E  C

GTGTTGATCT TTACCCCGTA TCCACGACCG AGACAAACGG GTTGGATATG   900
       V  D  L    Y  P  V    S  T  T  E   T  N  G   L  D  M

TCGAATCATG AGTCGGGTGC TAAGTATGTG TTGAAGCAAA GTGGGGATGA   950
       S  N  H  E   S  G  A   K  Y  V    L  K  Q  S   G  D  E

GGATAGACAT GATTGGTATG CAATTGGGGC ATATGACGTG GTTCATGATA  1000
       D  R  H    D  W  Y  A   I  G  A    Y  D  V   V  H  D  K

AATGGTATCC GGATGATCCG GAAATGGATT TGGGTATCGG GTTGAGATAT  1050
       W  Y  P    D  D  P    E  M  D  L   G  I  G   L  R  Y

GATTATGGAA AGTTTATGC TTCAAAGACG TTTATGACC CGAGTAAGAA    1100
       D  Y  G  K   F  Y  A    S  K  T    F  Y  D  P   S  K  K
```

Fig. 1 (Continued)    A33 Sequence

```
          10         20         30         40         50
     1234567890 1234567890 1234567890 1234567890 1234567890
     GAGGCGGGTC TTATGGGGCT ATGTTGGTGA AACGGATCCT CAAAAAGATG    1150
       R  R  V    L  W  G  Y  V  G  E  T  D  P   Q  K  D  D

ACCTCGAGAA AGGATGGGCC AATATTTTGA ATGTTCCTAG AACCGTGGTG    1200
       L  E  K    G  W  A    N  I  L   N  V  P  R   T  V  V

TTGGACACGA AGACGCAAAG TAACTTGATT CAATGGCCGG TCGAGGAAAC    1250
     L  D  T  K   T  Q  S   N  L  I    Q  W  P  V   E  E  T

AGAAACTTTG AGATCTGAAG AGTACGATGA GTTCAAAGAT GTTGAGTTGC    1300
      E  T  L    R  S  E  E  Y  D  E    F  K  D   V  E  L  R

GGCCTGGATC ACTTGTCCCG CTTGATATAG GCTCAGCCAC ACAGTTGGAC    1350
       P  G  S    L  V  P   L  D  I  G   S  A  T   Q  L  D

ATAAGTGCCT CATTCGAGGT TGATGAAGCT TTGCTGGGTG CAACCTTAGA    1400
      I  S  A  S   F  E  V   D  E  A   L  L  G  A   T  L  E

AGCCGATGTG TTGTTCAACT GCACCACGAG CGAGGGTTCA GCCATGAGGG    1450
       A  D  V    L  F  N  C   T  T  S   E  G  S   A  M  R  G

GTGTTTTGGG ACCGTTTGGG CTTGTGGTTC TTGCAGATTC GGCACTTTCA    1500
       V  L  G    P  F  G    L  V  V    L  A  D  S   A  L  S

GAACAAACTC CTGTTTACTT CTACATTGCG AAAAACTTGG ATGGCACTTC    1550
     E  Q  T  P   V  Y  F   Y  I  A    K  N  L  D    G  T  S

AAGAACTTAT TTCTGTGCTG ATGAATCAAG ATCATCAAAG CTTTTAGATG    1600
      R  T  Y    F  C  A  D  E  S  R    S  S  K    L  L  D  V

TGGGCAAGAT GGTATATGGA AGCAGTGTTC CTGTACTCCA TGGGGAAAAC    1650
      G  K  M    V  Y  G   S  S  V  P    V  L  H   G  E  N

TACGACATGA GGTTATTGGT GGATCATTCA ATAGTCGAAA GCTTTGCACA    1700
     Y  D  M  R   L  L  V   D  H  S    I  V  E  S   F  A  Q

AGGAGGAAGA ACGGTGATTA CATCAAGAGT GTATCCTACA ATGGCAATCT    1750
       G  G  R    T  V  I  T   S  R  V   Y  P  T   M  A  I  Y

ATGATGCCGC CAAAGTGTTT GTGTTCAACA ATGCAACTGG AATCACTGTT    1800
        D  A  A    K  V  F   V  F  N  N   A  T  G   I  T  V

AAGGCATCTC TCAAGATTTG GAAGATGGGT GGAGCACAAC TCAACCCTTT    1850
      K  A  S  L   K  I  W   K  M  G    G  A  Q  L   N  P  F

TCCTTTCTAA TTAGTTTAGT TGGCTTCATT AGTTGGTGAC GTTTTGGTGA    1900
       P  F

ATTTGTAAGC TTGTTGTAGT GAGGGCGGCC TTGATGATTA ATATTGCCAT    1950

TGTAAAACTT CCATTTTTTT AAAAAAATAA TCGATTTAAA AGTTTTTTTA    2000

AAAAAAAA                                                   2008
```

Fig. 2A       C86B Sequence

```
                10          20          30          40          50
        1234567890  1234567890  1234567890  1234567890  1234567890
        TCGCGGCCGC  GTCGACACTT  GGCCCATTTC  CCTCGAACAA  TGAAAACAGC    50
                                                         M  K  T  A

CGAACCCTTA  AGTGACCTTG  AGGATGCATC  CAACCGCACT  CCCCTACTAG   100
         E  P  L     S  D  L  E  D  A  S    N  R  T     P  L  L  D

ACCACCCTGC  ACCACCACCG  GCCGCCGTGA  AAAAGCAGTC  GTTCGTCAGG   150
         H  P  A     P  P  P     A  A  V    K  K  Q  S   F  V  R

GTTCTGTCCA  GTATCACTTT  GGTGTCTCTG  TTCTTCGTTT  TAGCTTTCGT   200
         V  L  S  S   I  T  L    V  S  L     F  F  V  L  A  F  V

ACTCATCGTC  CTGAACCAGC  AAGATTCCAC  GAACGCCACT  GCCAATTTAG   250
         L  I  V    L  N  Q  Q   D  S  T    N  A  T     A  N  L  A

CACTGCCGGA  GAAATCTTCG  GCTCAACACT  ATCAGTCCGA  TCGCCTGACA   300
         L  P  E    K  S  S     A  Q  H  Y  Q  S  D     R  L  T

TGGGAAAGAA  CAGCTTACCA  TTTTCAGCCA  GCCAAAAATT  TCATCTACGA   350
         W  E  R  T  A  Y  H     F  Q  P    A  K  N  F   I  Y  D

TCCCAATGGG  CCACTGTTCC  ACATGGGTTG  GTACCATCTT  TTCTATCAAT   400
         P  N  G     P  L  F  H  M  G  W    Y  H  L     F  Y  Q  Y

ACAACCCGTA  CGCTCCAATT  TGGGGCAACA  TGTCATGGGG  TCACGCCGTG   450
         N  P  Y    A  P  I     W  G  N  M   S  W  G    H  A  V

TCCAAAGACA  TGATCAACTG  GTTCGAGCTT  CCCGTAGCCT  TGACACCAAC   500
         S  K  D  M  I  N  W     F  E  L    P  V  A  L   T  P  T

CGAGTGGTAC  GATATCGAGG  GCGTCTTATC  CGGGTCCACC  ACGGCCCTCC   550
         E  W  Y    D  I  E  G   V  L  S    G  S  T     A  L  P

CCAACGGTCA  AATCTTTGCA  TTGTACACCG  GAAATGCTAA  TGATTTCTCT   600
         N  G  Q     I  F  A    L  Y  T  G  N  A  N     D  F  S

CAACTACAAT  GCAAAGCTGT  TCCGTTAAAC  ACATCTGACC  CACTCCTTCT   650
         Q  L  Q  C  K  A  V     P  L  N    T  S  D  P   L  L  L

CGAGTGGGTC  AAATACGAGA  ATAACCCAAT  CTTGTTCACT  CCACCAGGGA   700
         E  W  V    K  Y  E  N   N  P  I    L  F  T     P  P  G  I

TTGGATTAAA  AGACTATCGG  GACCCGTCTA  CAGTTTGGAC  GGGTCCTGAT   750
         G  L  K    D  Y  R     D  P  S  T  V  W  T     G  P  D

GGAAAACATC  GGATGATCAT  GGGCACTAAA  ATAAATCGTA  CTGGACTCGT   800
         G  K  H  R  M  I  M     G  T  K    I  N  R  T   G  L  V

ACTTGTTTAC  CATACTACCG  ACTTCACAAA  CTATGTAATG  TTGGAGGAGC   850
         L  V  Y    H  T  T  D   F  T  N    Y  V  M     L  E  E  P

CGTTGCATTC  GGTTCCCGAT  ACCGATATGT  GGGAATGTGT  TGACTTGTAC   900
         L  H  S    V  P  D     T  D  M  W  E  C  V     D  L  Y

CCTGTGTCAA  CAATTAATGA  CAGCGCACTT  GATATCGCGG  CTTATGGTCC   950
         P  V  S  T  I  N  D     S  A  L    D  I  A  A   Y  G  P

CGATATGAAG  CATGTGATTA  AAGAAAGTTG  GGAGGGACAT  GGGATGGACT  1000
         D  M  K    H  V  I  K   E  S  W    E  G  H     G  M  D  W

GGTACTCGAT  TGGGACATAT  GATGTGATAA  ACGATAAGTG  GACCCCGGAT  1050
         Y  S  I    G  T  Y     D  V  I  N  D  K  W     T  P  D

AACCCGGAAT  TGGACGTGGG  TATTGGGTTA  AGAGTCGATT  ACGGGAGGTT  1100
         N  P  E  L  D  V  G     I  G  L    R  V  D  Y   G  R  F
```

Fig. 2A (Continued)    C86B Sequence

|  | 10<br>1234567890 | 20<br>1234567890 | 30<br>1234567890 | 40<br>1234567890 | 50<br>1234567890 |  |
|---|---|---|---|---|---|---|
|  | TTTTGCATCA<br>F  A  S | AAGAGTCTTT<br>K  S  L  Y | ATGACCCGTT<br>D  P  L | GAAGAAACGG<br>K  K  R | AGGGTCACTT<br>R  V  T  W | 1150 |
|  | GGGGTTATGT<br>G  Y  V | TGCAGAATCG<br>A  E  S | GACAGTGCGG<br>D  S  A  D | ACCAGGACCT<br>Q  D  L | TAATAGAGGG<br>N  R  G | 1200 |
|  | TGGGCTACTA<br>W  A  T  I | TTTACAACGT<br>Y  N  V | TGCAAGAACC<br>A  R  T | ATTGTGCTAG<br>I  V  L | ATAGAAAGAC<br>D  R  K  T | 1250 |
|  | CGGAACCCAT<br>G  T  H | CTACTTCATT<br>L  L  H  W | GGCCTGTTGA<br>P  V  E | GGAAATTGAG<br>E  I  E | AGTTTGAGAT<br>S  L  R  Y | 1300 |
|  | ATGATGGTCG<br>D  G  R | TGAATTTAAA<br>E  F  K | GAGATCGAGC<br>E  I  E  L | TTGCACCGGG<br>A  P  G | TTCGATCATG<br>S  I  M | 1350 |
|  | CCACTCGACA<br>P  L  D  I | TAGGCCCGGC<br>G  P  A | TACGCAGTTG<br>T  Q  L | GACATAGTTG<br>D  I  V  A | CCACATTTGA<br>T  F  E | 1400 |
|  | GGTGGAACAA<br>V  E  Q | GAGACGTTTA<br>E  T  F | TGAGGACAAG<br>M  R  T  S | TGACACAAAT<br>D  T  N | GGTGAATACG<br>G  E  Y  G | 1450 |
|  | GTTGCACCAC<br>C  T  T | GAGCGCGGGT<br>S  A  G | GCAACCGAAA<br>A  T  E  R | GGGGAAGTTT<br>G  S  L | GGGACCGTTT<br>G  P  F | 1500 |
|  | GGGATCGCGG<br>G  I  A  V | TTCTTGCTGA<br>L  A  D | TGGAACACTC<br>G  T  L | TCGGAATTAA<br>S  E  L  T | CTCCTGTGTA<br>P  V  Y | 1550 |
|  | TTTCTATATT<br>F  Y  I | TCTAAAAAGA<br>S  K  K  T | CAGATGGAAG<br>D  G  S | CGTTGCAACA<br>V  A  T | CATTTTTGTA<br>H  F  C  T | 1600 |
|  | CCGATAAGCT<br>D  K  L | AAGGTCATCA<br>R  S  S | CTGGATTATG<br>L  D  Y  D | ACGGGGAGAG<br>G  E  R | AGTGGTATAC<br>V  V  Y | 1650 |
|  | GGGAGCACTG<br>G  S  T  V | TCCCTGTACT<br>P  V  L | CGATGGTGAA<br>D  G  E | GAACTCACAA<br>E  L  T  M | TGAGGTTACT<br>R  L  L | 1700 |
|  | GGTGGATCAT<br>V  D  H | TCAGTAGTGG<br>S  V  V  E | AGGGGTTTGC<br>G  F  A | AATGGGAGGA<br>M  G  G | AGGACAGTAA<br>R  T  V  M | 1750 |
|  | TGACATCACG<br>T  S  R | AGTGTATCCC<br>V  Y  P | ACAAAGGCAA<br>T  K  A  I | TATATGAAGG<br>Y  E  G | AGCCAAGATC<br>A  K  I | 1800 |
|  | TTCTTGTTCA<br>F  L  F  N | ACAATGCGAC<br>N  A  T | TCATACCAGT<br>H  T  S | GTGAAGGCAT<br>V  K  A  S | CTCTCAAGAT<br>L  K  I | 1850 |
|  | CTGGCAAATA<br>W  Q  I | GCTTCTGTAC<br>A  S  V  R | GAATCCAGCC<br>I  Q  P | TTACCCTTTT<br>Y  P  F | TAGTTATTTC | 1900 |
|  | GTTTCATGAA | CATGCTCTTT | TATTATATAT | ATTCATGTAT | TTTATTTTCC | 1950 |
|  | TTCTAGGTAA | AAAAAAAAAA | AAAAAAAAAA | AA |  | 1982 |

Fig. 2B   C33 Sequence

```
                10          20          30          40          50
       1234567890  1234567890  1234567890  1234567890  1234567890
       CGCGGCCGCG  TCGACCCCCA  CATGGCTTCC  TCTACCACCG  CCACCACCCC    50
                               M  A  S    S  T  T  A  T  T  P

TCTCATCCTC  CGTGATGAGA  CTCAAATCAG  CCCACAACTA  GCTGGATCTC   100
       L  I  L    R  D  E  T  Q  I  S     P  Q  L     A  G  S  P

CGGTGGGTCG  GCGTTTATCC  ATGGCCAATA  TCCTTTCCGG  GATCCTCGTT   150
       V  G  R    R  L  S     M  A  N  I  L  S  G     I  L  V

TTCGTCCTTG  TCATCTGTGT  TCTGGTTGCT  GTTATCCACG  ACCAATCACA   200
       F  V  L  V  I  C  V    L  V  A     V  I  H  D  Q  S  Q

ACAAACAATG  GCGACCAACA  ACCATCAGGG  AGAAGATAAA  CCCACCTCCG   250
       Q  T  M    A  T  N  N  H  Q  G     E  D  K     P  T  S  A

CCGCCACGTT  CACAGCTCCG  TTGCTACAAG  TTGATCTCAA  ACGGGTTCCC   300
       A  T  F    T  A  P     L  L  Q  V  D  L  K     R  V  P

GGAAAGTTGG  AATCCAATGC  TGATGTTGAG  TGGCAACGCT  CAGCTTACCA   350
       G  K  L  E  S  N  A    D  V  E     W  Q  R  S  A  Y  H

TTTTCAACCC  GATAAGAATT  TCATCAGCGA  TCCTGATGGT  CCAATGTATC   400
       F  Q  P    D  K  N  F  I  S  D     P  D  G     P  M  Y  H

ACATGGGGTG  GTACCATCTC  TTCTACCAGT  ACAACCCAGA  ATCAGCCATA   450
       M  G  W    Y  H  L     F  Y  Q  Y  N  P  E     S  A  I

TGGGGCAACA  TCACATGGGG  CCACTCCGTA  TCACGAGACA  TGATCAACTG   500
       W  G  N  I  T  W  G    H  S  V     S  R  D  M  I  N  W

GTTCCATCTC  CCATTCGCCA  TGGTCCCGGA  CCATTGGTAC  GACATCGAAG   550
       F  H  L    P  F  A  M  V  P  D     H  W  Y     D  I  E  G

GGGTCATGAC  CGGATCCGCC  ACGGTACTCC  CCAACGGTCA  GATCATCATG   600
       V  M  T    G  S  A     T  V  L  P  N  G  Q     I  I  M

CTCTACACTG  GCAACGCGTA  CGATCTCTCC  CAGTTACAGT  GCTTAGCATA   650
       L  Y  T  G  N  A  Y    D  L  S     Q  L  Q  C  L  A  Y

CGCCGTCAAC  TCATCTGATC  CTCTCCTTCT  GGAATGGAAA  AAGTACGAAG   700
       A  V  N    S  S  D  P  L  L  L     E  W  K     K  Y  E  G

GAAACCCAAT  TTTGTTCCCA  CCGCCTGGTG  TGGGATACAA  AGATTTTCGA   750
       N  P  I    L  F  P     P  P  G  V  G  Y  K     D  F  R

GATCCATCCA  CATTATGGAT  GGGTCCTGAT  GGGGAATGGA  GAATGGTAAT   800
       D  P  S  T  L  W  M    G  P  D     G  E  W  R  M  V  M

GGGGTCCAAA  CACAATGAAA  CTATTGGTTG  TGCATTGGTC  TACCGTACTA   850
       G  S  K    H  N  E  T  I  G  C     A  L  V     Y  R  T  T

CTAATTTTAC  GCATTTTGAA  CTGAATGAGG  AGGTACTCCA  CGCAGTCCCC   900
       N  F  T    H  F  E     L  N  E  E  V  L  H     A  V  P

CATACTGGTA  TGTGGGAATG  TGTGGACCTA  TACCCTGTGT  CCACCACGCA   950
       H  T  G  M  W  E  C    V  D  L     Y  P  V  S  T  T  H

CACGAATGGG  TTGGACATGA  AGGATAATGG  GCCGAATGTT  AAATATATTT  1000
       T  N  G    L  D  M  K  D  N  G     P  N  V     K  Y  I  L

TGAAACAAAG  TGGAGACGAA  GACCGACATG  ATTGGTATGC  GGTTGGGACT  1050
       K  Q  S    G  D  E     D  R  H  D  W  Y  A     V  G  T

TTTGACCCTG  AGAAAGATAA  GTGGTACCCT  GACGACCCTG  AAAACGATGT  1100
       F  D  P  E  K  D  K    W  Y  P     D  D  P  E  N  D  V
```

Fig. 2B (Continued)    C33 Sequence

```
          10         20         30         40         50
 1234567890 1234567890 1234567890 1234567890 1234567890

GGGAATCGGG TTGAGATACG ACTACGGAAA GTTCTATGCG TCAAAGACAT    1150
 G  I  G    L  R  Y  D    Y  G  K    F  Y  A    S  K  T  F

TTTATGATCA ACATGAAAAG CGGAGGGTAC TTTGGGGTTA TGTTGGTGAA    1200
 Y  D  Q    H  E  K     R  R  V  L   W  G  Y    V  G  E

ACCGACCCCC CTAAGTCCGA TCTTTTAAAG GGATGGGCTA ACATCTTGAA    1250
 T  D  P  P   K  S  D    L  L  K    G  W  A  N   I  L  N

TATCCCAAGG TCCGTTGTTT TGGACACGCA AACCGGAACC AATTTGATTC    1300
 I  P  R    S  V  V  L   D  T  Q    T  G  T    N  L  I  Q

AATGGCCGAT TGATGAAGTG GAAAAATTGA GATCAACAAA ATATGACGAA    1350
 W  P  I    D  E  V    E  K  L  R    S  T  K    Y  D  E

TTCAAAGACG TGGAGCTCCG ACCCGGATCA CTCGTTCCCC TCGAAATTGG    1400
 F  K  D  V   E  L  R    P  G  S    L  V  P  L   E  I  G

CACAGCGACA CAGTTGGACA TAAGTGCGAC ATTTGAAATC GATCAAAAGA    1450
 T  A  T    Q  L  D  I   S  A  T    F  E  I    D  Q  K  K

AGTTACAATC AACGCTTGAA GCCGATGTTT TGTTCAACTG TACAACTAGC    1500
 L  Q  S    T  L  E    A  D  V  L   F  N  C    T  T  S

GAAGGTTCAG TCCGGAAGGG TGTGTTGGGA CCATTTGGAA TCGTGGTTCT    1550
 E  G  S  V   R  K  G    V  L  G    P  F  G  I   V  V  L

AGCGGATGCC AACCGCTCTG AGCAACTTCC TGTGTATTTC TATATTGCCA    1600
 A  D  A    N  R  S  E   Q  L  P    V  Y  F    Y  I  A  K

AAGACACCGA TGGAACCTCA AAAACTTACT TCTGTGCTGA TGAATCAAGG    1650
 D  T  D    G  T  S    K  T  Y  F   C  A  D    E  S  R

TCATCGACGG ACAAATACGT TGGAAAATGG GTATACGGAA GCAGTGTTCC    1700
 S  S  T  D   K  Y  V    G  K  W    V  Y  G  S   S  V  P

TGTTCTTGAA GGTGAAAATT ACAACATGAG GTTACTGGTG GATCATTCGA    1750
 V  L  E    G  E  N  Y   N  M  R    L  L  V    D  H  S  I

TAGTGGAAGG GTTCGCACAA GGAGGAAGAA CGGTGGTGAC ATCAAGAGTG    1800
 V  E  G    F  A  Q    G  G  R  T   V  V  T    S  R  V

TACCCCACGA AGGCCATCTA TGGCGCTGCT AAGATATTTT TGTTCAACAA    1850
 Y  P  T  K   A  I  Y    G  A  A    K  I  F  L   F  N  N

CGCCACCGGA ATTAGCGTCA AGGCATCTCT CAAGATCTGG AAAATGGCGG    1900
 A  T  G    I  S  V  K   A  S  L    K  I  W    K  M  A  E

AAGCACAACT CGATCCATTC CCTCTTTCTG GGTGGAGTTC TTGATTATTA    1950
 A  Q  L    D  P  F    P  L  S  G   W  S  S

GAATTCGTCA TCCCTCTCTA TTTGTGTGTT ATTGTTGTGA AATATGGTAG    2000

CATGATTGCG GGTTTAGTGG GGGTATTATG GTAGTTTGTT AATGGTGGTT    2050

GTGGTACTGC ATTTGTGAGA TTATAAATTG AATTGTTATT CCTGTTTACA    2100

ACTTTTCTAA GCAAATGGTA TGTCATGTTT TGATCAAAAA AAAAAAAAA    2150
```

Fig. 4
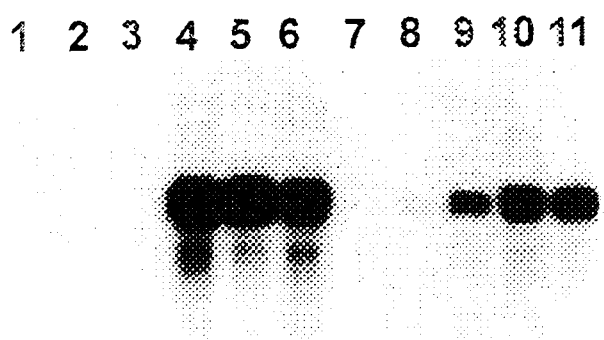
Fig. 4A
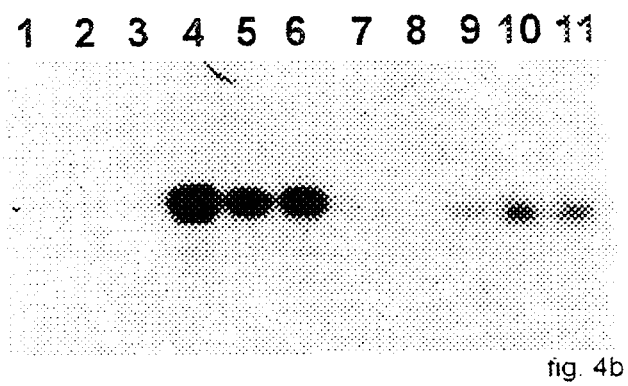
Fig. 4B
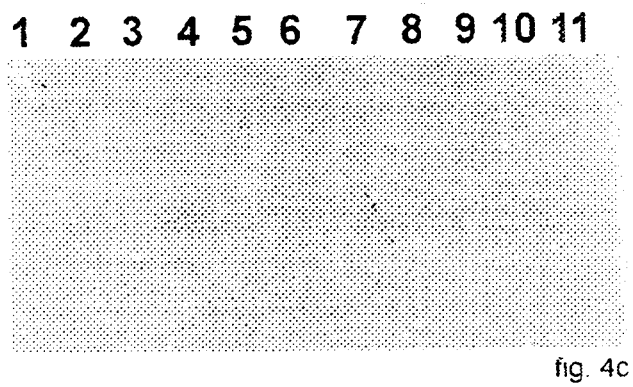
Fig. 4C 1 2 3 4 5
sst103
a33
c86b
fft111
Fig. 13
Northern blot analysis

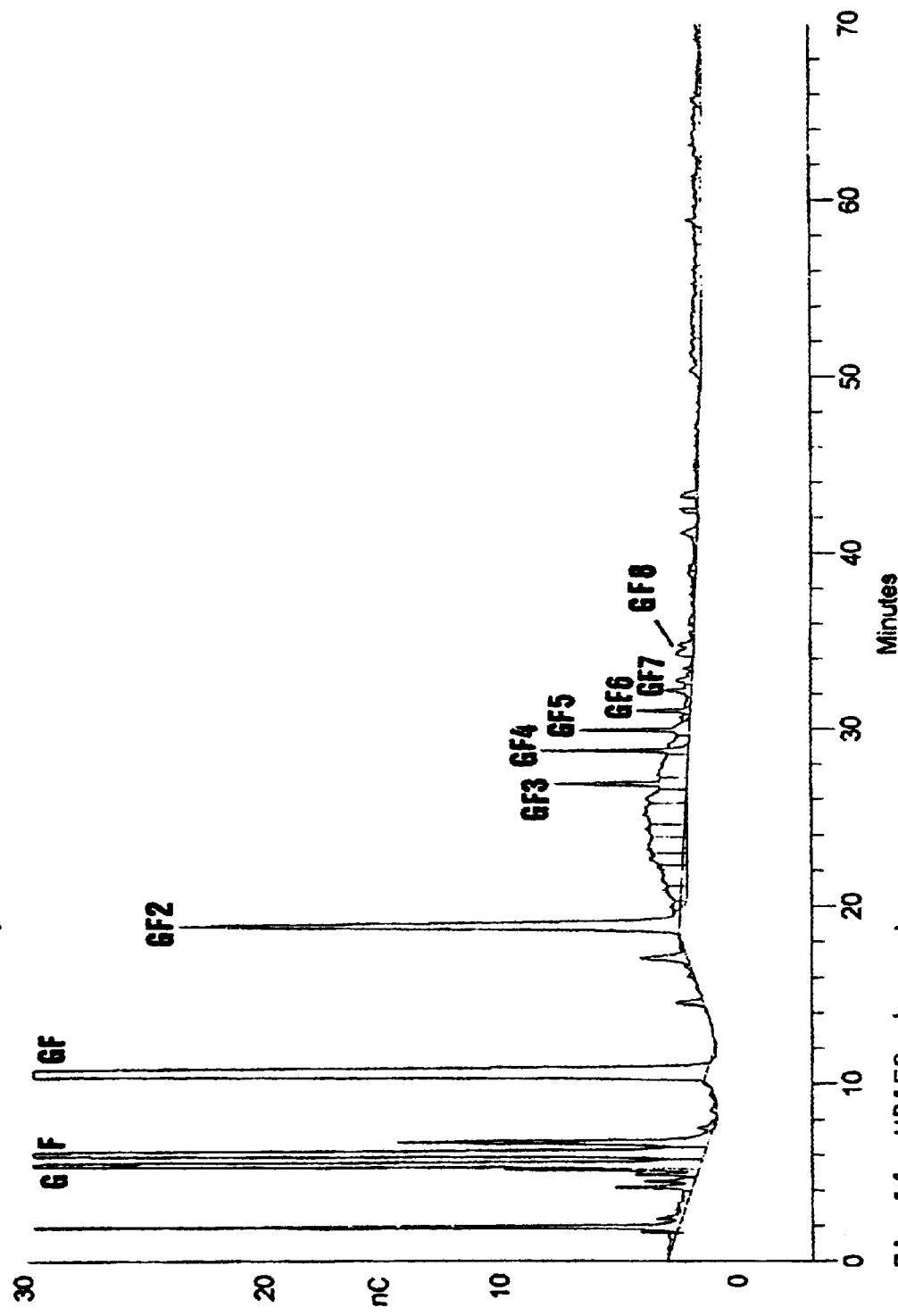

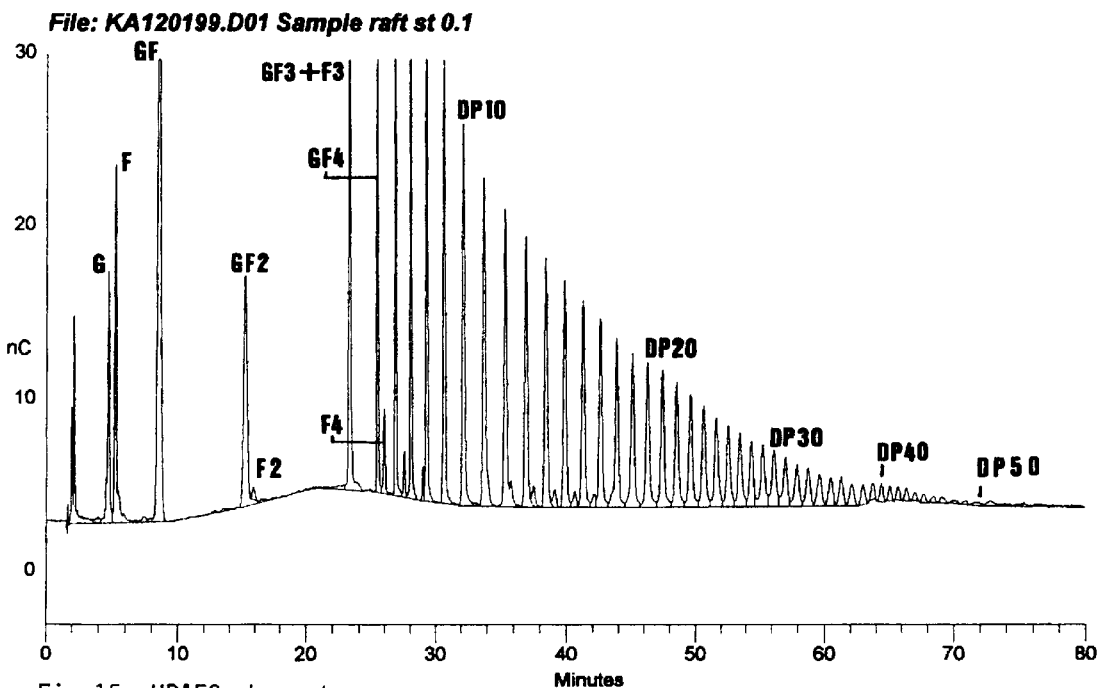
Fig. 15: HPAEC chromatogram
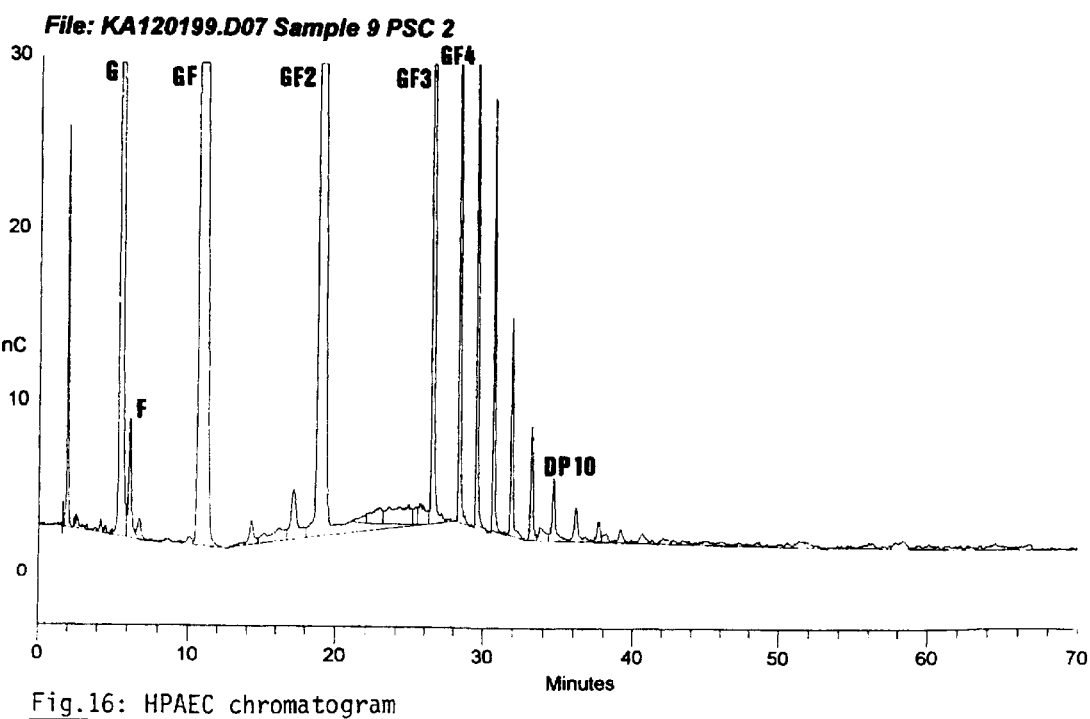
Fig. 16: HPAEC chromatogram

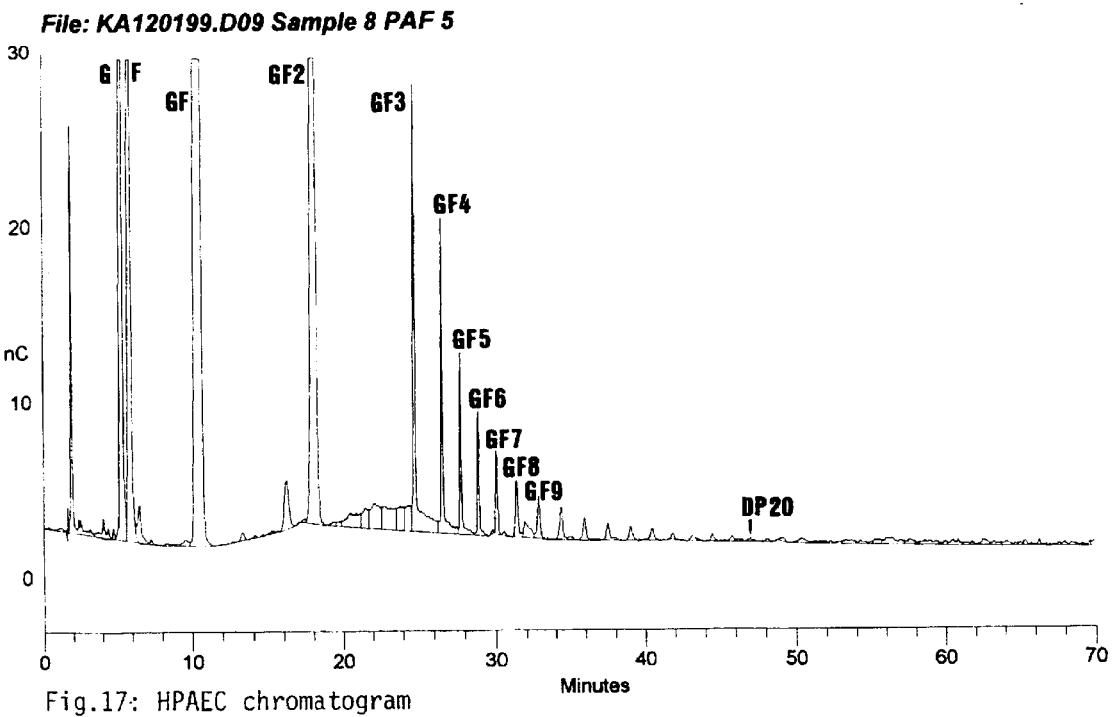
Fig. 17: HPAEC chromatogram
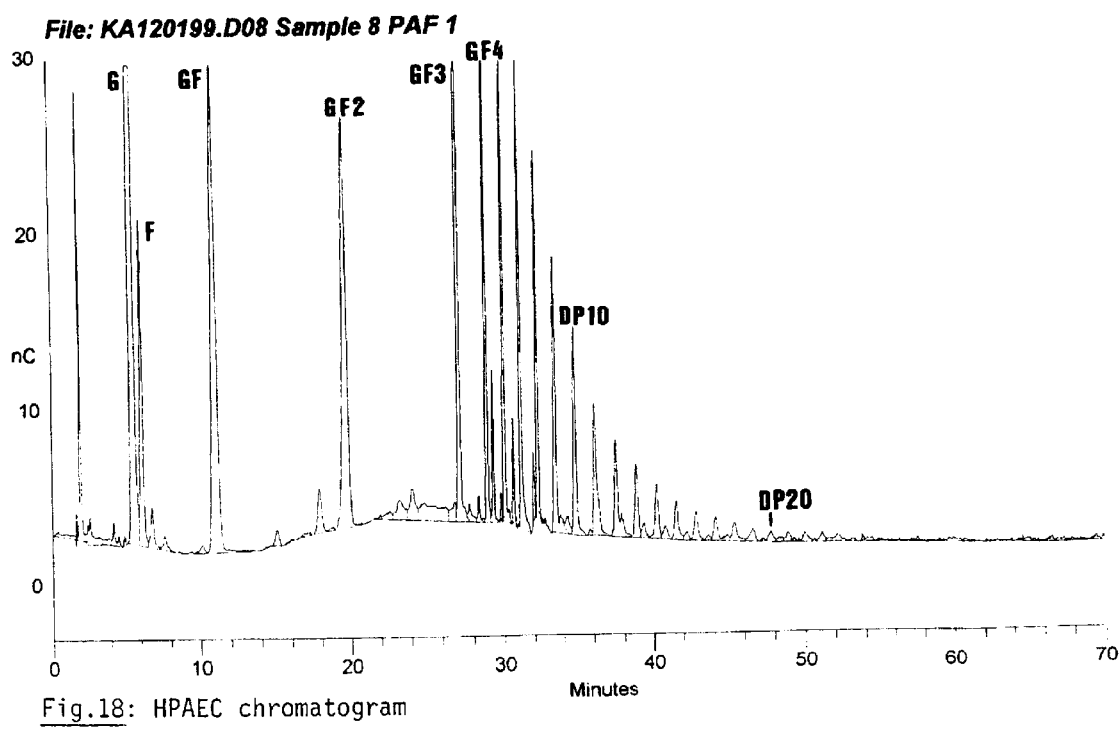
Fig. 18: HPAEC chromatogram

TRANSGENIC PLANTS PRESENTING A MODIFIED INULIN PRODUCING PROFILE

FIELD OF THE INVENTION

The present invention relates to transgenic plants presenting a modified inulin producing profile, to a method for producing said plants, to a method for modifying and controlling the inulin producing profile of plants and to a method for producing inulin from said transgenic plants.

Furthermore, the present invention relates to novel 1-SST and 1-FFT enzyme encoding DNA sequences, to novel recombinant DNA constructs and recombinant genes derived thereof, to novel combinations of expressible 1-SST and 1-FFT enzyme encoding genes, as well as to novel polypeptides or fragments thereof presenting 1-SST and/or 1-FFT activity, and to antibodies capable of binding to them.

BACKGROUND AND PRIOR ART

Inulin is a fructan type carbohydrate polymer which occurs as a polydisperse composition in many plants and can also be produced by certain bacteria and fungi. Inulin from plant origin consists of a polydisperse composition of mainly linear chains composed of fructose units, mostly terminating in one glucose unit, which are linked to each other through β(2-1) fructosyl-fructose linkages.

Inulin can be generally represented, depending from the terminal carbohydrate unit, by the formulae $GF_n$ and $F_m$, wherein G and F respectively represent a glucose unit and a fructose unit, n is an integer representing the number of fructose units linked to the terminal glucose unit, and m is an integer representing the number of fructose units linked to each other in the polyfructose chain.

The number of saccharide units (fructose and glucose units) in one molecule, i.e. the values n+1 and m in the above formulae, are commonly referred to as the degree of polymerisation, represented by DP. Often also the parameter (number) average degree of polymerisation, represented by $\overline{DP}$, is used, which is the value $\overline{DP}_n$ calculated, after complete hydrolysis and considering that in native inulins the $F_m$ fraction is negligible, as follows:

$$\overline{DP}_n = \frac{\text{total \% } F}{\text{total \% } G} + 1$$

In the equation % refers to weight percent (wt %). Furthermore, in this calculation the saccharides glucose (G), fructose (F) and saccharose (GF) which are present in the polydisperse polysaccharide, should not be taken into account. The average degree of polymerisation is thus the ($\overline{DP}_n$) of inulin, herein interchangeably referred to in short as ($\overline{DP}$) inulin or ($\overline{DP}$) (De Leenheer, 1996).

The polysaccharide chains of native inulin from plant origin generally have a degree of polymerisation (DP) ranging from 3 to about 100, whereas the ($\overline{DP}$) of the native inulin largely depends from the plant source, the growth phase of the plant, the harvesting time and the storage conditions. The ($\overline{DP}$) of isolated inulin largely depends on the ($\overline{DP}$) of the native inulin and on the process conditions used for the extraction, purification and isolation of the inulin from the plant or plant parts.

By native inulin or crude inulin is meant herein inulin that has been extracted from plants or parts of plants, without applying any process to increase or decrease the ($\overline{DP}$), while taking precautions to inhibit the plant's own hydrolase activity and to avoid hydrolysis. The ($\overline{DP}$) of native inulin thus essentially corresponds to the ($\overline{DP}$) of the inulin as present in the plant or plant parts.

The isolated inulin obtained from plants or plant parts through conventional manufacturing techniques, commonly including extraction, purification and isolation, without any process to modify the ($\overline{DP}$) of the native inulin, is termed herein, interchangeably, standard ($\overline{DP}$) grade inulin or standard grade inulin. As a consequence of the manufacturing process, the ($\overline{DP}$) of standard grade inulin is usually about 1 to 1.5 lower than the ($\overline{DP}$) of the native inulin.

Inulin molecules with a $DP \leq 10$ are commonly termed oligofructose, inulo-oligosaccharides or fructo-oligosaccharides (in short FOS). Both, inulin chains with a $DP \leq 10$ and inulin chains with a DP>10, are embraced herein by the term inulin.

By inulin profile is meant the relative composition of the polydisperse inulin as formed by the individual components including glucose, fructose, sucrose and individual inulin chains, including the distribution pattern of the polyfructose (inulin) chains.

Linear inulin is common in a specific plant family, the Asteraceae, including the plant species Jerusalem artichoke (*Helianthus tuberosus*) and chicory (*Cichorium intybus*). Inulin is commonly stored in tap roots (chicory) or in tubers (Jerusalem artichoke) and acts as a storage reserve for regrowth of the sprout after the winter period.

Accordingly, typical sources for the production of inulin at industrial scale are roots of chicory and, on a much smaller scale, tubers of Jerusalem artichoke, in which inulin can be present in concentrations of about 14% to 18% by weight on fresh weight. Inulin can be readily extracted from these plant parts, purified and optionally fractionated in order to remove impurities, monosaccharides, disaccharides and undesired oligosaccharides, as for example described in PCT patent application WO 96/01849.

Conventional processing of roots of chicory yields a standard grade inulin, containing about 8 wt % of mono- and di-saccharides (including glucose, fructose and sucrose) and a polydisperse mixture of inulin molecules with a DP ranging from 3 to about 60 and a ($\overline{DP}$) of about 10. The DP of the inulin molecules of standard grade inulin from Jerusalem Artichoke tubers ranges from 3 to about 40 whereas the ($\overline{DP}$) is about 7.

It is known that in Asteraceaous plants, including Jerusalem artichoke and chicory, inulin molecules are synthesised by the concerted action of two enzymes: sucrose:sucrose 1-fructosyltransferase (in short 1-SST enzyme or 1-SST, used interchangeably) and fructan:fructan 1-fructosyltransferase (in short 1-FFT enzyme or 1-FFT, used interchangeably) (Koops and Jonker, 1994 and 1996). Both 1-SST and 1-FFT are active during the period of inulin synthesis and accumulation:

1-SST catalyses the initial reaction of inulin biosynthesis, the conversion of sucrose into the smallest inulin molecule, the trisaccharide kestose (GFF), according to:

$$GF + GF \rightarrow GFF + G \tag{1}$$

1-FFT catalyses the redistribution of terminal fructosyl units (–F) between inulin molecules, which results in a stepwise increase in chain length, according to:

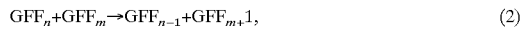

$$GFF_n + GFF_m \rightarrow GFF_{n-1} + GFF_{m+1}, \tag{2}$$

(wherein n and m are integers >0)

Some examples of this type of reaction are

GFF+GFF→GFFF+GF (2a)

GFFF+GFFF→GFFFF+GFF (2b)

GFFFF+GFFFF→GFFFFF+GFFF (2c)

An essential difference between the 1-SST enzyme and the 1-FFT enzyme is that the 1-FFT enzyme cannot catalyse reaction (1). In contrast, the 1-SST enzyme, next to reaction (1), can catalyse reactions of type (2) yielding inulin molecules with a low DP (catalysis by known 1-SST enzymes being able to yield inulin molecules with a DP up to about 5).

Accordingly, in plants both the 1-SST and the 1-FFT enzymes are contributing to inulin synthesis and the profile of native inulin is determined, inter alia, by sucrose supply, expression of the 1-SST enzyme encoding genes and 1-FFT enzyme encoding genes and the kinetic properties and relative activity of the 1-SST and 1-FFT enzymes which may be controlled by the relative expression of the 1-SST and the 1-FFT enzyme encoding genes.

Inulin is an edible, water soluble polydisperse polysaccharide composition which is used in the manufacture of many food and feed products, drinks and non-food products. In food, feed and drinks, inulin can be used, inter alia, as a bulking agent as well as a total or partial substitute for sugar and/or fat. Furthermore, inulin can be added to food, feed and drinks to enrich them with soluble fibres having prebiotic properties. Moreover, inulin can also be used as a component of prophylactic and therapeutic compositions. Besides, inulin with a ($\overline{DP}$) of about 10 and more is commonly used at industrial scale as starting material for the manufacture of oligofructose and of fructose, which both are increasingly used in industry as sweeteners, particularly in drinks and fruit compositions.

Usually different applications require inulin with a different profile. For example for use as (oligofructose) sweetener, the inulin molecules should have a low DP, preferably about 3 to 8, whereas for use as fat replacer inulin should preferably have a ($\overline{DP}$) higher than 15. For non-food applications inulin may have to be derivatised, for example to obtain carboxymethylated inulin which can be used as sequestering agent for divalent cations. Inulin suitable as starting material in derivatisation reactions should preferably have a ($\overline{DP}$) of at least 20, whereas its level of low molecular weight sugars should be very low. Standard grade inulin from chicory or Jerusalem artichoke has a too low ($\overline{DP}$) and a too high level of low molecular weight sugars, which makes derivatisation of said inulins difficult.

To prepare inulin which is low in mono- and disaccharides and has a high average degree of polymerisation, preferably a ($\overline{DP}$) of at least 20, various techniques have already been disclosed, for example, a method of manufacture involving a directed crystallisation starting from native or standard grade chicory inulin as described in PCT patent application WO 96/01849. Inulin with such a profile is also very suitable as ingredient in various food, feed, drinks and non-food applications, and as starting material for the manufacture of hydrolysates and derivatives of inulin.

To prepare oligofructose, usually standard grade chicory inulin or preferably chicory inulin with a higher ($\overline{DP}$), e.g. a ($\overline{DP}$) of at least 20, is subjected to partial, enzymatic hydrolysis, whereas to prepare fructose, typically in the form of a fructose syrup, said inulins are subjected to complete enzymatic or acidic hydrolysis, as for example described in patent applications PCT/BE97/00087 and EP 97870111.8.

However, every treatment of native inulin or standard grade inulin to reduce the content of low molecular weight sugars, to increase the ($\overline{DP}$) of the inulin, to modify the inulin profile, particularly to modify the distribution pattern of the inulin chains of the source inulin, or to transform inulin into oligofructose, requires one or more additional processing steps, such as, for example, size fractioning or hydrolysis. These additional process steps inevitably result in technical and economical disadvantages.

Accordingly, in the search for methods for producing inulin with a predetermined profile also an other approach is being prospected which envisages the direct production of inulin with a desired profile from genetically modified plants showing a modified inulin producing profile.

Herein the terms genetically modified, transformed and transgenic are used interchangeably; the terms 1-SST or 1-SST enzyme and 1-FFT or 1-FFT enzyme refer to the respective enzymes, whereas the terms sst103 or sst103 sequence and fft111 or fft111 sequence indicate an example of a 1-SST, respectively 1-FFT encoding DNA sequence, and the terms sst103 gene and fft111 gene indicate an example of a 1-SST, respectively a 1-FFT enzyme encoding gene.

PCT patent application WO 96/01904 claims a method for producing fructo-oligosaccharides from a transgenic plant containing a gene construct comprising a fructosyl transferase encoding ftf gene from *Streptococcus mutans* or a fructosyl transferase encoding Sac B gene from *Bacillus subtilus* or a mutated version of said genes. The invention aims particularly low molecular fructo-oligo-saccharides having a DP 3 to 4.

The patent application WO 96/01904 describes the isolation of an SST enzyme from onion and shows the activity of the purified enzyme in vitro by incubation with sucrose with the formation of 1-kestose only. Neither the DNA sequence coding for this SST enzyme nor the amino acid sequence of the purified SST enzyme were disclosed. The patent application also discloses the sequences of two other fructosyltransferases and the use of the 6-sft gene isolated from barley, where it is involved in the biosynthesis of non-inulin type branched fructans, in an heterologous screening leading to the isolation of the cDNA sequences of two virtually identical genes from the flowers of onion, respectively pAC22 and pAC92, which have been tested separately in protoplasts of tobacco. In the patent application (p. 19, line 27 to p. 20, line 2) it is indicated that in this way a fructosyltransferase activity could be shown but no experimental data were presented. Later experiments (Vijn et al., 1997) have revealed that pAC22 (designated pAC2 in Vijn et al., 1997) in fact encodes a 6-FFT enzyme (EMBL accession No Y07838) (fructan:fructan 6G-fructosyl transferase), which catalyses the transfer of a fructosyl residue to the carbon 6 of the glucose moiety of sucrose, resulting in the formation of the trisaccharide neokestose (F2-6G1-2F) according to: GFF+GF→FGF+GF, so that, although presenting fructosyltransferase activity, the disclosed sequences of pAC22 and pAC92 thus do not represent 1-SST coding sequences.

On the one hand there is an essential difference between a 6-G-FFT enzyme and a 1-SST enzyme since (i) the 6-G-FFT enzyme can not use saccharose as donor of a fructosyl residue (as a 1-SST enzyme does) but needs kestose as a fructosyl unit donor, and (ii) the 6-G-FFT enzyme catalyses the synthesis of neokestose (FGF) constituting the starting moiety for the building up of a fructan of the inulin neoseries class, whereas the 1-SST enzyme catalyses the synthesis of kestose (GFF) constituting the starting moiety for the building up of a fructan of the inulin class.

On the other hand there is an essential difference too between a 6-G-FFT enzyme and a 1-FFT enzyme, since the 6-G-FFT enzyme can catalyse only the production of polysaccharide chains with a low DP, i. e. a DP≦about 10, whereas a 1-FFT enzyme can catalyse the synthesis of polysaccharide chains with a higher DP, i.e. a DP up to about 70 and even up to about 100.

Said difference between the 6-G-FFT enzyme and the 1-SST enzyme, respectively the 1-FFT enzyme, is also reflected in the polysaccharide molecules built up through catalysis by said enzymes. The polysaccharide chains built up via a 6G-FFT enzyme catalysis are of the inulin neoseries class, reach a DP of only up to about 10, have not a terminal glucose moiety, and are not strictly linear as a result of the 16 disubstituted glucose moiety in the molecule, whereas the polysaccharide molecules built up via 1-SST enzyme and 1-FFT enzyme catalysis can reach a DP of up to about 70, even up to about 100, have a terminal glucose moiety, and present an essentially linear structure. Furthermore, the use of the individual sequences in different DNA constructs to produce transgenic plants, in particular different crops, is mentioned but no experimental data on the oligosaccharides obtained were given. Furthermore, Vijn et al., 1997 disclosed that introduction of the onion 6-G-FFT enzyme encoding sequence in chicory resulted in a transgenic plant which made linear inulins (i.e. genuine chicory inulin) and in addition fructans of the inulin neoseries. Apparently the native 1-SST enzyme encoding sequences together with the native 1-FFT enzyme encoding sequences of the chicory ensured via the corresponding enzymes the synthesis of the native inulin molecules, whereas the native 1-SST enzyme encoding sequences together with the onion 6G-FFT enzyme encoding sequence lead via the corresponding enzymes to the synthesis of inulin neoseries of low molecular weight. However, a combination in the genome of one and the same transgenic plant of a 1-SST encoding DNA sequence and a 1-FFT encoding DNA sequence, wherein either or both of said sequences are part of a recombinant construct, which combination is ensuring via the respective enzymes the production of inulin with a modified inulin profile (the host plant being an inulin or a non-inulin producing plant), has not been disclosed yet.

PCT patent application WO 96/21023 discloses a 1-SST encoding DNA sequence and a 1-FFT encoding DNA sequence both from J. artichoke, designated sst103 (or pSST103 when referring to the original clone being the sst103 inserted in the pBluescript SK vector) and fft111 (or pFFT111 when referring to the original clone being the fft111 inserted in the pBluescript SK vector), respectively, the construction of recombinant genes comprising said 1-SST enzyme or 1-FFT enzyme encoding sequence, and the transformation of plants (petunia and potato plants) by insertion of said sst103 gene or fft111 gene in the plant genome. Expression of the sst 103 gene in the transgenic plants was shown by analysis of the carbohydrate composition of the plants, revealing the presence of fructo-oligosaccharides with a DP up to 5. Expression of the fft111 gene in the transgenic plants was demonstrated in vitro on the basis of the ability of an extract of the transgenic plant to catalyse the synthesis of a polysaccharide $G-(F)_n$ (n>4) at the expense of submitted $G-(F)_4$ (G=glucosyl; F=fructosyl). No fructans were formed in the latter plants because the FFT enzyme needs fructo-oligosaccharides (such as FOS with DP of 3 or 4) for the synthesis of oligofructans and fructans with a higher DP. Based on the above, the patent application claims a method for producing a transgenic plant showing a modified inulin profile. A combination of DNA constructs comprising the 1-SST encoding DNA sequence, respectively the 1-FFT encoding DNA sequence, in one and the same transgenic plant has not been disclosed.

In food, feed, drinks and non-food applications, as well as for the manufacture of fructo-oligosaccharides, fructose and various derivatives of inulin, industry is increasingly making use of inulin. As a result thereof industry is continuously confronted with problems regarding the supply of inulin, particularly the supply of inulin compositions with desirable inulin profiles of highly linear polysaccharide chains. Said inulin compositions should preferably be readily and directly producible at industrial scale from plant sources at economically interesting costs. Preferably said production should be possible by conventional manufacturing processes and without additional process steps to modify the inulin profile of the native inulin, since each additional process step would inevitably increase the manufacturing costs and reduce the overall yield of suitable inulin.

OBJECT OF THE INVENTION

The object of the present invention is, inter alia, to provide a method by which said and other problems can be solved, as well as to provide means for use in said method.

SUMMARY OF THE INVENTION

As indicated above, in WO 96/21023 a 1-SST encoding DNA sequence, termed sst103, from the genome of J. artichoke is disclosed which codes for a 1-SST that catalyses in a plant the conversion of sucrose into kestose, thus enabling the plant to synthesise kestose (GFF), the smallest inulin molecule, from sucrose.

The inventors have now discovered the existence of a further 1-SST encoding DNA sequence in the genome of J. artichoke which apparently is part of a sleeping gene of said genome. The sequence has been identified in the form of its cDNA by DNA sequencing and this cDNA sequence, termed a33, is given in SEQ ID NO: 1 and is shown in FIG. 1 as A33. In FIG. 1 also the corresponding amino acid sequence is indicated, given in SEQ ID NO: 2.

Furthermore, the inventors have been able to identify a 1-FFT encoding DNA sequence in the genome of chicory and to identify its DNA sequence in the form of its cDNA by DNA sequencing. This cDNA sequence termed c86b, is given in SEQ ID NO: 3 and is shown in FIG. 2A as C86B, together with the corresponding amino acid sequence, given in SEQ ID NO: 4.

The inventors have found that the a33 cDNA sequence can be expressed in a host organism, particularly a plant or a plant part, to produce active 1-SST, when it is inserted in reading frame in a proper DNA construct in the genome of the organism. Said construct typically comprises the a33 cDNA sequence operably linked in the normal orientation to a promoter sequence and to a terminator sequence which are active in said host organism. When the host organism is a plant, the construct is preferably further comprising an operably linked DNA sequence encoding a targeting signal or a transit peptide which ensures targeting of the a33 encoded 1-SST enzyme to a specific subcellular compartment. The constructs, thus constituting a 1-SST enzyme encoding recombinant gene (in short herein 1-SST a33 gene), can be introduced into the genome of the host organism by conventional techniques.

Besides, the inventors have surprisingly found that said a33 cDNA sequence codes for an 1-SST enzyme which catalyses not only the transformation of sucrose to kestose and to lower oligofructoses (DP≦about 5), as do the known 1-SST enzyme encoding DNA sequences such as e.g. sst103 from J. artichoke, but encodes an 1-SST enzyme which is also able to catalyse the synthesis of higher fructo-oligosaccharides (DP up to about 10) in a plant. The a33 cDNA thus encodes in fact a 1-SST enzyme which has an activity which extends beyond the one of the known 1-SST enzymes, e.g. the 1-SST enzyme encoded by the sst103 cDNA, and has also an activity which is with respect to the building up of inulin chains functionally comparable to an aspect of a 1-FFT enzyme.

The inventors have also found that the c86b cDNA sequence can be expressed in a host organism, particularly a plant or a plant part, to produce active 1-FFT, when it is inserted in reading frame in a proper DNA construct in the genome of the host organism. Said construct typically comprises the c86b cDNA sequence operably linked in the normal orientation to a promoter sequence and to a terminator sequence which are active in said host organism. When the host organism is a plant, the construct is preferably further comprising an operably linked DNA sequence encoding a targeting signal or a transit peptide which ensures targeting of the c86b encoded 1-FFT enzyme to a specific subcellular compartment. The constructs, thus constituting a 1-FFT enzyme encoding recombinant gene (in short herein 1-FFT86b gene), can be introduced into the genome of the host organism by conventional techniques. Expression of said recombinant gene in a host plant results in the production of 1-FFT, which catalyses, as mentioned above, the stepwise synthesis of inulin by transformation of an oligofructose chain or inulin chain into an inulin molecule with a higher DP.

Furthermore, the inventors have found that a host organism, in particular a plant, can be transformed to comprise in its genome a combination of one or more expressible 1-SST enzyme encoding genes and one or more expressible 1-FFT enzyme encoding genes, wherein either the 1-SST enzyme encoding genes or the 1-FFT enzyme encoding genes or both comprise one or more recombinant genes containing one or more 1-SST enzyme encoding DNA sequences, respectively one or more 1-FFT enzyme encoding DNA sequences, of plant origin, resulting in a transgenic organism, particularly a transgenic plant, with a modified inulin producing profile.

Moreover, the inventors have found that the inulin producing profile of a plant and the profile of the inulin produced by a plant can be modified and even controlled, i.e. modified to yield a desired inulin profile, by producing a transgenic plant which comprises in its genome a combination of one or more expressible 1-SST enzyme encoding genes and one or more expressible 1-FFT enzyme encoding genes which code for 1-SST and 1-FFT enzymes with different kinetic properties. Either the 1-SST enzyme encoding genes or the 1-FFT enzyme encoding genes or both comprise one or more recombinant genes containing one or more 1-SST enzyme encoding DNA sequences, respectively one or more 1-FFT enzyme encoding DNA sequences, from plant sources, the latter 1-SST encoding sequences and 1-FFT encoding sequences being from the same or from different plant sources.

On the basis of said findings, the inventors have been able to provide a solution to the above mentioned and other problems by the present invention.

Accordingly, in a first embodiment, the invention relates to a method for producing a transgenic plant by transforming a host plant to comprise in its genome a combination of one or more expressible 1-SST enzyme encoding genes and one or more expressible 1-FFT enzyme encoding genes, wherein either the 1-SST enzyme encoding genes or the 1-FFT enzyme encoding genes or both comprise one or more expressible recombinant genes containing one or more expressible 1-SST enzyme encoding DNA sequences, respectively one or more expressible 1-FFT enzyme encoding DNA sequences which are of plant origin, comprising transforming a host plant by inserting one or more of said 1-SST enzyme encoding genes and/or one or more of said 1-FFT enzyme encoding genes into the genome of the host plant, yielding a transgenic plant with a modified inulin producing profile.

In accordance with the present invention, said 1-SST encoding DNA sequence(s) and said 1-FFT encoding DNA sequence(s) of said recombinant genes are not restricted to the sequences as obtained from the plant sources, but also include expressible homologous sequences thereof with a degree of homology of at least 70%, preferably at least 75%, more preferably at least 80% even more preferably at least 85%, and most preferably at least 90%, respectively, irrespective whether or not the homologous sequences are derived from plant sources or are obtained by mutagenesis of DNA sequences from plant sources or from microorganisms.

By inulin is meant herein fructans of the inulin class, i.e. molecules of the general formulae $GF_n$ and $F_m$, as defined above, exclusive of fructans of the inulin neoseries class corresponding to the general formula $$F2-(1F2)m'-6G1-(2F1)n'-2F$$

wherein F and G respectively represent fructose and glucose, and m' and n' represent integers which can be the same or different.

By modified inulin producing profile is meant the production of inulin by a transgenic plant which is quantitatively and/or qualitatively different from the production of inulin by the non-transformed host plant.

By modified inulin profile is meant an inulin profile which is qualitatively different from the one of the inulin produced by the host plant, i.e. an inulin composition wherein the ratio of monosaccharides, disaccharides, oligo-saccharides and/or the distribution pattern of the chain length of the individual inulin molecules, i.e. the DP and the ($\overline{DP}$), are different from the ones of the inulin composition produced by the non-transformed host plant. For the sake of convenience, the term modified inulin producing profile is embracing herein a modified inulin producing profile, a controlled inulin producing profile as well as a modified inulin profile and a controlled inulin profile.

The non-transformed host plant suitable for the invention can be an inulin producing plant containing in its genome one or more 1-SST encoding genes and 1-FFT encoding genes or only 1-SST encoding genes, or a non-inulin producing plant.

If in the genome of the host plant a 1-FFT encoding gene and/or a 1-SST encoding gene is present, when producing the desired transgenic plant according to the present invention said gene or genes can be maintained or their expression can be totally or partially suppressed by known techniques. For example the expression of said genes can be suppressed through anti-sense expression or co-suppression strategies.

The said 1-SST enzyme encoding genes, respectively the said 1-FFT enzyme encoding genes, of the genome of the transgenic plant in accordance with the present invention, can consist of a native gene or a mixture of different native genes, of a mixture of native and recombinant genes, or of one or more different recombinant genes.

If said combination of 1-SST encoding gene(s) and 1-FFT encoding gene(s) comprises known 1-SST encoding gene(s), respectively known 1-FFT encoding gene(s), these known genes may be the ones which are present in the genome of the non-transformed host plant.

If said combination comprises recombinant genes, their 1-SST enzyme encoding sequence, respectively the 1-FFT enzyme encoding sequence, can be a known one or a novel one, from a plant source, or a homologous sequence thereof, as defined above, which encodes a 1-SST enzyme, respectively a 1-FFT enzyme.

If both the 1-SST enzyme encoding genes and the 1-FFT enzyme encoding genes comprise a recombinant gene, the 1-SST enzyme encoding sequence(s) and the 1-FFT enzyme encoding sequence(s) of said recombinant genes can be from the same or from different plant species.

If more than one 1-SST enzyme encoding DNA sequence, respectively more than one 1-FFT enzyme encoding DNA sequence, is present in the genome of the transgenic plant, the 1-SST encoding sequences, respectively the 1-FFT encoding sequences, may be identical or not, may be present in one or in different genes, and these 1-SST encoding genes, respectively 1-FFT encoding genes, may be present on one or on different chromosomes.

In a preferred embodiment of the invention, the recombinant 1-SST encoding gene comprises said a33 cDNA sequence or an expressible homologous sequence thereof as defined above.

In another preferred embodiment, the recombinant 1-FFT encoding gene comprises said c86b cDNA sequence or an expressible homologous sequence thereof as defined above.

In a further preferred embodiment, the recombinant 1-SST encoding gene comprises said a33 cDNA sequence or said homologous sequence and the 1-FFT encoding gene comprises said c86b cDNA sequence or said homologous sequence.

Said homologous sequences are at least 70% identical to said a33 cDNA, respectively to said c86b cDNA, irrespective of whether or not the homologous sequences are derived from another plant species or are obtained by mutagenesis of fructosyltransferase-encoding sequences from plant sources or from micro-organisms. Preferably the degree of homology is at least 75%, more preferably at least 80%, and even more preferably at least 85%. Most preferably the degree of homology is at least 90%.

In a further preferred embodiment, the transgenic plant has been produced by inserting into the genome of a host plant a combination of one or more genes with a known 1-FFT enzyme encoding DNA sequence and one or more genes with the 1-SST enzyme encoding a33 cDNA sequence or said respective homologous sequences thereof which encode a 1-FFT enzyme, respectively, a 1-SST enzyme. In another preferred embodiment, the transgenic plant has been produced by inserting into the genome of a host plant a combination of one or more genes with a known 1-SST encoding DNA sequence and one or more genes with the 1-FFT enzyme encoding c86b cDNA, or said respective homologous sequences thereof. In a further preferred embodiment, the transgenic plant has been produced by inserting into the genome of a host plant a combination of one or more genes with the 1-SST enzyme encoding a33 cDNA sequence or a said homologous sequence thereof and one or more genes with the 1-FFT enzyme encoding c86b cDNA or a said homologous sequence thereof. In a still further preferred embodiment of said execution forms of the invention, the host plant is a non-inulin producing plant.

Typical combinations of 1-SST encoding genes and 1-FFT encoding genes according to the invention comprise respectively a 1-SST enzyme encoding sequence or a said homologous sequence thereof and a 1-FFT enzyme encoding sequence or a said homologous sequence thereof selected from plant species of the Asteraceae family, with the 1-SST encoding sequence and the 1-FFT encoding sequence being selected from the same or from different plant species.

Further typical combinations of 1-SST encoding genes and 1-FFT encoding genes according to the invention comprise respectively a 1-SST enzyme encoding sequence or a said homologous sequence thereof and a 1-FFT enzyme encoding sequence or a said homologous sequence thereof selected from plant species from the same or different plant families of the group consisting of the Asteraceae (Compositae) and Campanulaceae, comprising plant species such as, for example, Echinops, species, *Helianthus tuberosus, Cichorium intybus*, Dahlia species, Cynara species, Viguiera species, such as e.g. *Viguiera discolor, Viguiera deltoida, Viguiera annua, Viguiera lanata, Viguiera multiflora, Veronia herbacea, Scorzonera hispanica, Tragopogon porriflorus*, Taraxacum, species, *Arctium lappa, Campanula rapuncoloides* and *Bellis perennis*.

Typically suitable DNA sequences include, for example, the 1-SST encoding sequences sst103 (J. artichoke), a33 (J. artichoke), c33 (chicory), Genbank accession No U81520 (chicory), Genbank accession No Y09662 (*Cynara scolymus*), and the 1-FFT encoding sequences c86b (chicory) and fft111 (J. artichoke).

By the selection of a proper combination of one or more of said expressible 1-SST encoding genes and one or more of said expressible 1-FFT encoding genes, in combination with the selection of a proper ratio between the expression of the 1-SST encoding and 1-FFT encoding genes and the selection of a suitable host plant, a transgenic plant can be produced according to the invention with a desired modified inulin producing profile. In fact, the selection of proper combinations of said parameters by routine experiments, makes it possible to produce inulin with an almost tailored profile and to modify in a desired manner the inulin producing profile of a given host plant.

In a preferred embodiment, the genome of the transgenic plant comprises a combination of said expressible 1-SST encoding genes and said expressible 1-FFT encoding genes which induces the synthesis of native inulin with a degree of polymerisation which is higher, respectively lower, than the one of the native inulin produced, if any, by the non-transformed host plant.

When an inulin essentially composed of fructo-oligosaccharides with inulin chains with a DP$\leq$about 10 is desired, a method is provided according to a particular embodiment of the present invention, for producing a transgenic plant which produces inulin with such profile. This is very advantageous because no conventional, partial hydrolysis step of inulin with longer carbohydrate chains, such as e.g. standard grade chicory inulin with a ($\overline{DP}$) of about 10, needs to be included in the production process of said inulo-oligosaccharides. Accordingly, in a first variant, a method is provided for producing a transgenic plant by transforming a host plant to comprise in its genome a combination of one or more expressible 1-SST encoding genes, originating from the host plant or from a different plant source and one or more 1-SSTa33 genes. If the host plant contains a native 1-SST encoding gene and a native 1-FFT encoding gene in its genome, the expression of the native 1-FFT encoding gene or of both the native 1-SST encoding gene and the native 1-FFT encoding gene can optionally be suppressed by known techniques, for example through anti-sense expression. In a second variant, a transgenic plant is produced by inserting into the genome of a host plant which does not contain a 1-SST encoding gene nor a 1-FFT encoding gene, one or more 1-SST a33 genes or genes which contain a cDNA sequence which is an homologous sequence thereof, as defined above, which encodes an a33 1-SST enzyme. This particular embodiment of the present invention has become possible as a result of the fact that the 1-SST a33 gene codes for an enzyme which presents an activity of a 1-SST enzyme, i.e. catalysing the synthesis of kestose from sucrose, but also presents a moderate activity with respect to the building up of inulin chains which is comparable to an aspect of a 1-FFT enzyme activity, i.e. catalysing the synthesis of fructo-oligosaccharides from kestose or fructo-oligosaccharides with a low DP.

The selection of the optimal combination and ratio of the number of concerned 1-SST and 1-FFT enzyme encoding DNA sequences in combination with the selection of the most suitable plant species for the production of a desired inulin profile can be made by the skilled person according to conventional techniques, for example through routine experiments.

In the method according to the invention, the transgenic plant can be produced by inserting into the genome of the host plant by conventional techniques one or more expressible 1-SSTa33 genes or expressible homologues thereof, or one or more of said expressible 1-SST encoding genes from plant sources or said homologues thereof and/or one or more of said expressible 1-FFT encoding genes from plant sources or said expressible homologues thereof, resulting in a transgenic plant which comprises in its genome one or more 1-SSTa33 enzyme encoding genes or a combination of said 1-SST encoding genes and said 1-FFT encoding genes as defined herein above.

In a typical execution form, a cell of a host plant is transformed to comprise in its genome a said combination of 1-SST encoding genes and 1-FFT encoding genes as defined above, by inserting by conventional techniques one or more of said genes into the genome of the cell, followed by regenerating a transgenic plant from said transformed cell. If the host plant is transformed with both said 1-SST encoding genes and said 1-FFT encoding genes, the genes can be inserted into the host genome simultaneously or in subsequent steps.

In a typical execution form, said method comprises the following subsequent steps which can be carried out by conventional techniques:

i) the preparation of a recombinant gene construct comprising one or more 1-SST enzyme encoding DNA sequences, respectively 1-FFT enzyme encoding DNA sequences as defined above, operably linked to a promoter sequence active in said host plant and a terminator sequence active in said host plant, ii) introduction of the recombinant gene construct obtained in step i) into the genome of a cell of the host plant, and iii) regeneration of the transformed plant cell obtained in step ii) to the corresponding transgenic plant.

More specifically the method of the invention comprises preferably the following subsequent steps:

a) the construction of a recombinant gene, i.e. a recombinant DNA construct, comprising essentially the following sequences:
1. a promoter which ensures the formation of a functional RNA or a functional protein in the intended target plant, target organs, tissues or cells thereof,
2. one or more copies of a DNA sequence encoding respectively 1-SST or 1-FFT enzyme, functionally connected to said promoter,
3. a transcription terminator operationally connected to said 1-SST or 1-FFT enzyme encoding DNA sequence,
4. a DNA sequence encoding a targeting signal or a transit peptide which ensures targeting of the 1-SST enzyme, respectively the 1-FFT enzyme to a specific subcellular compartment, b) the introduction of the recombinant gene obtained in a) into the genome of the host plant yielding genetically modified material, typically a cell, comprising said combination of 1-SST enzyme and 1-FFT enzyme encoding sequences, and regeneration of the genetically transformed material in the corresponding transformed host plant.

In the recombinant DNA construct according to the present invention, one or more copies of the 1-SST and 1-FFT enzyme encoding DNA sequences are preferably linked to one or more regulatory sequences which are operational in the host plant ensuring proper expression of said DNA sequence at a sufficiently high expression level in the host plant, in the different plant organs, tissues or cells. Regulatory sequences are, for example, a promoter, a termination signal and a transcription or translational enhancer. A promoter can, for example, be the 35S promoter of the cauliflower mosaic virus (CaMV) or an organ-specific promoter like the tuber-specific potato proteinase inhibitor II promoter, or any other inducible or tissue-specific promoter.

The production of inulin being particularly advantageous in organs storing large amounts of sucrose, such as the tap roots of sugar beet or the stems of sugar cane, a highly preferred promoter is a promoter which is active in organs and cell types which normally accumulate sucrose (the primary substrate for inulin synthesis).

The production of inulin is particularly advantageous in the vacuole which can accumulate very high concentrations of sucrose (e.g. up to about 500 mol m$^{-3}$). Accordingly, in the recombinant DNA according to the present invention, the DNA sequence encoding 1-SST or 1-FFT enzyme is preferably linked to a sequence encoding a transit peptide which directs the mature 1-SST or 1-FFT enzyme protein to a subcellular compartment containing sucrose, such as for example said vacuole.

In a preferred embodiment, the host plant is a non-inulin producing plant; in another preferred embodiment, the host plant is an inulin producing plant.

Typical host plants for use in the method according to the invention are plants which can easily be grown, which are rather resistant to attack by injurious organisms such as insects and fungi, which give a high yield of plant material per hectare and which can be easily harvested and processed. Besides, said plants should after transformation be able to produce large amounts of inulin, give a high content of produced inulin based on fresh plant material and preferably be able to deposit said inulin in a concentrated manner in parts of the plant, preferably in tap roots or tubers, which can be easily harvested, stored and processed.

Other typical host plants for use in the method of the invention are non-inulin producing plants which are quite sensitive to abiotic stresses such as, for example, drought, cold, and other ones. Transformation of said host plants according to the present invention resulting in a transgenic plant which is producing inulin, even in a quite low level, may significantly increase the resistance of the plant against said abiotic stresses, particularly against drought and/or cold.

Typical host plants suitable for use in the method according to the invention include corn, wheat, rice, barley, sorghum, millets, sunflower, cassava, canola, soybean, oil palm, groundnut, cotton, sugar cane, chicory, bean, pea, cow pea, banana, tomato, beet, sugar beet, Jerusalem artichoke, tobacco, potato, sweet potato, coffee, Gocoa and tea.

In a further embodiment, the present invention provides a method for modifying the inulin producing profile of a plant and for controlling the profile of the inulin produced by a plant, which comprises genetically transforming a plant by inserting into its genome one or more expressible 1-SSTa33 genes or expressible homologues thereof, or one or more expressible 1-SST encoding genes, and/or one or more expressible 1-FFT encoding genes, as defined above, yielding a transgenic plant comprising in its genome a combination of said 1-SST encoding genes and said 1-FFT encoding genes, as defined herein above, which plant, when cultured under conventional conditions, shows a modified inulin producing profile.

In still another embodiment, the present invention relates to a method for producing inulin from plant material, particularly inulin with a modified profile, by conventional techniques, wherein the source plant material for the method is material, typically tap roots or tubers, from a transgenic plant which comprises in its genome one or more expressible 1-SST a33 enzyme encoding genes, or a combination of one or more expressible 1-SST encoding genes and one or more expressible 1-FFT encoding genes, or expressible homologues of said genes, as defined above. Such transgenic plant is obtainable by a method of the present invention as described herein before.

The production of inulin from plant parts is well known in the art and commonly comprises (i) an isolation step, wherein the crude, native inulin is isolated from the plant material (typically involving extraction of shredded plant parts e.g. tap roots or tubers, with warm water ), followed by (ii) a purification step, typically comprising a depuration treatment (involving liming and carbonatation or another flocculation technique and filtration) followed by a refining treatment (involving treatment over ion-exchangers, treatment with active carbon and filtration) and optionally a concentration of the purified inulin solution, and (iii) an isolation step wherein the inulin is isolated in particulate form from the purified inulin solution obtained in (ii), for example by spray-drying or by directed crystallisation, filtration and drying.

The invention further embraces the novel DNA sequences a33 cDNA and c86b cDNA, and homologous sequences thereof, as defined above, encoding respectively 1-SST enzyme and 1-FFT enzyme, as well as novel recombinant DNA constructs, novel recombinant genes and vectors comprising one or more of said novel cDNA sequences. Said novel cDNA sequences are suitable intermediates for the construction of said novel recombinant DNA constructs and recombinant genes, which are in turn, suitable intermediates and tools for the production of transgenic plants presenting a modified inulin producing profile according to the present invention.

The invention furthermore embraces a novel combination of one or more expressible 1-SST encoding genes and one or more expressible 1-FFT encoding genes, wherein either the 1-SST encoding genes or the 1-FFT encoding genes or both comprise one or more recombinant genes of which one or more of the 1-SST enzyme encoding DNA sequences and one or more of the 1-FFT enzyme encoding DNA sequences are of plant origin or homologues thereof, as defined above. Said novel combination of genes constitutes a suitable intermediate and tool for the production of transgenic plants according to the present invention.

The invention also embraces a transgenic plant, producible by a method according to the present invention, the genome of which comprises a combination of one or more expressible 1-SST encoding genes and one or more expressible 1-FFT encoding genes, as defined above.

The present invention also includes cells, plant tissue, plant parts, roots and shoots of transgenic plants according to the invention as well as seeds thereof, which comprise in their genome a combination of one or more expressible 1-SST encoding genes and one or more expressible 1-FFT encoding genes, as defined above.

The present invention also includes novel inulin compositions, i.e. inulin having a novel inulin profile, obtainable by a method according to the present invention, and the use thereof in the manufacture of food, feed, drinks, and non-food compositions, of derivatives of inulin , and of partial and complete hydrolysates of inulin.

In still a further embodiment, the present invention relates to a purified and isolated polypeptide having an amino acid sequence as shown in SEQ ID NO:2, respectively in SEQ ID NO: 4, and to purified and isolated respective homologues thereof having at least 70% homology, preferably at least 75%, more preferably at least 80%, even more preferably at least 85%, and most preferably at least 90% homology, as well as to a fragment of said polypeptides, which polypeptides, said homologues thereof and said fragments thereof have 1-SST, respectively 1-FFT, activity.

Said polypeptides, homologues and fragments can be obtained according to conventional techniques. For example the polypeptides of SEQ ID NO: 2 and of SEQ ID NO: 4 can be obtained from chicory roots through a purification procedure based on ammonium sulphate precipitation, followed by lectin affinity chromatography, anion- and cation exchange chromatography.

In an ultimate embodiment, the present invention relates to antibodies capable of specifically binding one or more polypeptides and/or homologues and/or fragments thereof as defined above.

BRIEF DESCRIPTION OF THE FIGURES

FIG. 1: shows the nucleotide sequence (SEQ ID NO: 1) (A33) and deduced amino acid sequence (SEQ ID NO: 2) of the isolated a33 cDNA FIG. 2A: shows the nucleotide sequence (SEQ ID No. 3) (C86B) and deduced amino acid sequence (SEQ ID No. 4) of the isolated c86b cDNA.

FIG. 2B: shows the nucleotide sequence (SEQ ID No. 5) (C33) and deduced amino acid sequence (SEQ ID No. 6) of the isolated c33 cDNA.

FIG. 4: depicts a Northern blot analysis of RNA isolated from various tissues from *Helianthus tuberosus*.: RNA was isolated from dormant tubers (lane 1), sprouting tubers (lane 2), stolons (lane 3), tubers with a 2–5 mm diameter (lane 4), tubers with a 2–2.5 cm diameter (lane 5), tubers with a 5–7 cm diameter (lane 6), leaves (lane 7), stems (lane 8), fibrous roots (lane 9), receptacle (lane 10) and flower (lane 11). RNA was probed with an sst103 (FIG. 4A), fft111 (FIG. 4B) or a33 PCR fragment (FIG. 4C).

with a ALMV translational enhancer (amv), the coding sequence of a33 (a33) and the nos-termination signal (Tnos).

Figure 6:
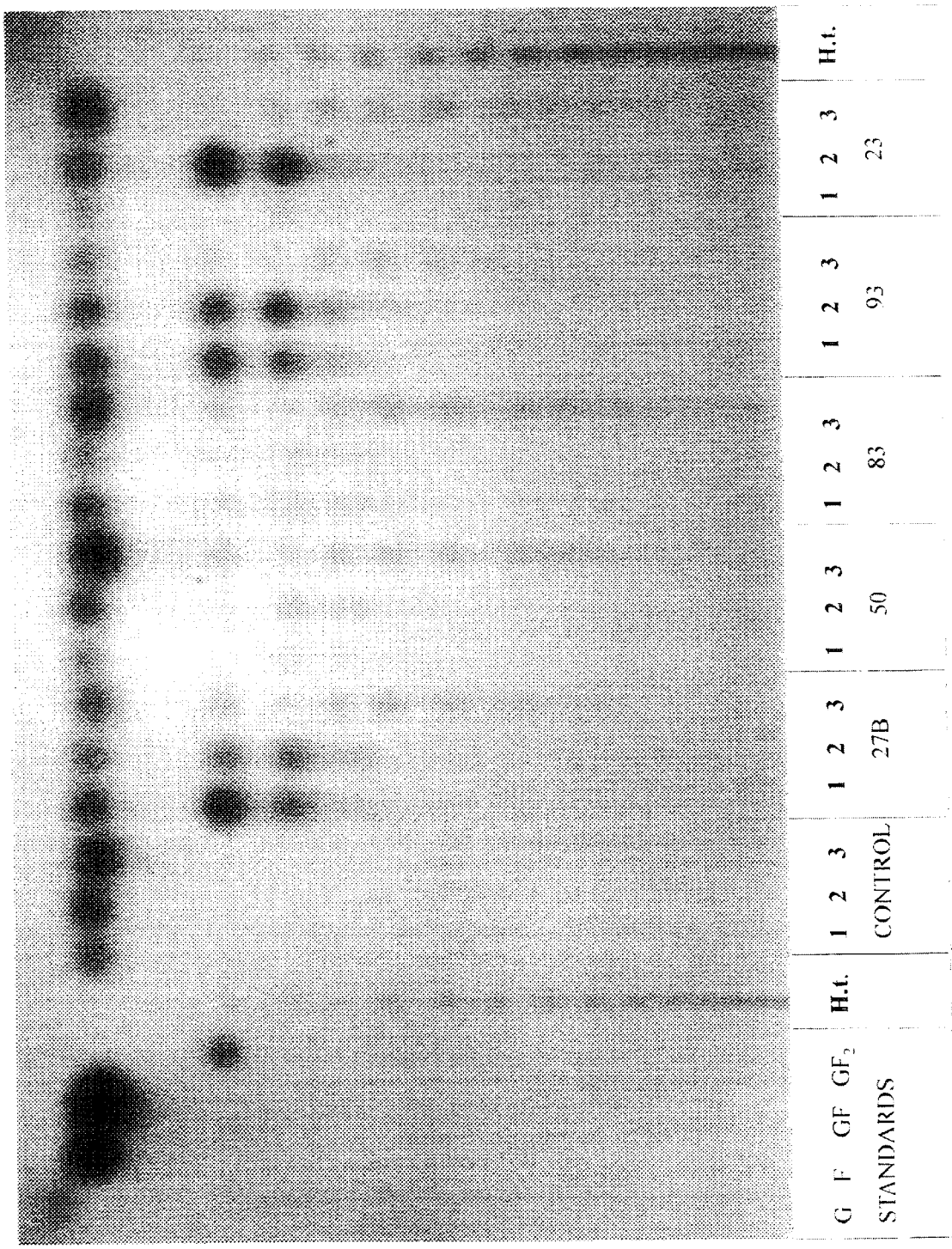

FIG. 6.: shows a TLC analysis of leaves and tubers of transgenic potato harbouring the pA33.236 construct. TLC plates were developed twice in 90% aqueous acetone., G=glucose standard, F=fructose standard GF=sucrose standard, $GF_2$ is the $GF_2$ standard, H.t.=standard fructan mixture from mature tubers of *H. tuberosus*. Plant no 27B, 50, 83, 93 and 23 represent individual potato plants harbouring the pA33.236 construct. Control is a control plant harbouring the AGL0 construct. Form each plant (control plant as well as transgenic plants) two tubers were analysed (lanes 1 and 2) and one leaf (lane 3).

Figure 7:
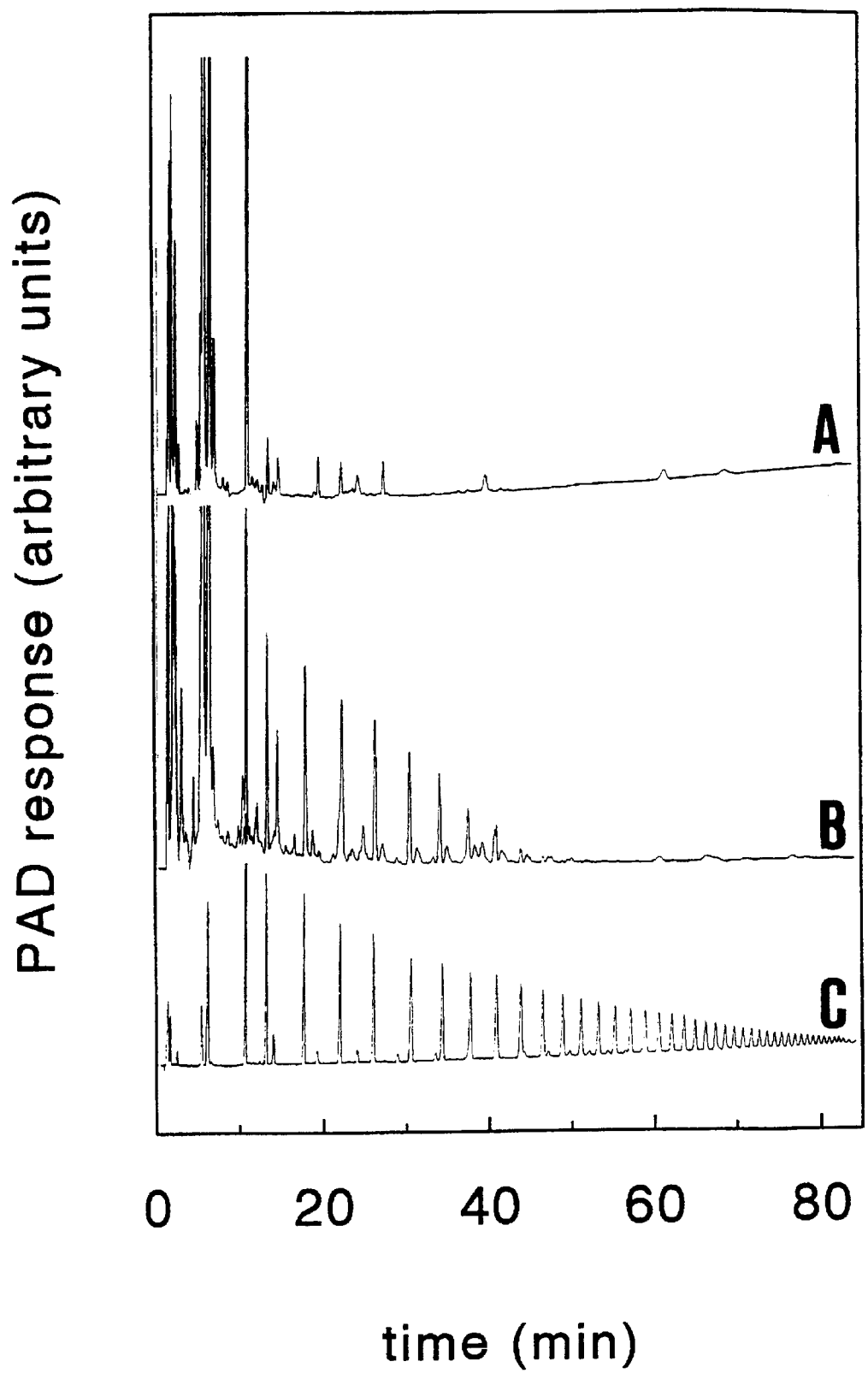
Figure 8:
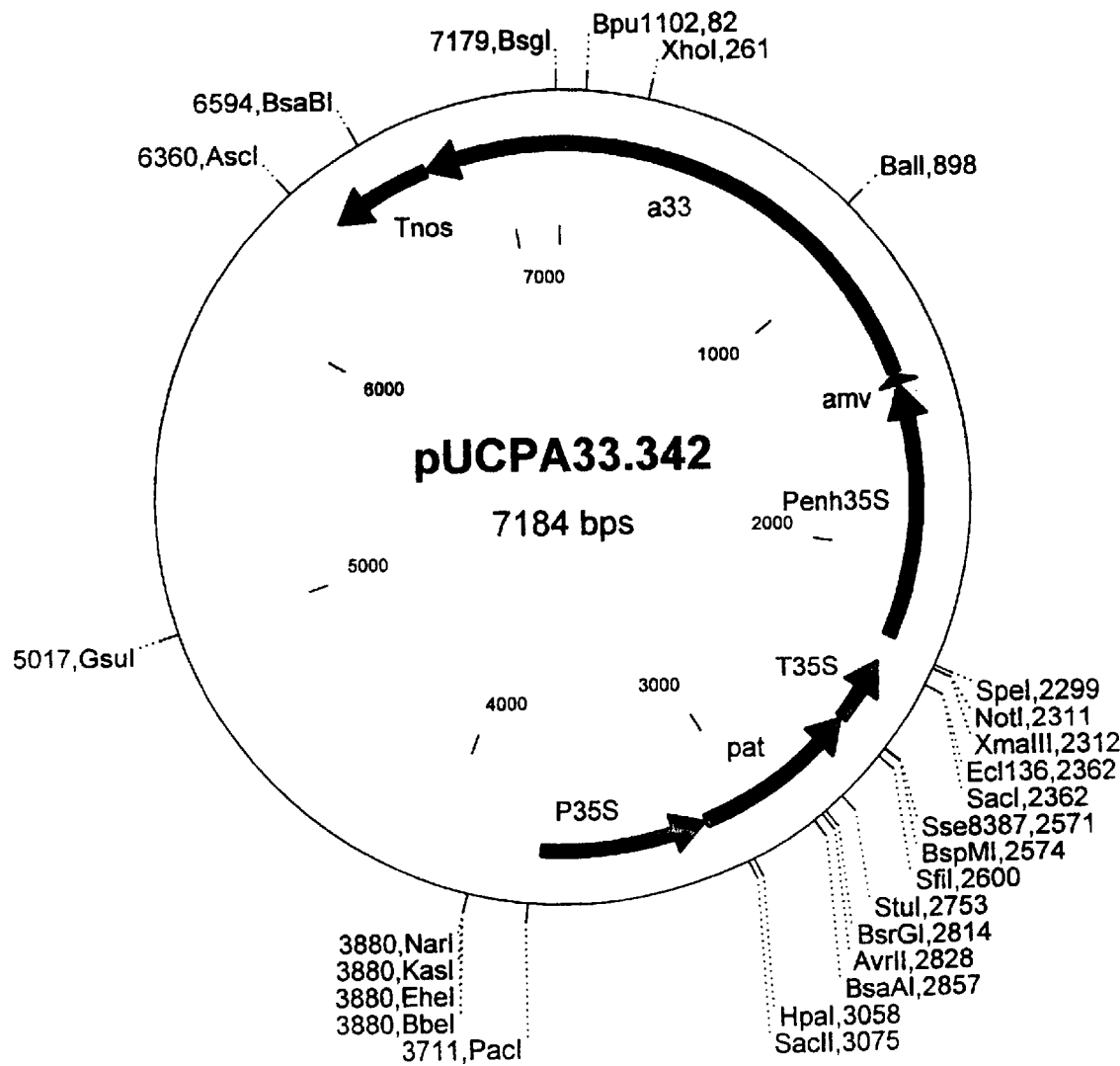

FIG. 7: shows HPAEC separations of carbohydrates extracted from leaves of control potato transformed with AGL0 lacking the binary vector (A), from leaves of transgenic potato harbouring the pA33.236 construct (B) and a standard inulin extracted from chicory tap roots (C), FIG. 8: represents the chimeric gene construct pUCPA33.342 consisting of the coding sequence of a33 (a33) under control of the enhanced CaMV35S promoter (Penh35S) and the nos-termination signal (Tnos), the ALMV translational enhancer (amv), and the herbicide resistance gene (pat) under control of the promoter (P35S) and terminator sequences (T35S) of the CaMV35S gene.

Figure 9:
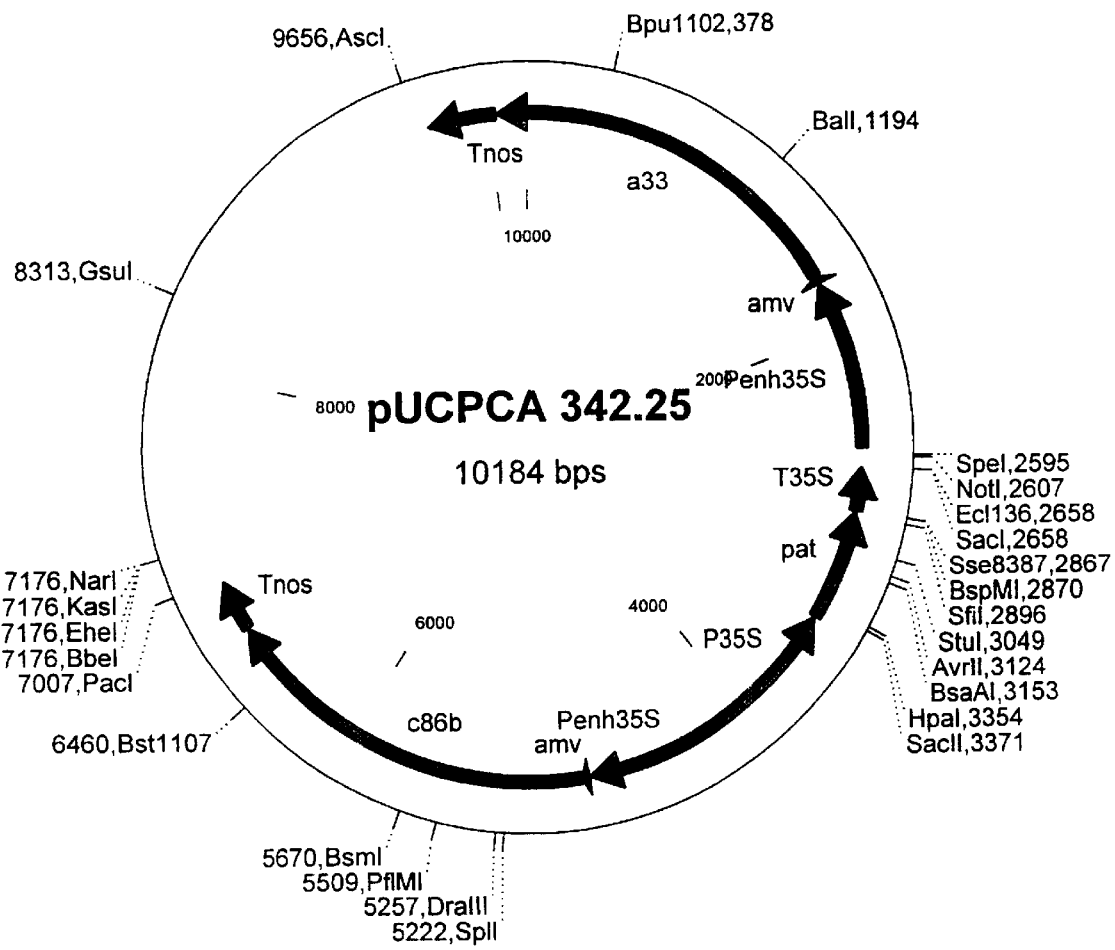

FIG. 9: represents the chimeric gene construct pUCPCA342.25 harbouring the coding sequences of a33 (a33) and c86b (c86b), each under control of the enhanced CaMV35S promoter (Penh35S) and the nos terminator (Tnos), the ALMV translational enhancer (amv), and the herbicide resistance gene (pat) under control of the promoter (P35S) and terminator sequences (T35S) of the CaMV35S gene.

Figure 10:
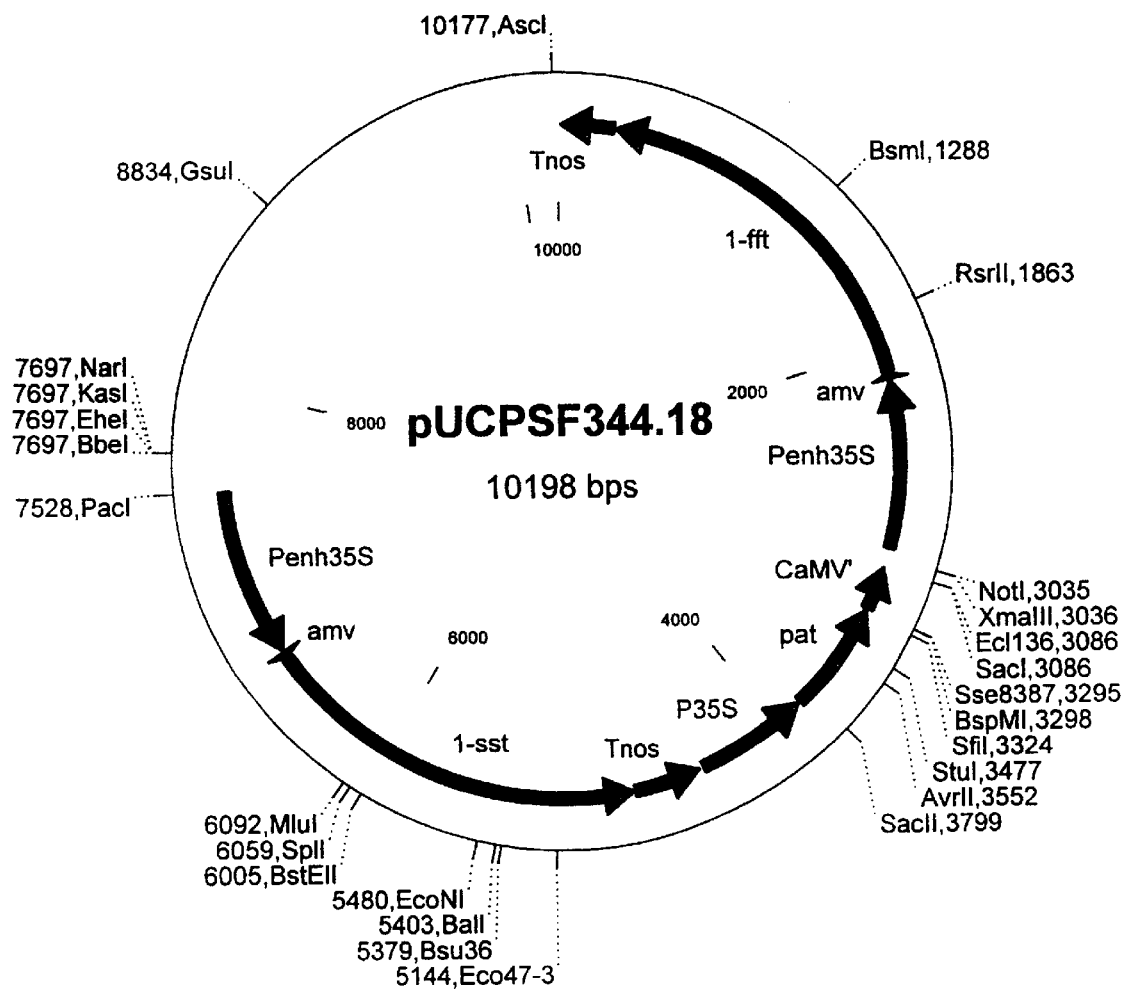

FIG. 10: represents the chimeric gene construct pUCPSF344.18 harbouring the coding sequences of fft111 (1-fft) and sst103 (1-sst), each under control of the enhanced CaMV35S promoter (Penh35S) and the nos-termination signal (Tnos), the ALMV translational enhancer (amv), and the herbicide resistance gene (pat) under control of the promoter (P35S) and terminator sequences (T35S) of the CaMV35S gene.

Figure 11:
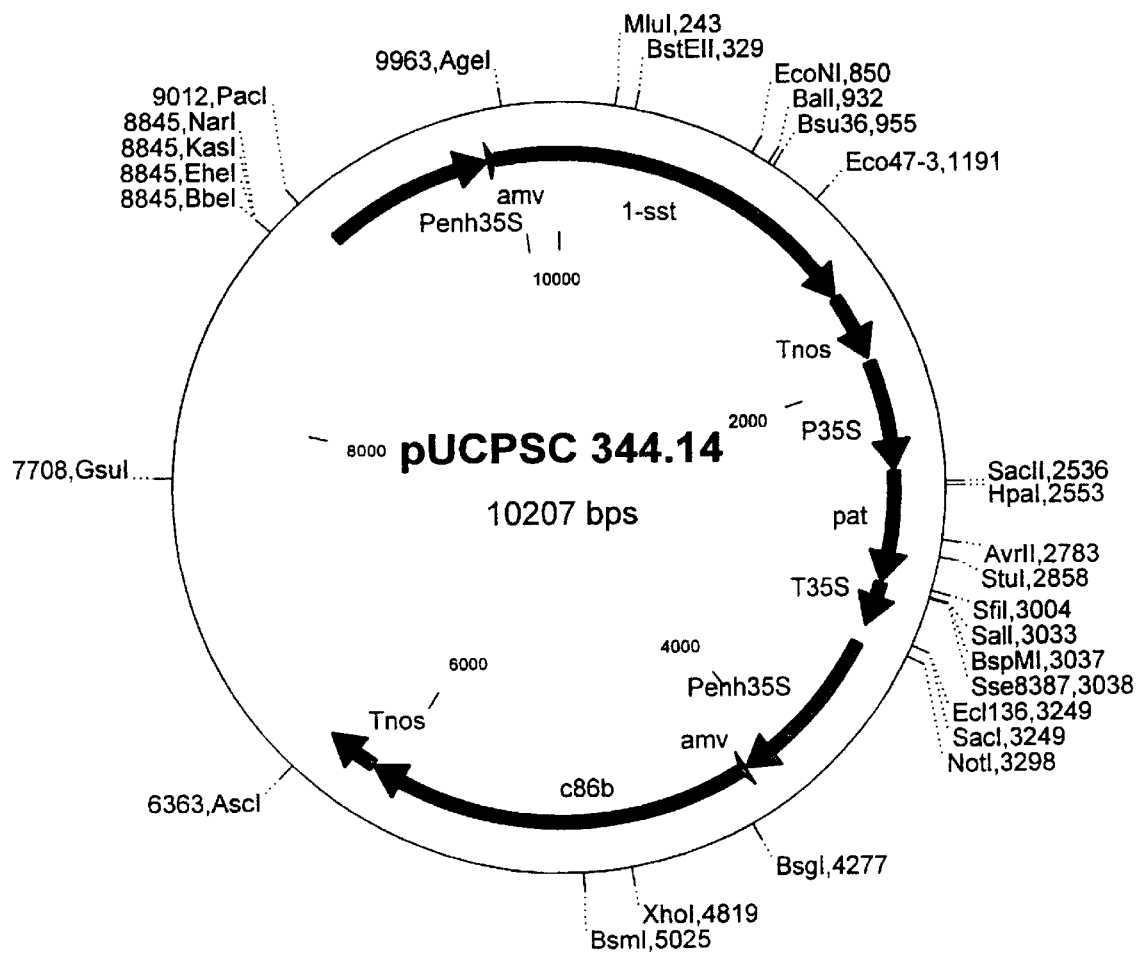

FIG. 11: represents the chimeric gene construct pUCPSC344.14 harbouring the coding sequences of c86b (c86b) and sst103 (1-sst), each under control of the enhanced CaMV35S promoter (Penh35S) and the nos-termination signal (Tnos), the ALMV translational enhancer (amv), and the herbicide resistance gene (pat) under control of the promoter (P35S) and terminator sequences (T35S) of the CaMV35S gene.

Figure 12:
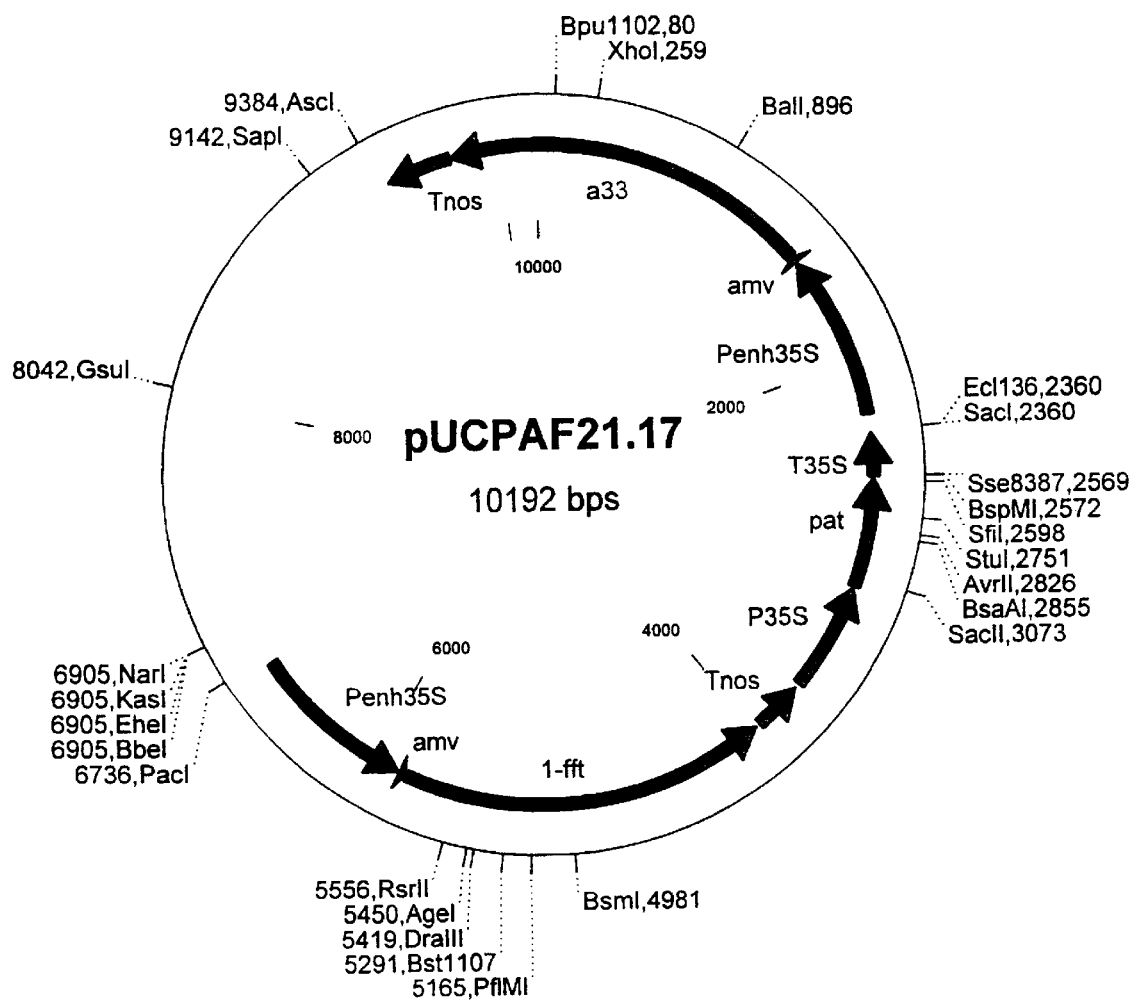

FIG. 12: represents the chimeric gene construct pUCPAF21.17 harbouring the coding sequences of a33 (a33) and fft111 (1-fft), each under control of the enhanced CaMV35S promoter (Penh35S) and the nos-termination signal (Tnos), the ALMV translational enhancer (amv), and the herbicide resistance gene (pat) under control of the promoter (P35S) and terminator sequences (T35S) of the CaMV35S gene.

FIG. 13: depicts a Northern blot analysis of RNA isolated from leaves of sugar beets: RNA was isolated from transgenic sugar beet line 7PSF22 (lane 1), transgenic line 9PSC2 (lane 2), transgenic line 8PAF1 (lane 3), transgenics line 8PAF5 (lane 4) and a non-transgenic control sugar beet (lane 5). The RNA was probed with DNA fragments specific for sst103, a33, c86b or fft111.

FIG. 14: shows HPAEC separations of carbohydrates extracted from tap root of transgenic sugar beet line 7PSF22 expressing the sst103 and fft111 genes.

FIG. 15: shows HPAEC separations of carbohydrates extracted from tap root of chicory.

FIG. 16: shows HPAEC separations of carbohydrates extracted from tap root of transgenic sugar beet line 9PSC2 expressing the sst103 and c86b genes.

FIG. 17: shows HPAEC separations of carbohydrates extracted from tap root of transgenic sugar beet line 8PAF5 expressing the a33 and fft111 genes.

FIG. 18: shows HPAEC separations of carbohydrates extracted from tap root of transgenic sugar beet line 8PAF1 expressing the a33 and fft111 genes.

DETAILED DESCRIPTION OF THE INVENTION

The present invention results in significant technical and economical advantages. At first, the invention provides novel plant sources of inulin thus helping to solve the problem of sufficiency of inulin supply. Said plant sources may comprise known inulin producing plants which as a result of a genetically modification according to the invention produce more inulin and/or inulin of a preferred modified profile entailing improved functional properties, as well as non-inulin producing plants which have been transformed to produce inulin, particularly inulin having a desired profile. Secondly, the method according to the present invention enables to obtain directly, i.e. without any additional process steps such as e.g. size fractioning or partial hydrolysis, inulin with a certain desirable inulin profile, such as inulin essentially composed of inulin chains with a DP$\leq$10. This obviously has considerable advantages with respect to manufacturing and manufacturing costs.

Furthermore, the invention provides the possibility of producing many transgenic plant species and variants thereof within the scope of the present invention, resulting from the flexibility of the method of the present invention for producing a transgenic plant with a modified inulin producing profile. Indeed, the possibility to produce many different transgenic plants, starting from different host plant species and by using various different combinations of the 1-SST and/or 1-FFT enzyme encoding sequences according to the invention, i.e. including different 1-SST, respectively 1-FFT enzyme encoding DNA sequences originating from various different plant species or homologous sequences thereof, as defined above, and different ratio's of said 1-SST, respectively 1-FFT enzyme encoding DNA sequences, enables to produce various inulin compositions with a different, desired profile. Said desired inulin profile is often translated in improved functional properties of the inulin and commonly in improved physico-chemical and/or organoleptic properties of end products containing said inulin, and of hydrolysates and of derivatives of said inulin.

The invention enables furthermore to produce transgenic plant species like for example cultural crops and ornamental plants with an increased resistance against abiotic stresses like e.g. drought and/or cold, which also results in economically important advantages.

The polypeptides, homologues and fragments thereof, as defined above, may be used to catalyse specific in vitro chemical reactions, such as, for example, the use of polypeptide of SEQ ID NO: 2 in the synthesis of 1-kestose from sucrose by a fructosyl transfer reaction; the use of polypeptide of SEQ ID NO:4 in the synthesis of fructo-oligosaccharides or inulin by a fructosyl transfer reaction from fructo-oligosaccharides; and the use of a combination of the polypeptides of SEQ ID NO:2 and SEQ ID NO:4, or respective homologues or fragments thereof as defined above, for the synthesis of fructo-oligosaccharides and inulin from one or more carbohydrates selected from the group consisting of sucrose, 1-kestose and oligofructoses.

The invention is further described in detail in the experimental part below, comprising the methodology and examples. It is emphasised that the examples are given as merely illustrative, non-limitative examples of the invention.

DNA METHODOLOGY

DNA and RNA isolation, subcloning, restriction analysis and sequencing were performed using standard methods described in molecular biology manuals (e.g. Sambrook et al. 1989; Ausubel et al. 1994).

DNA and protein alignments were performed using the DNA analysis software Genworks 2.5.1. (Intelligenetics, Inc., CA). This program uses a progressive alignment method, building the alignment in approximate phylogenetic order using an algorithm similar to FASTA. Protein alignments use a PAM-250 scoring matrix.

Construction and Screening of a cDNA Library from *H. tuberosus*

Ten µg of poly(A)$^+$RNA isolated from tubers of *Helianthus tuberosus* 'Colombia', harvested in July, was used as starting material for the construction of an Uni-ZAP XR cDNA library (Stratagene, La Jolla, Calif., USA). Construction, plating and screening of the library were performed according to the protocols developed by Stratagene (USA, cat. no. 237211). About 100.000 plaques of the unamplified cDNA library of *H. tuberosus* were blotted onto Hybond N$^+$ (Amersham) membranes and screened with a probe comprising two DNA fragments. A 840 bp DNA fragment was synthesised by PCR using primers 5'-TACGCTGTCAACTCGTCGG-3' and 5'-TTGAATAGAACATCGGGCTCTAGCG-3' and plasmid pSST103 (sst103 cDNA in pBluescript phagemid, Van der Meer et al. 1998) as a template. A 860 bp DNA fragment was obtained by PCR using primers 5'-GTTCAACGCTGCTTGATCCACC-3' and 5'-ACCACGGTCCTTCCAAACGG-3' and plasmid pFFT111 (fft111 cDNA in pBluescript phagemid Van de Meer et al., 1998) as a template. The two PCR fragments were radiolabelled by the RadPrime DNA labelling system (Life Technologies). Hybridisation was at 50° C. in 500 mM NaP-buffer, pH 7.2,7% SDS, 1% BSA, 1 mM EDTA. Filters were washed to a final stringency of 2×SSC, 0.1% SDS at 50° C. (2×30 min) and finally exposed to X-omat AR (Kodak). Positive plaques were purified in 34 rounds of plaque hybridisation. The pBluescript phagemids were excised from the Uni-ZAP vector using the Exassist/Solr system (Stratagene). The inserts were analysed by restriction enzyme analysis and sequencing.

Construction and Screening of a cDNA Library from *Cichorium intybus*

Ten µg of poly(A)$^+$RNA isolated from tap roots of *Cichorium intybus* 'Cassel', which was harvested in July, was used as starting material for the construction of a lambda TriplEx cDNA library (Clontech laboratories). Construction, plating and screening of the library were performed according to the protocols developed by Clontech (Palo Alto, Calif., cat. no. CS1010t). About 60.000 plaques of the unamplified chicory library were screened with a mixture of the two $^{32}$P-labelled DNA probes obtained by PCR and RadPrime labelling as described above. Hybridisation and washing of Hybond-N$^+$ membranes were performed under low stringency conditions (hybridisation at 50° C., final wash step with 2×SSC, 0.1% SDS, 50° C.). Positive plaques were purified in 3–4 rounds of plaque hybridisation. The lambda Trip1Ex clones were converted into pTriplEx clones using the cre-recombinase mediated site-specific recombination at the loxP sites flanking the embedded pTriplEx (Clontech). The pTriplEx clones were analysed by restriction enzyme analysis and DNA sequencing.

PCR

PCR was performed in 50 µl PCR buffer (Life Technologies), containing 100 pmol plasmid as a template, and 100 pmol of gene specific primers (specific for sst103, fft111, a33, c33, or c86b, depending on the experiment). Amplification involved 30 cycles of denaturing (0.5 min, 92° C.), annealing (1 min, 55° C.) and amplification (1 min, 72° C.). The resulting fragments were checked by DNA sequencing and restriction digestion to confirm the identity.

Transformation of Potato

Transformation of potato was performed according to Visser (1991), with the following modifications. Stem internodes, cut from in vitro grown *Solanum tuberosum*, were placed in R$_3$B agar plates, on top of filter paper, which was soaked with 2 ml PACM medium. The internodes were incubated 24 h at 21° C. The binary plasmid pA33.236 was introduced into the *Agrobacterium tumefaciens* strain 'AGL0' (Lazo et al. 1991) by adding 0.5 microgram of plasmid DNA to 200 microliter of competent Agrobacterium cells. Competent cells were prepared according to Sambrook (1989). The plasmid DNA-Agrobacterium mixture was incubated on ice, for 30 min, then frozen in liquid nitrogen and thawed in a water bath at 37° C. for 5 min. After addition of 1 ml YEP medium, the bacteria were incubated at 28° C. for 2 hours with gentle shaking. Cells were pelleted and resuspended in 100 µl YEP-medium. Finally, transformed bacteria were selected on YEP-agar plates containing 25 mg/l kanamycin. The presence of pA33.236 was tested by restriction enzyme analysis.

*A. tumefaciens* cells, transformed with pA33.236 were grown at 30° C. in 5 ml LB medium, containing 50 µg/ml kanamycin and 100 µg/ml rifampicin. After 48 h of growth, the cells were washed twice in 5 ml 2 mM MgSO$_4$, then suspended in 5 ml MS medium. Stem internodes were incubated in 20 ml of a diluted (100× in MS) *A. tumefaciens* suspension, and gently shaken for 30 min. After incubation, the stem internodes were blotted dry on filter paper and placed on top of PCM-agar plates (48 h at 21° C.). Callus formation was induced by transferring the internodes to PCM agar plates, containing 200 mg/l cefotaxime and 100 mg/l kanamycine (96 h at 21° C.). Shoot formation was induced at 21° C. by transferring the stem internodes to PSM-agar, containing 200 mg/l cefotaxime and 100 mg/l kanamycin. Regenerating explants were transferred to fresh medium every three weeks. Root formation was induced by transferring the transgenic shoots to MS 30 medium, containing 200 mg/l cefotaxime and 50 mg/l kanamycine. Rooted plantlets of 5–10 cm were transferred to the greenhouse.

DNA and RNA Analysis of Jerusalem Artichoke

Total DNA was isolated from mature young mature leaves which were harvested 3 months after transfer of the plants to the greenhouse. Aliquots of the DNA was digested with a number of restriction enzymes. Total RNA was isolated from stolons, tubers of various ages, stems, leaves and flower tissues. After electrophoresis on 1% agarose, DNA or RNA was blotted onto Hybond-N+ (Amersham) and UV crosslinked. Filters were hybridised with either an fft111, sst103 (see Construction and screening of a cDNA library from *H. tuberosus*) or an a33 probe. A 1140 bp DNA fragment specific for a33 was synthesised by PCR using primers 5'-CAACCCAATTCTCTTCCCTCCTCCG-3' and 5'-ACAAACACTITGGGCGGC-3' and plasmid pA33 (a33 cDNA in pBluescript) as a template. The gene specific DNA fragments were radio labelled with alpha $^{32}$P-ATP using the RadPrime kit (Life Technologies). Hybridisation was at 65° C. in 500 mM NaP-buffer, pH 7.2, 7% SDS, 1% BSA, 1 mM EDTA. Filters were washed to a final stringency of 0.1×SSC, 0.1% SDS at 65° C. (2×15 min) and finally exposed to X-omat AR (Kodak).

Transformation of Sugar Beet

Transgenic sugar beets (*Beta vulgaris*) were generated by a stomatal guard cell based transformation system (Hall et. al. 1996). Guard cell protoplasts were obtained from shoot cultures of the diploid breeding line Bv-NF (Hall et. al. 1996). One million guard cell protoplasts were transformed with 50 µg of the plasmid in the presence of PEG. Regeneration and selection of transformants was as described (Hall et. al. 1996). Plants were grown in a greenhouse at 18/15° C. (day/night) under a 16 h photoperiod. Two months old leaves were cut to prevent spread with powdery mildew.

DNA and RNA Analysis of Transgenic Plants

Total DNA was isolated from young mature leaves which were harvested 3 months after transfer of the plants to the greenhouse. DNA was digested with specific restriction enzymes. Total RNA was isolated from 2–5 month old tap roots or tubers. After electrophoresis on 1% agarose, DNA or RNA was blotted onto Hybond-N+(Amersham) and UV cross-linked. Filters were hybridised with a gene specific probe. The DNA fragment was radio labelled with alpha $^{32}$P-ATP using the RadPrime kit (Life Technologies). Hybridisation was at 65° C. in 500 mM NaP-buffer, pH 7.2, 7% SDS, 1% BSA, 1 mM EDTA. Filters were washed to a final stringency of 0.1×SSC, 0.1% SDS at 65° C. (2×15 min) and finally exposed to X-omat AR (Kodak).

Enzyme Activity: Protein Extraction and Assay

Leaf and root tissues were ground in liquid nitrogen to a fine powder. Five hundred mg of the powdered tissue were extracted in 1 ml 50 mM BisTris pH 5.5, 1 mM EDTA, 1 mM MgSO$_4$, 1 mM DTT, 1 mM PMSF, 20 mM Na-metabisulfite and 15 g l$^{-1}$ PVPP. The extract was centrifuged (20 min at 10000×g) and the supernatant desalted and concentrated by centrifugation through Centriprep 30 ultrafiltration devices (Amicon, Breda, The Netherlands). A 240 µl aliquot was mixed with 240 µl assay mixture, containing either 100 mM sucrose, GF$_2$ or GF$_3$ in 20 mM BisTris pH 5.5, 2 mM DTT and 0.01% Na-azide t(w/v). After 8, 16 and 24h of incubation, an aliquot of the reaction mixture was boiled for 5 min and store at –20° C. The assay mixtures were then analysed by HPAEC as described below.

Analysis of Sugars and Inulin by TLC and HPAEC

The inulin composition of transgenic plants beet was measured by TLC (Thin Layer Chromatography) and HPAEC (High Performance Anion Exchange Chromatography). Two to five months after transfer of the plants to the greenhouse, fresh plant material (500 mg) was collected and cut into 2 mm thick slices with a sterile razor blade. A 20 mM phosphate buffer, pH 7.0, of 100° C. was added to the slices to a final volume of 3 ml, and kept at 85° C. for 30 min, with occasional vortexing. The extract was centrifuged at 14000 rpm and the supernatant collected. TLC analysis was performed on silica gel G (Schleicher and Schuell Nederland BV, The Netherlands) developed two times in a mixture of 1-butanol:2-propanol:water 3:12:4. Carbohydrates were stained with a fructose-specific urea phosphoric spray (Wise et al., 1955). For HPAEC analysis, the extracts were deionized with a mixture of equal amounts of Q-sepharose and S-sepharose Fast Flow (Pharmacia, Upssala, Sweden), which were pre-equilibrated in 20 mM phosphate buffer, pH 7.0. The ion exchanger was added to 50% of the total extract volume, mixed for 5 min at 600 rpm, then centrifuged at 14000 rpm for 2 min. The supernatant was analysed by High Pressure Anion Exchange Chromatography/Pulsed Amperometric Detection (HPAEC-PAD, Dionex, The Netherlands) equipped with 250×4 mm CarboPac PA1 anion exchange column and a 25×3 mm CarboPac PA guard column. Inulins were separated with a 80 min linear gradient of 0 to 0.4 mol m$^{-3}$ NaAc in 0.1 mol m$^{-3}$ NaOH at a flow rate of 1 ml min$^{-1}$, or over 85 minutes with an aqueous gradient (A: NaOH 0.1 mol m$^{-3}$; B: (0.1 mol m$^{-3}$ NaOH+0.4 mol m$^{-3}$ NaAc); C: NaOH 1 mol m$^{-3}$) as follows: min 0–5: A:B 96:4; min 5–15 linear gradient A:B from 96:4 to 60:40; min 15–35: linear gradient A:B from 60:40 to 30:70; min 35–50 linear gradient A:B from 30:70 to 10:90; min 50–60 linear gradient A:B from 10:90 to 0:100; min 60–85 A:B 0:100; followed by regeneration min 0–5 with A:B:C: 0:0:100 and min 5–30 with A:B 96:4, at a flow rate of 1 ml min$^{-1}$. Standard grade inulin was used as a standard. CGC analysis was made according to the method described by L. De Leenheer et al., Starch-Stärke, (1994), Vol. 46, p. 193–196.

EXAMPLES

Example 1

Isolation of a New cDNA from the cDNA Library of *Helianthus tuberosus* Homologous to sst103 and fft111 from *Helianthus tuberosus*

An Uni-ZAP cDNA library, constructed from mRNA isolated from *H. tuberosus* tubers, was screened with a mixture of a 840 bp sst103 and a 860 bp fft111 fragment. The sst103 specific fragment was obtained by PCR using primers 5'-TGTCAGCCCATCCCTTGGAAAGG-3' and 5'-TACGCTGTCAACTCGTCGG-3' and pSST103 (Van der Meer et al., 1998) as template. The fft111 specific fragment was obtained by PCR using 5'-GTTCAACGCTGCTTGATCCACC-3' and 5'-ACCACGGTCCTTCCAAACGG-3' and pFFT111 (Van der Meer et al, 1998) as template. Screening of about 100.000 cDNA clones yielded about 1200 positive clones, most of them most probably representing either a sst103 or a fft111 cDNA. Only the lambda ZAP clones giving a weak positive signal (84) were picked from the primary screening. After 34 rounds of purification, 11 clones were left. From these clones, the pBluescript phagemids were excised from the uni-ZAP vector and the cloned insert characterised by restriction enzyme analysis and sequencing. One clone with an about 2 kb insert, designated a33, was fully sequenced. The DNA sequence of a33 (Sequence ID. No.1) and the corresponding amino acid sequence (Sequence ID. No. 2) is presented in FIG. 1. Sequence ID. No. 1, designated a33 has an open reading frame of 1845 base pairs and encodes a protein of 615 amino acid residues (Sequence ID. No. 2). On DNA level, a33 shows a 70% identity with the 1-SST encoding sst103 cDNA sequence from *H. tuberosus* and 54% identity with the 1-FFT encoding, fft111 cDNA sequence from *H. tuberosus*. At the amino acid level, a33 shows a 75% similarity with sst103 from *H. tuberosus* and a 58% similarity with fft111 from *H. tuberosus*.

Example 2

Isolation of a New cDNA from the cDNA Library of *Cichorium intybus*Homologous to sst103 and fft111 from *Helianthus tuberosus*

A Lambda TriplEx cDNA library, constructed from mRNA isolated from the tap roots of *C. intybus*, was screened with a mixture of a 840 bp sst103 and a 860 bp fft111 fragment (see example 1). The primary screening of about 60.000 cDNA clones yielded about 700 positive clones, of which 96 clones were picked. After 3–4 rounds of purification 81 clones were left. From 55 clones, the pTriplEx phagemids were excised from lambda Trip1Ex vector and the cloned insert characterised by restriction enzyme analysis and sequencing. The DNA sequence of one of the clones, designated c86b (Sequence ID. No. 3) and the corresponding amino acid sequence (Sequence ID. No. 4) is presented in FIG. 2A. Sequence ID. No. 3, designated c86b, has an open reading frame of 1851 base pairs and encodes a protein of 617 amino acid residues (Sequence ID. No. 4). On DNA level, c86b shows a 61% identity with sst103 from *H. tuberosus* and 77% identity with fft111 from *H. tuberosus*. At the amino acid level, c86b shows a 53% similarity with sst103 from *H. tuberosus* and a 78% similarity with fft111 from *H. tuberosus*. The DNA sequence of another clone, designated c33 (Sequence ID. No. 5) and the corresponding amnino acid sequence (Sequence ID. No. 6) is presented in FIG. 2B. Sequence ID. No. 5 designated c33, has an open reading frame of 1920 base pairs and encodes a protein of 640 amino acid residues (Sequence ID. No. 6). On DNA level, c33 shows a 97% identity with 1-SST from chicory (Genbank accession no U81520). On amino acid level c33 shows a 88% /(similarity with 1-SST from chicory (Genbank no U81520).

Example 3

Analysis of Genomic Organisation and Expression of a33 in *Helianthus tuberosus*

Figure 3:
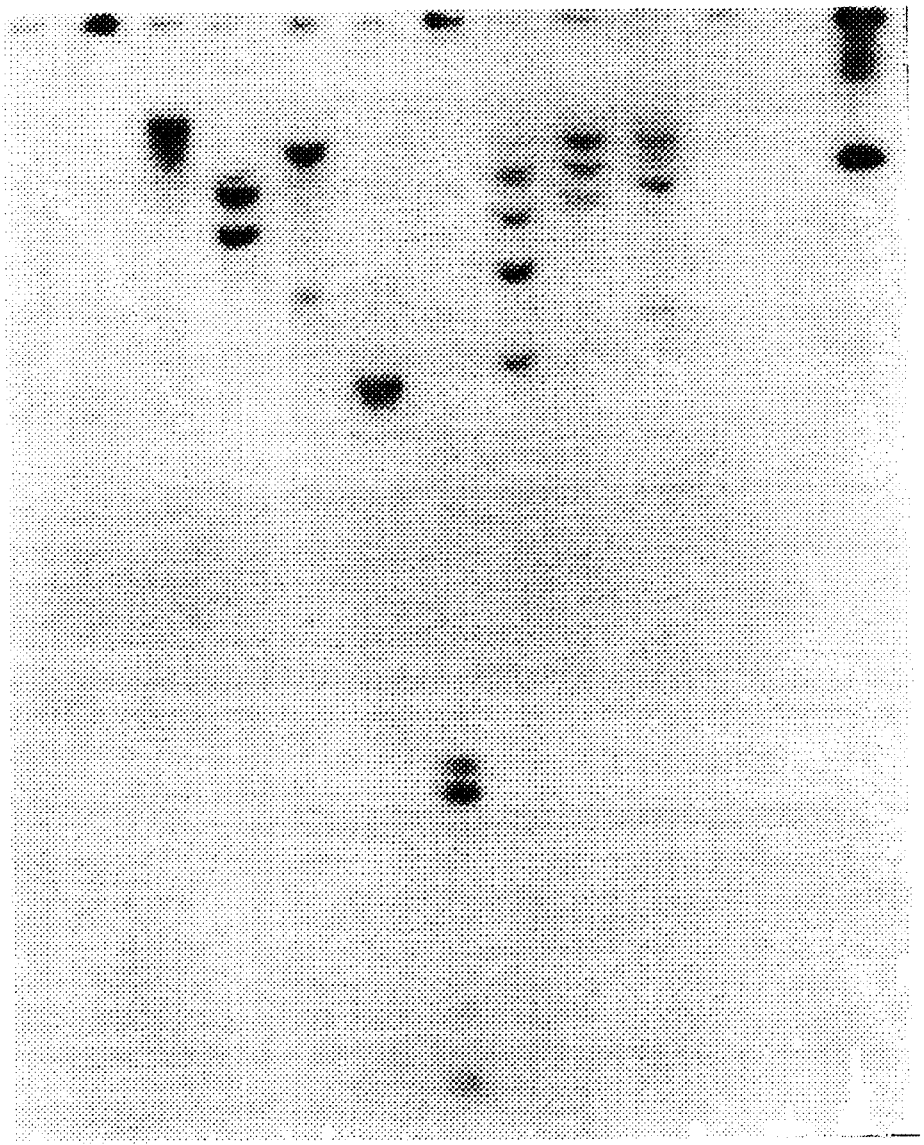
FIG. 3: depicts a Southern blot analysis of *Helianthus tuberosus* genomic DNA probed with an a33 PCR fragment. *H. tuberosus* DNA was digested with EcoR1, EcoR5, XbaI, AflIII, DraI, NdeI, HincII and, XhoI. Plasmid pA33 (the a33 cDNA in the pBluescript vector) was used as a positive control, potato DNA digested with EcoRI was used as negative control.

To estimate the number of a33 genes present in the Jerusalem artichoke genome, Southern blot analysis of digested *H. tuberosus* DNA was performed, using a radio labelled a33 fragment of 1140 bp as a probe. (Plant Journal 15, 489–500). Under stringent conditions (hybridisation at 65° C. and washing at 65° C., 0.1×SSC, 0.1% SDS), only one, maybe two fragments of the AflII digest hybridises to the a33 probe (FIG. 3), suggesting that only one, maybe two a33 genes are present in the Jerusalem artichoke genome.

Transcript levels o a33, sst103 and fft111 were studied in different organs and different developmental stages of the tubers of Jerusalem artichoke (FIG. 4). In correspondence to earlier experiments (Van der Meer 1998), data in FIG. 4A shows that sst103 is highly expressed in tubers, and to a less extent in fibrous roots, flowers and receptacle. The expression pattern of fft111 (FIG. 4B) resembles that of sst103, although in general the expression of fft111 is 3–10 times lower than that of sst103. In contrast to sst103 and fft111, a33 is not expressed to a measurable level in any of the tested tissues (FIG. 4C). To quantify the a33, sst103 and fft111 expressing in tubers, 100.000 plaques of the cDNA library of Jerusalem artichoke tubers were blotted onto Hybond filters, hybridised to either an a33, sst103 or fft111 probe at 65° C., then washed at high stringency (65° C., 0.1×SSC, 0.1% SDS). Expression levels of a33, sst103 or fft111 in tubers were 0.001, 1 and 0.2%, respectively. If a33 encodes a functional fructosyltransferase protein, it does not effectively contribute to inulin synthesis in tubers of Jerusalem artichoke. From a functional point of view, a33 can be considered as a silent gene.

Example 4

Construction of a Chimeric a33 Gene Construct for Transformation into Potato

Figure 5:
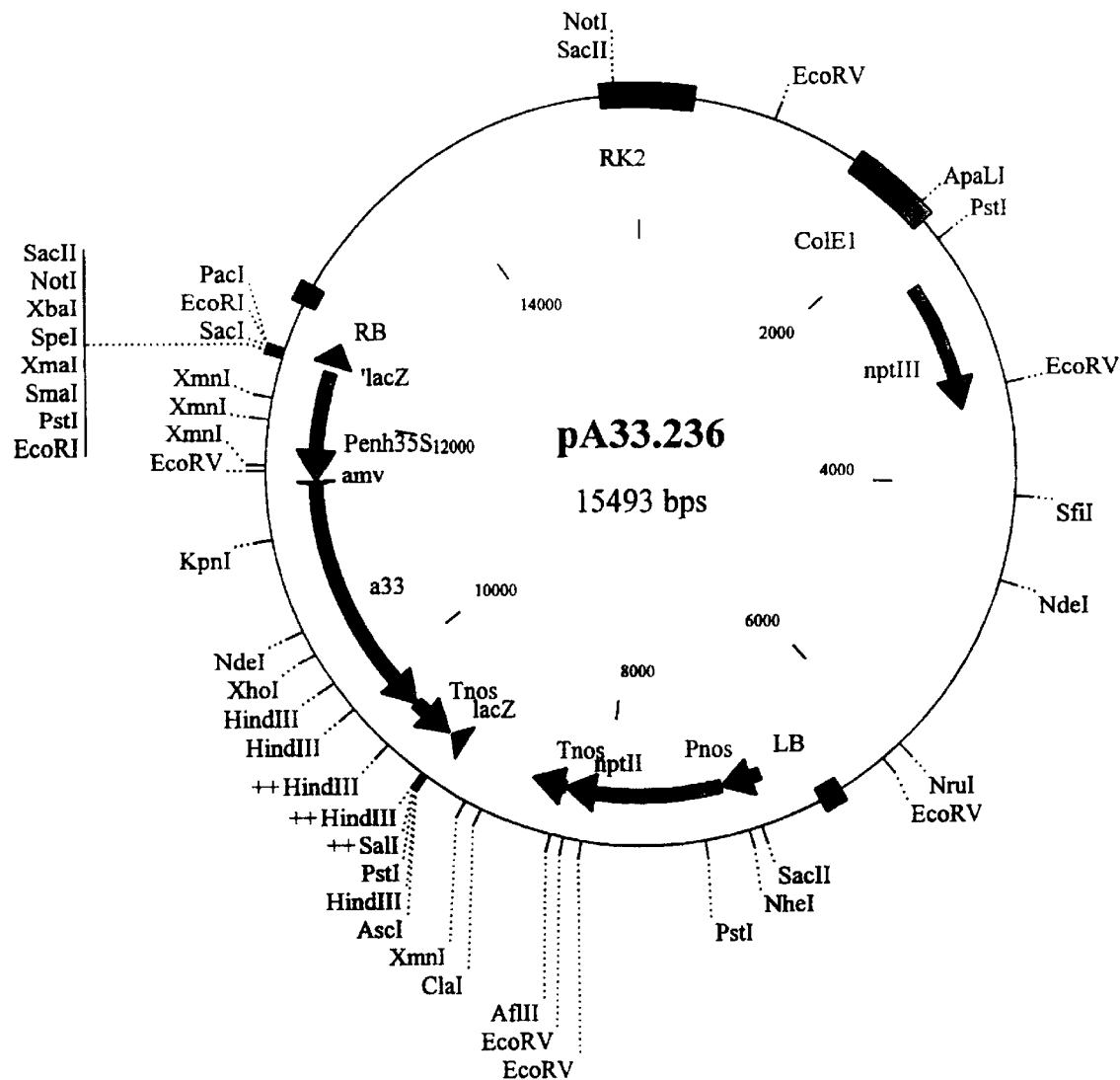
FIG. 5: presents the chimeric gene construct pA33.236 consisting of the enhanced CaMV35S promoter (Penh35S)

By PCR, using primers 5'-ATCAACATGTCTTCCACCCC-3' and 5'-TGGATCCTCAAGGCCGCCCTC-3', an AflIII site was introduced at the first ATG (start of the open reading frame) and a BamHI site was introduced down-stream of the stop codon of the full length a33 cDNA clone (pA33), isolated from Jerusalem artichoke. The newly obtained a33 PCR fragment was cloned into pMOSblue (Amersham Life Science) yielding pMOSA33.10. From the plasmid pFFT405 (see further, for a complete description), which contains the enhanced Cauliflower Mosaic Virus 35S promoter (enh35S), Alfalfa Mosaic Virus RNA4 leader sequence (amv), cDNA fft111 from Jerusalem Artichoke and the nos terminator sequence (Tnos), the complete fft111 sequence was replaced by the a33 PCR fragment. The complete a33 PCR fragment, resulting from a digestion of pMOSA33.10 with AflIII and BamHI (partial), was ligated into pFFT405, from which the fft111 was removed by a digestion with NcoI and BamHI (partial). Replacing the fft111 cDNA in pFFT405 with the a33 PCR fragment yielded pA33.102. The enh35S-amv-a33-Tnos-fragment was cut from pA33.102 with SacI and SalI, and ligated into the plant transformation vector pBINPLUS (Van Engelen et al., 1995) digested with SacI/SalI, which resulted in pA33.236 (FIG. 5).

pFFT 405 was obtained by cloning the Penh35S-amv-fft111-Tnos-fragment cut from pFFT209 (Van der Meer et al., 1998), with EcoRI (partial digest) and HindIII into pBluescript SK+ (Stratagene, USA) cut with EcoRI/HindIII.

Example 5

Analysis of Transgenic Plants Expressing the a33 Gene

About 25 transgenic potato plants were generated harbouring the pA33.236 construct. Ten potato plants were transformed with the Agrobacterium strain AGL0 lacking a binary vector. These plants were used as a control. Southern blot analysis of genomic DNA isolated from 22 transformed plants showed that 17 plants has integrated into their genome less than 3 copies of the introduced chimeric gene (data not shown). Plant numbers 23, 27B, 74, 84 and 93 had integrated one copy. Northern analysis showed that a33 was highly expressed in plants numbers 27B, 74 and 93, and less, but still clearly expressed in plant numbers 23 and 84.

The carbohydrate composition of the a33 harbouring plants was analysed by two essentially different techniques: thin layer chromatography (TLC) and high pressure anion exchange chromatography (HPAEC). Analysis of leaf extracts from the potato harbouring the pA33.26 construct showed that plant numbers 23, 27B, 50, 83 and 93 accumulate a range of fructose containing compounds in leaves and tubers (FIG. 6). A comparison with the inulin standard extracted from Jerusalem Artichoke, containing inulins up to a DP of 30, shows that the tuber extracts accumulate inulins up to a degree of polymerisation of at least 10 (FIG. 6), whereas the leaves accumulate inulins with a DP of 3, 4 and 5.

The presence of inulins in leaf extract and tuber extracts of the a33-harbouring plants is confirmed through HPAEC analysis. HPAEC indicates that plant numbers 23, 27B, 93 (only 93 is shown in FIG. 7) accumulate inulins up to a degree of polymerisation of 11. This clearly indicates that a33 encodes a fructosyltransferase enzyme, able to synthesise inulins up to a DP of at least 11. Since the a33 encodes an enzyme that can catalyse all steps required for inulin synthesis, including reaction (1), the conversion of sucrose into GEF, the a33 encoded enzyme (A33) belongs to the group of SST encoding genes.

Example 6

Construction of a Chimeric a33 Gene Construct for Transformation into Sugar

The complete chimeric a33 gene (Penh35S-amv-a33-Tnos) was cut from pA33.102 with NotI and SalI and ligated into pUCM2, digested with NotI/SalI, resulting in pUCA33.1. Plasmid pUCM2 is derived from the cloning vector pUCAP (Van Engelen et al. 1995).

To construct plasmid pUCM2 the multiple-cloning-site of plasmid pUCAP was modified by the insertion of two adapters. First, adapter 5'-TCGACCATATCGATGCATG-3'/ 5'-CATCGCTATTGG-3', containing the restriction sites SalI/ClaI/SphI, was cloned in the pUCAP plasmid digested with SahI/SphI. This resulted in plasmid pUCM1. Next, adapter 5'-TAAGCGGCCGCAGATCTGG-3'/5'-AATTCCAGATCTGCGGCCGCTTAAT-3', consisting of PacI/NotI/BglII/EcoRI restriction sites, was cloned in plasmid pUCM1 digested with PacI/EcoRI. This resulted in plasmid pUCM2. The complete chimeric a33 gene (Penh35S-amv-a33-Tnos) was cut from pUCA33.1 with NotI and AscI and ligated into pUCPAT 34 digested with NotI/AscI, yielding pUCPA33.342 (FIG. 8). pUCPA33.342 was used to transform guard cell protoplasts of sugar beet.

Example 7

Construction of a Chimeric a33-c86b Gene for Transformation into Sugar Beet

The complete chimeric C86B gene (Penh35S-amv-c86b-Tnos), which was cut from pC86B.2 with EcoRI and ClaI, and cloned into pUCPAT.34 (see example 8), was digested with EcoR1 (partial digest) and ClaI. This resulted in pUCPC86B.342. The NotI/AscI fragment of pUCA33.1, containing the full length A33-cDNA (a33) was ligated into pUCPC86B.342 cut with NotI/AscI, yielding pUCPCA342.25. (FIG. 9). pUCPCA342.25 was used to transform guard cell protoplasts of sugar beet.

Example 8

Construction of a Chimeric sst103-fft111 Gene for Transformation into Sugar Beet The pat gene, encoding phosphinotricin acetyl transferase (AgrEvo, Berlin, Germany), which confers bialaphos resistance, was cut from pIGPD7 (Hall et al., 1996) with EcoR1 and ligated into pUCM3, digested with EcoRI, which yielded pUCPAT34.

To construct plasmid pUCM3, plasmid pUCAP was digested with PacI/AscI and the whole multiple-cloning-site was replaced by adapter 5'-TAA GGGGTACCACCATC-GATACCGAATTCTACATGCATGCATGGAGATCTC-CCAAGCTTCTAAGATGCGGCCGCTAAACATGG-3'/ 5'-CGCGCCATGTTTAGCGGCCGCATCTTAGAAGCTT GGGAGATCTCCATGCATGCATGTAGAATTCGGTAT CGATGGTGGTACCCCTTAAT-3' The complete chimeric sst103 gene (Penh35S-amv-sst103-Tnos) was cut from pSST403 (Van der Meer et al., 1998) with EcoRI and ClaI and ligated into pUCM1, digested with EcoRI/ClaI, which resulted in pUCST21.

The complete chimeric fft111 gene (Penh35S-amv-fft111-Tnos) cut from pFFT405 with NotI and ClaI was ligated into pUCM2, cut with NotI/ClaI, resulting in pUCFT21. The complete chimeric sst103 gene was cut from pUCST21 with PacI and ClaI and introduced into pUCPAT34, digested with PacI/ClaI, yielding pUCPS34.4. The complete chimeric fft111 gene was cut from pUCFT21 with NotI and AscI and ligated into pUCPS34.4, digested with NotI/AscI, yielding pUCPSF344.18 (FIG. 10). pUCPSF 344.18 was used to transform guard cell protoplasts of sugar beet.

Example 9

Construction of a Chimeric sst103-c86b Gene for Transformation into Sugar Beet

Using PCR and primer 5'-CCTCGAACCATGGAAACAGC-3' an NcoI was introduced at the first ATG (start of the open reading frame) of the full length c86b cDNA clone. A BamHI site was introduced downstream of the stop codon of c86b, using primer 5'-TAATAAAAGAGGATCCTCATGAAACG-3'. This c86b PCR fragment (1895 bp) was cloned into pCR-Script Amp SK(+) (Stratagene, USA) yielding p86BpCRscp. From the plasmid pFFT405, which contains the enhanced Cauliflower Mosaic Virus 35S promoter (Penh35S), Alfalfa Mosaic Virus RNA4 leader sequence (amv), fft111 cDNA clone from Jerusalem Artichoke and the nos terminator sequence (Tnos), the complete fft111 sequence was replaced by the c86B PCR fragment. The c86B fragment, cut from p86BpCRscp with NcoI and BamHI, was ligated into pFFT405 cut with NcoI and BamHI, yielding pC86B2. The NotI/ClaI fragment of pC86B2 (enh35S-amv-sst103-Tnos) was cloned into pUCM2 cut with NotI/ClaI, yielding pUC86B2. The NotI/AscI fragment of pUC86B2 was cloned into the pUCPS344 digested with NotI/AscI, resulting in pUCPSC344.25 (FIG. 11). pUCPSC344.25 was used to transform guard cell protoplasts of sugar beet.

Example 10

Construction of a Chimeric a33-fft111 Gene for Transformation into Sugar Beet

From the plasmid pUCPA33.342, the complete recombinant a33 gene (Penh35S-amv-sst103-Tnos) and the complete pat cassette were excised with ClaI, then introduced into pUCFT21 cut with ClaI, yielding pUCPAF21.17 (FIG. 12)

Example 11

Analysis of Sugar Beet plants Comprising the pUCPSF344.18 Plasmid

Two fructosyltransferase encoding cDNAs from *H. tuberosus* (sst 103 and fft111), and the pat gene conferring bialaphos resistance were cloned into the pUCM3 vector.

The resulting plasmid pUCPSF344.18 (FIG. 10) was used to transform stomatal guard cell protoplasts of sugar beet.

Bialophos-resistent calli were obtained after bialophos selection. Regeneration and selection of transformants was as described (Hall et al. 1996). Transgenic sugar beets were analyzed by Northern analysis (FIG. 13): as the sst103 probe a DNA fragment was used which was prepared by PCR using primers 5'-TTGAATAGAACATCGGGCTCTAGCG-3' and 5'-TACGCTGTCAACTCGTCGG-3' and plasmid pUCFT21 (example 8) as a template; as the fft111 probe a DNA fragment was used which was prepared by PCR using primers 5'-GTTCAACGCTGCTGGATCCACC-3' and 5'-ACCACGGTCCTTCCAAACGG-3' and plasmid pUCFT21 (example 8) as a template. Line 7PSF22 expressed both the sst103 and the fft111 gene (FIG. 13, lane 1). This line was further analyzed by HPAEC. The inulin profile can be described as a mixture of inulin molecules up to a DP of 9 (FIG. 14). The inulin profile of sugar beet line 7PSF22 is essentially different from the inulin profile of transgenic sugar beet lines comprising only the sst103 gene (Sevenier et al. 1998). The sugar beet comprising only the sst103 gene accumulates inulins up to a DP of 5 ($GF_2$, $GF_3$ and $GF_4$; Sevenier et al. 1998). The inulin profile of line 7PSF22 is also different from the standard grade inulin from chicory (FIG. 15), which comprises of a mixture of inulins up to a DP of about 55.

Example 12

Analysis of Sugar Beet Plants Comprising the pUCPSC 344.14 Plasmid

The plasmid prepared according to the description in example 9, was used to transform stomatal guard cell protoplasts of sugar beet. Bialophos-resistent calli were obtained after bialophos selection. Regeneration and selection of transformants was as described (Hall et al. 1996). Transgenic sugar beets were analysed by Northern analysis (FIG. 13): as a c86b probe a DNA fragment was used, which was prepared by PCR using primers 5'-GTGACCTTGAGGATGCATCC-3' and 5'-TCGGTTGCACCCGCGCTCG-3' and plasmid pUC86B2 (example 9) as a template.

Line 9PSC2, expressing both the sst103 and the c86b gene (FIG. 13, lane 2), was selected for further analysis by HPAEC. The inulin profile of sugar beet line 9PSC2 can be described as a polydisperse mixture of inulin molecules with a DP ranging from 3 to 15 (FIG. 16). The inulin profile of sugar beet line 9PSC2 is essentially different from transgenic sugar beet lines comprising only the sst103 gene (Sevenier et al. 1998), but also from line 7PSF22 comprising a combination of sst103 and fft111, which accumulate inulin molecules up to a DP of 9 (FIG. 14). The inulin profile of line 9PSC2 is also different from the standard grade inulin from chicory (FIG. 15), which comprises of inulins up to a DP of about 55.

Example 13

Analysis of Sugar Beet Plants Comprising the pUCPAF21.17 Plasmid

The plasmid prepared according to the description in example 10, was used to transform stomatal guard cell protoplasts of sugar beet. Bialophos-resistent calli were obtained after bialophos selection. Regeneration and selection of transformants was as described (Hall et al. 1996). Transgenic sugar beets were analysed by Northern analysis: as the a33 probe a DNA fragment was used, which was prepared by PCR using primers 5'-CAACCCAATTCTCTTCCCTCCTCCG-3' and 5'-ACAAACACTTTCGGCCGCC-3' and plasmid pUCA33.1 (example 6) as a template. Lines 8PAF1 and 8PAF5 which were expressing both the a33 and the fft111 gene (FIG. 13, lanes 3 and 4, respectively), were analysed by HPAEC. Sugar beet line 8PAF5 accumulates a inuline molecules ranging from DP 3–22 (FIG. 17). Sugar beet line 8PAF1 accumulates a mixture of inulin molecules with a DP ranging from 3 to 26 (FIG. 18). In contrast to lines 7PSF22 (example 11), 9PSC2 (example 12) and 8PAF5 (example 13), in which $GF_2$ is invariably the most abundant inulin molecule, in line 8PAF1, the concentrations of $GF_2$, $GF_3$, $GF_4$ and $GF_5$ are in the same range, being 2.5. 2.5. 2.4 and 2.2% of total dry matter, respectively. Surprisingly, line 8PAF1 also accumulates significant amounts of $F_2$, $F_3$, $F_4$, $F_5$, $F_6$, $F_7$, $F_8$ and $F_9$, being 0.4, 0.4, 0.5, 0.4, 0.4, 0.3, 0.2, 0.1% of total dry weight, respectively (CGC-analysis results).

The inulin profiles of sugar beet lines 8PAF1 and 8PAF5 are essentially different from from sugar line 7PSF22 comprising a combination of sst103 and fft11, which accumulate inuline molecules up to a DP of only 9. The inulin profile of lines 8PAF1 and 8PAF5 are also different from the standard grade inulin from chicory (FIG. 15), which comprises of inulins up to a DP of about 55.

REFERENCES

Ausubel F M, Brent R, Kingston R E, Moore D D, Seidman J G, Smith J A, and Struhl K. (1994) Current protocols in molecular biology. John Wiley & Sons.

Hall, R. D., Riksen-Bruinsma, T., Weyens, G. J., Rosquin, I. J., Denys, P. N., Evans, I. J., Lathouwers, J. E., Lefebvre, M. P., Dunwell, J. M., van Tunen, A. J., and Krens, F. A. (1996). A high efficiency technique for the generation of transgenic sugar beets from stomatal guard cells. *Nature Biotechnology* 14, 1133–1138.

Koops A J and Jonker H H. (1994). Purification and characterisation of the enzymes of fructan biosynthesis in tubers of *Helianthus tuberosus* 'Colombia'. I. Fructan-:fructan fructosyltransferase. Journal of Experimental Botany 45, 1623–1631

Koops A J and Jonker H H. (1996). Purification and characterisation of the enzymes of fructan biosynthesis in tubers of *Helianthus tuberosus* 'Colombia'. II. Purification of sucrose:sucrose 1-fructosyltransferase and reconstitution of fructan synthesis in vitro with purified sucrose:sucrose 1-fructosyltransferase and fructan:fructan 1-fructosyltransferase. Plant Physiology, in press.

De Leenheer, L (1996). Production and use of inulin, in: Carbohydrates as Organic Raw Materials, Vol. III, p. 67–92.

Sambrook J, Fritsch E F, Maniatis T. (1989) Molecular cloning. A laboratory manual. Cold Spring Harbor Laboratory Press, Cold Spring Harbor.

Van Engelen F A, Molthoff J W, Conner, A J, Nap J-P, Pereira A, and Stiekema W J. (1995). pBINPLUS: an improved plant transformation vector based on pBIN19. Transgenic Research 4,288–290.

Van der Meer I M, Koops A J, Hakkert J C and Van Tunen A J (1998). Cloning of Fructan Biosynthesis genes of Jerusalem Artichoke. Plant Journal 1998.

Vijn L, Van Dijken A, Sprenge N, Van Dun K, Weisbeek P. Wiernken A and Smeekens S (1997). Fructan of the inuline Neoseries is synthesized in transgenic chicory plants (*Cichorium intybus* L.) harbouring onion (*Allium cepa* L.) fructan:fructan 6G-fructosyltransferase. Plant J. 11, 387–398.

Visser R G F. (1991). Regeneration and transformation of potato by *Agrobacterium tumefaciens*. In: *Plant Tissue Culture Manual* B5, ed. Lindsey, K. Dordrecht, The Netherlands, Kluwer Academic Publishers, pp. 1–9.

Wise C S, Dimler R J, Davis H A, Rist C E. (1955). Determination of easily hydrolysable fructose units in dextran preparations. Anal. Chem. 27, 33–6.

Sevenier R., Hall R. D., van der Meer I. M., Hakkert H. J. C., van Tunen A. J. and Koops A. J., 1998. High level fructan accumulation in a transgenic sugar beet. Nature Biotechnology 16: 843–846.

What is claimed is:

1. An a33 1-SST enzyme encoding cDNA sequence according to SEQ ID NO: 1.

2. A recombinant DNA construct, recombinant gene or vector comprising the cDNA sequence according to SEQ ID NO: 1.

3. A recombinant DNA construct, recombinant gene or vector comprising more than one copy of the cDNA sequence according to SEQ ID NO: 1.

4. A method for producing a transgenic plant with a modified inulin producing profile comprising in its genome a combination of a 1-SST (sucrose:sucrose 1-fructosyl-transferase) enzyme encoding gene and a 1-FFT (fructan:fructan 1-fructosyl-transferase) enzyme encoding gene, said method comprising transforming an inulin producing host plant comprising in its genome a combination of a 1-SST enzyme encoding gene and a 1-FFT enzyme encoding gene, by insertion of a recombinant gene containing the 1-SST enzyme encoding a33 cDNA sequence according to SEQ ID NO: 1 into the genome of the host plant and wherein said 1-SST enzyme encoding gene, said 1-FFT enzyme encoding gene and said recombinant gene containing the 1-SST enzyme encoding a33 cDNA sequence according to SEQ ID NO: 1, are respectively operably linked to a promoter sequence, a terminator sequence and optionally to a DNA sequence encoding a targeting signal or a transit peptide, all active in said host plant.

5. The method according to claim 4, wherein the recombinant gene comprises more than one copy of the cDNA sequence according to SEQ ID NO: 1.

6. A method for producing a transgenic plant with a modified inulin producing profile comprising in its genome a combination of a recombinant 1-SST enzyme encoding gene comprising the 1-SST enzyme encoding a33 cDNA sequence according to SEQ ID NO: 1, and a recombinant 1-FFT enzyme encoding gene, said method comprising transforming a non-inulin producing host plant by insertion into the genome of the host plant of a recombinant 1-SST enzyme encoding gene comprising the 1-SST enzyme encoding a33 cDNA sequence according to SEQ ID NO: 1 and of a recombinant 1-FFT enzyme encoding gene, wherein the recombinant 1-SST enzyme encoding gene and the recombinant 1-FFT enzyme encoding gene are respectively operably linked to a promoter sequence, a terminator sequence and optionally a DNA sequence encoding a targeting signal or a transit peptide, all active in said host plant.

7. The method according to claim 6, wherein the recombinant 1-SST enzyme encoding gene comprises more than one copy of the cDNA sequence according to SEQ ID NO: 1.

8. The method according to claim 6 wherein the 1-FFT enzyme encoding DNA sequence of the recombinant 1-FFT enzyme encoding gene originates from a plant of the plant family of the Asteraceae (Compositae).

9. The method according to claim 6 wherein the recombinant 1-FFT enzyme encoding gene comprises at least one 1-FFT enzyme encoding c86b cDNA sequence according to SEQ ID NO: 3.

10. A method for producing a transgenic plant with a modified inulin producing profile comprising in its genome a recombinant gene containing the a33 cDNA sequence according to SEQ ID NO: 1 coding for an enzyme which acts as a 1-SST enzyme as well as a 1-FFT enzyme, said method comprising transforming a host plant which is free of 1-FFT enzyme encoding genes by insertion into the genome of the host plant of a recombinant gene containing the a33 cDNA sequence according to SEQ ID NO: 1 which is operably linked to a promoter sequence, a terminator sequence and optionally a DNA sequence encoding a targeting signal or a transit peptide, all active in said host plant.

11. The method according to claim 10, wherein the host plant comprises in its genome already a 1-SST enzyme encoding gene which is operably linked to a promoter sequence, a terminator sequence and optionally a DNA sequence encoding a targeting signal or a transit peptide, all active in said host plant.

12. The method according to claim 4 wherein the host plant is selected from the group consisting of wheat, barley, chicory, banana, and Jerusalem artichoke.

13. The method according to claim 6 wherein the host plant is selected from the group consisting of corn, rice, sorghum, millets, sunflower, cassava, canola, soybean, oil palm, groundnut, cotton, sugar cane, bean, pea, cowpea, tomato, beet, sugar beet, tobacco, potato, sweet potato, coffee, cocoa and tea.

14. The method according to claim 10 wherein the host plant is selected from the group consisting of corn, rice, sorghum, millets, sunflower, cassava, canola, soybean, oil palm, groundnut, cotton, sugar cane, bean, pea, cowpea, tomato, beet, sugar beet, tobacco, potato, sweet potato, coffee, cocoa and tea.

15. The method according to claim 4 wherein inulin produced by the trangenic plant comprises fructo-oligosaccharides.

16. The method according to claim 6 wherein the inulin produced by the transgenic plant comprises fructo-oligosaccharides.

17. The method according to claim 10 wherein the inulin produced by the transgenic plant comprises fructo-oligosaccharides.

18. The method according to claim 4 wherein the inulin produced by the transgenic plant has an average degree of polymerization of at least 10.

19. The method according to claim 6 wherein the inulin produced by the transgenic plant has an average degree of polymerization of at least 10.

20. The method according to claim 4 wherein said method comprises the subsequent steps of
(i) preparing a recombinant 1-SST gene construct comprising the 1-SST enzyme encoding cDNA sequence according to SEQ ID NO: 1, operably linked to a promoter sequence, a terminator sequence, and optionally a DNA sequence encoding a targeting signal or a transit peptide, all active in said host plant,
(ii) inserting said recombinant 1-SST gene construct of step i) into the genome of a cell of the host plant, and
(iii) regenerating a corresponding transgenic plant from the transformed cell obtained in step ii).

21. The method according to claim 6 wherein said method comprises the subsequent steps of
(i) preparing a recombinant 1-SST gene construct comprising the 1-SST enzyme encoding cDNA sequence according to SEQ ID NO: 1, operably linked to a promoter sequence, a terminator sequence, and optionally a DNA sequence encoding a targeting signal or a transit peptide, all active in said host plant,
(ii) preparing a recombinant 1-FFT gene construct comprising a 1-FFT enzyme encoding DNA sequence from plant origin, operably linked to a promoter sequence, a terminator sequence, and optionally a DNA sequence encoding a targeting signal or a transit peptide, all active in said host plant,
(iii) inserting said 1-SST gene construct of step i) and said 1-FFT gene construct of step ii) into the genome of a cell of the host plant, and
(iv) regenerating a corresponding transgenic plant from the transformed cell obtained in step iii).

22. The method according to claim 21 wherein the recombinant 1-FFT gene construct comprises at least one 1-FFT enzyme encoding c86b cDNA sequence according to SEQ ID NO: 3.

23. The method according to claim 10 wherein said method comprises the subsequent steps of
(i) preparing a recombinant gene construct comprising the enzyme encoding cDNA according to SEQ ID NO: 1, operably linked to a promoter sequence, a terminator sequence, and optionally a DNA sequence encoding a targeting signal or a transit peptide, all active in said host plant,
(ii) inserting said recombinant gene construct of step i) into the genome of a cell of the host plant, and
(iii) regenerating a corresponding transgenic plant from the transformed cell obtained in step ii).

24. The method for producing inulin with a modified inulin profile from source plant material wherein the source material is plant material from a transgenic plant obtained by the method defined in claim 4.

25. A method for producing inulin with a modified inulin profile from source plant material wherein the source material is plant material from a transgenic plant obtained by the method defined in claim 6.

26. The method for producing inulin with a modified inulin profile from source plant material wherein the source material is plant material from a transgenic plant obtained by the method defined in claim 10.

27. A recombinant gene or vector each comprising a combination of a 1-SST enzyme encoding gene comprising the cDNA sequence according to SEQ ID NO: 1, and of a 1-FFT enzyme encoding gene of plant origin, which enzyme encoding genes are respectively operably linked to a promoter sequence and a terminator sequence, and optionally to a DNA sequence encoding a targeting signal or a transit peptide, all active in an host plant.

28. The recombinant gene or vector according to claim 27, wherein the 1-FFT enzyme encoding gene comprises at least one cDNA sequence according to SEQ ID NO: 3.

29. A transgenic plant with a modified inulin producing profile; or a root, shoot, plant part, plant tissue, plant cell thereof or seed thereof, each with a genome according to that of said transgenic plant; comprising in its genome a recombinant 1-SST enzyme encoding gene comprising at least one copy of the cDNA sequence according to SEQ ID NO: 1, operably linked to a promoter sequence and a terminator sequence.

30. A transgenic plant with a modified inulin producing profile; or a root, shoot, plant part, plant tissue, plant cell thereof, each or seed thereof with a genome according to that of said transgenic plant, according to claim 29; comprising in its genome a recombinant 1-SST enzyme encoding gene comprising more than one copy of the cDNA sequence according to SEQ ID NO: 1, operably linked to a promoter sequence and a terminator sequence.

31. A transgenic plant with a modified inulin producing profile; or a root, shoot, plant part, plant tissue, plant cell thereof or seed thereof, each with a genome according to that of said transgenic plant, according to claim 29; comprising in its genome furthermore a 1-FFT enzyme encoding gene operably linked to a promoter sequence and a terminator sequence.

32. A transgenic plant with a modified inulin producing profile; or a root, shoot, plant part, plant tissue, plant cell thereof or seed thereof, each with a genome according to that of said transgenic plant, according to claim 30, comprising in its genome furthermore a 1-FFT enzyme encoding gene operably linked to a promoter sequence and a terminator sequence.

33. A transgenic plant with a modified inulin producing profile; or a root, shoot, plant part, plant tissue, plant cell thereof or seed thereof, each with a genome according to that of said transgenic plant, according to claim 31; comprising in its genome a 1-FFT enzyme encoding gene that comprises at least one copy of the cDNA sequence according to SEQ ID NO: 3.

34. A transgenic plant according to claim 29, which presents an improved tolerance against drought stress or cold stress.

35. A transgenic plant according to claim 30, which presents an improved tolerance against drought stress or cold stress.

36. A transgenic plant according to claim 31, which presents an improved tolerance against drought stress or cold stress.

37. A transgenic plant according to claim 32, which presents an improved tolerance against drought stress or cold stress.

38. A transgenic plant according to claim 33, which presents an improved tolerance against drought stress or cold stress.

* * * * *

SEQUENCE LISTING

<160> NUMBER OF SEQ ID NOS: 6

<210> SEQ ID NO 1
<211> LENGTH: 2008
<212> TYPE: DNA
<213> ORGANISM: Helianthus tuberosus
<220> FEATURE:
<221> NAME/KEY: CDS
<222> LOCATION: (13)..(1857)

<400> SEQUENCE: 1

```
gcaaaaatca cc atg gct tcc acc ccc acc acc cct ctt att act cac aat     51
              Met Ala Ser Thr Pro Thr Thr Pro Leu Ile Thr His Asn
                1               5                  10 gac ctt gaa caa cgc ccg gaa tcg acc gag tct cca ccc ggt cga tca        99
Asp Leu Glu Gln Arg Pro Glu Ser Thr Glu Ser Pro Pro Gly Arg Ser
 15                  20                  25 tcc atc gta aag atc ctc act gga tta ttt gtg tcc att ctt gtt ctt       147
Ser Ile Val Lys Ile Leu Thr Gly Leu Phe Val Ser Ile Leu Val Leu
 30                  35                  40                  45 tca tca ttg gct gca ata aca cac cgg aaa act ccc ttg cag tcc acc       195
Ser Ser Leu Ala Ala Ile Thr His Arg Lys Thr Pro Leu Gln Ser Thr
                 50                  55                  60 aca gtt gat att gaa cca tcg aca agc agt ccg aag gag gtt gtg gga       243
Thr Val Asp Ile Glu Pro Ser Thr Ser Ser Pro Lys Glu Val Val Gly
             65                  70                  75 gcg gat gat agc att gaa tgg caa cga tct gct tac cat ttt caa ccc       291
Ala Asp Asp Ser Ile Glu Trp Gln Arg Ser Ala Tyr His Phe Gln Pro
         80                  85                  90 gat aaa aat ttc att agc gat cct gat ggt cca ctg tat tac aag gga       339
Asp Lys Asn Phe Ile Ser Asp Pro Asp Gly Pro Leu Tyr Tyr Lys Gly
 95                 100                 105 tgg tac cac tta ttc tac caa tac aat ccg ggg tca gcc att tgg ggc       387
Trp Tyr His Leu Phe Tyr Gln Tyr Asn Pro Gly Ser Ala Ile Trp Gly
110                 115                 120                 125 aac ata aca tgg ggt cat gca gtc tcg aaa gac ctc atc aat tgg ttc       435
Asn Ile Thr Trp Gly His Ala Val Ser Lys Asp Leu Ile Asn Trp Phe
                130                 135                 140 cac ctc cct tta gcc atg gtt ccg gat cac tgg tac gac atc cat ggt       483
His Leu Pro Leu Ala Met Val Pro Asp His Trp Tyr Asp Ile His Gly
            145                 150                 155 gtc atg act ggg tcc gcc acc atc ctc ccc aat ggc caa atc ttc atg       531
Val Met Thr Gly Ser Ala Thr Ile Leu Pro Asn Gly Gln Ile Phe Met
        160                 165                 170 ctt tat agc ggc aac gcc tac gac ctc tct cag ctt caa tgc ctc gcg       579
Leu Tyr Ser Gly Asn Ala Tyr Asp Leu Ser Gln Leu Gln Cys Leu Ala
    175                 180                 185 tac ccc aaa aat gct tct gat cca ctt ctt atc gaa tgg gtc aaa tac       627
Tyr Pro Lys Asn Ala Ser Asp Pro Leu Leu Ile Glu Trp Val Lys Tyr
190                 195                 200                 205 gaa ggc aac cca att ctc ttc cct cct ccg ggc gtg ggt ctc aaa gac       675
Glu Gly Asn Pro Ile Leu Phe Pro Pro Pro Gly Val Gly Leu Lys Asp
```

```
                    210                 215                 220
ttt agg gac ccg tca tct ctt tgg att ggg ccc gat ggg aag tac cga    723
Phe Arg Asp Pro Ser Ser Leu Trp Ile Gly Pro Asp Gly Lys Tyr Arg
            225                 230                 235 atg gtt atg ggc tcc aag cac aat aat aca att ggt tgt gct tta att    771
Met Val Met Gly Ser Lys His Asn Asn Thr Ile Gly Cys Ala Leu Ile
        240                 245                 250 tac cac acc act aat ttc acc cat ttt gaa ttg ttg gat gag gtg ctc    819
Tyr His Thr Thr Asn Phe Thr His Phe Glu Leu Leu Asp Glu Val Leu
    255                 260                 265 cat tcg gtt cag ggt acg ggt atg tgg gaa tgt gtt gat ctt tac ccc    867
His Ser Val Gln Gly Thr Gly Met Trp Glu Cys Val Asp Leu Tyr Pro
270                 275                 280                 285 gta tcc acg acc gag aca aac ggg ttg gat atg tcg aat cat gag tcg    915
Val Ser Thr Thr Glu Thr Asn Gly Leu Asp Met Ser Asn His Glu Ser
                290                 295                 300 ggt gct aag tat gtg ttg aag caa agt ggg gat gag gat aga cat gat    963
Gly Ala Lys Tyr Val Leu Lys Gln Ser Gly Asp Glu Asp Arg His Asp
            305                 310                 315 tgg tat gca att ggg gca tat gac gtg gtt cat gat aaa tgg tat ccg    1011
Trp Tyr Ala Ile Gly Ala Tyr Asp Val Val His Asp Lys Trp Tyr Pro
        320                 325                 330 gat gat ccg gaa atg gat ttg ggt atc ggg ttg aga tat gat tat gga    1059
Asp Asp Pro Glu Met Asp Leu Gly Ile Gly Leu Arg Tyr Asp Tyr Gly
    335                 340                 345 aag ttt tat gct tca aag acg ttt tat gac ccg agt aag aag agg cgg    1107
Lys Phe Tyr Ala Ser Lys Thr Phe Tyr Asp Pro Ser Lys Lys Arg Arg
350                 355                 360                 365 gtc tta tgg ggc tat gtt ggt gaa acg gat cct caa aaa gat gac ctc    1155
Val Leu Trp Gly Tyr Val Gly Glu Thr Asp Pro Gln Lys Asp Asp Leu
                370                 375                 380 gag aaa gga tgg gcc aat att ttg aat gtt cct aga acc gtg gtg ttg    1203
Glu Lys Gly Trp Ala Asn Ile Leu Asn Val Pro Arg Thr Val Val Leu
            385                 390                 395 gac acg aag acg caa agt aac ttg att caa tgg ccg gtc gag gaa aca    1251
Asp Thr Lys Thr Gln Ser Asn Leu Ile Gln Trp Pro Val Glu Glu Thr
        400                 405                 410 gaa act ttg aga tct gaa gag tac gat gag ttc aaa gat gtt gag ttg    1299
Glu Thr Leu Arg Ser Glu Glu Tyr Asp Glu Phe Lys Asp Val Glu Leu
    415                 420                 425 cgg cct gga tca ctt gtc ccg ctt gat ata ggc tca gcc aca cag ttg    1347
Arg Pro Gly Ser Leu Val Pro Leu Asp Ile Gly Ser Ala Thr Gln Leu
430                 435                 440                 445 gac ata agt gcc tca ttc gag gtt gat gaa gct ttg ctg ggt gca acc    1395
Asp Ile Ser Ala Ser Phe Glu Val Asp Glu Ala Leu Leu Gly Ala Thr
                450                 455                 460 tta gaa gcc gat gtg ttg ttc aac tgc acc acg agc gag ggt tca gcc    1443
Leu Glu Ala Asp Val Leu Phe Asn Cys Thr Thr Ser Glu Gly Ser Ala
            465                 470                 475 atg agg ggt gtt ttg gga ccg ttt ggg ctt gtg gtt ctt gca gat tcg    1491
Met Arg Gly Val Leu Gly Pro Phe Gly Leu Val Val Leu Ala Asp Ser
        480                 485                 490 gca ctt tca gaa caa act cct gtt tac ttc tac att gcg aaa aac ttg    1539
Ala Leu Ser Glu Gln Thr Pro Val Tyr Phe Tyr Ile Ala Lys Asn Leu
    495                 500                 505 gat ggc act tca aga act tat ttc tgt gct gat gaa tca aga tca tca    1587
Asp Gly Thr Ser Arg Thr Tyr Phe Cys Ala Asp Glu Ser Arg Ser Ser
510                 515                 520                 525 aag ctt tta gat gtg ggc aag atg gta tat gga agc agt gtt cct gta    1635
```

-continued

```
Lys Leu Leu Asp Val Gly Lys Met Val Tyr Gly Ser Ser Val Pro Val
            530                 535                 540 ctc cat ggg gaa aac tac gac atg agg tta ttg gtg gat cat tca ata    1683
Leu His Gly Glu Asn Tyr Asp Met Arg Leu Leu Val Asp His Ser Ile
            545                 550                 555 gtc gaa agc ttt gca caa gga gga aga acg gtg att aca tca aga gtg    1731
Val Glu Ser Phe Ala Gln Gly Gly Arg Thr Val Ile Thr Ser Arg Val
        560                 565                 570 tat cct aca atg gca atc tat gat gcc gcc aaa gtg ttt gtg ttc aac    1779
Tyr Pro Thr Met Ala Ile Tyr Asp Ala Ala Lys Val Phe Val Phe Asn
    575                 580                 585 aat gca act gga atc act gtt aag gca tct ctc aag att tgg aag atg    1827
Asn Ala Thr Gly Ile Thr Val Lys Ala Ser Leu Lys Ile Trp Lys Met
590                 595                 600                 605 ggt gga gca caa ctc aac cct ttt cct ttc taattagttt agttggcttc      1877
Gly Gly Ala Gln Leu Asn Pro Phe Pro Phe
                610                 615 attagttggt gacgttttgg tgaatttgta agcttgttgt agtgagggcg gccttgatga  1937
ttaatattgc cattgtaaaa cttccatttt tttaaaaaaa taatcgattt aaaagttttt  1997
ttaaaaaaaa a                                                       2008

<210> SEQ ID NO 2
<211> LENGTH: 615
<212> TYPE: PRT
<213> ORGANISM: Helianthus tuberosus

<400> SEQUENCE: 2

Met Ala Ser Thr Pro Thr Thr Pro Leu Ile Thr His Asn Asp Leu Glu
 1               5                  10                  15

Gln Arg Pro Glu Ser Thr Glu Ser Pro Pro Gly Arg Ser Ser Ile Val
            20                  25                  30

Lys Ile Leu Thr Gly Leu Phe Val Ser Ile Leu Val Leu Ser Ser Leu
        35                  40                  45

Ala Ala Ile Thr His Arg Lys Thr Pro Leu Gln Ser Thr Thr Val Asp
    50                  55                  60

Ile Glu Pro Ser Thr Ser Ser Pro Lys Glu Val Val Gly Ala Asp Asp
65                  70                  75                  80

Ser Ile Glu Trp Gln Arg Ser Ala Tyr His Phe Gln Pro Asp Lys Asn
                85                  90                  95

Phe Ile Ser Asp Pro Asp Gly Pro Leu Tyr Tyr Lys Gly Trp Tyr His
            100                 105                 110

Leu Phe Tyr Gln Tyr Asn Pro Gly Ser Ala Ile Trp Gly Asn Ile Thr
        115                 120                 125

Trp Gly His Ala Val Ser Lys Asp Leu Ile Asn Trp Phe His Leu Pro
    130                 135                 140

Leu Ala Met Val Pro Asp His Trp Tyr Asp Ile His Gly Val Met Thr
145                 150                 155                 160

Gly Ser Ala Thr Ile Leu Pro Asn Gly Gln Ile Phe Met Leu Tyr Ser
                165                 170                 175

Gly Asn Ala Tyr Asp Leu Ser Gln Leu Gln Cys Leu Ala Tyr Pro Lys
            180                 185                 190

Asn Ala Ser Asp Pro Leu Leu Ile Glu Trp Val Lys Tyr Glu Gly Asn
        195                 200                 205

Pro Ile Leu Phe Pro Pro Pro Gly Val Gly Leu Lys Asp Phe Arg Asp
    210                 215                 220
```

-continued

```
Pro Ser Ser Leu Trp Ile Gly Pro Asp Gly Lys Tyr Arg Met Val Met
225                 230                 235                 240

Gly Ser Lys His Asn Asn Thr Ile Gly Cys Ala Leu Ile Tyr His Thr
            245                 250                 255

Thr Asn Phe Thr His Phe Glu Leu Leu Asp Glu Val Leu His Ser Val
        260                 265                 270

Gln Gly Thr Gly Met Trp Glu Cys Val Asp Leu Tyr Pro Val Ser Thr
    275                 280                 285

Thr Glu Thr Asn Gly Leu Asp Met Ser Asn His Glu Ser Gly Ala Lys
290                 295                 300

Tyr Val Leu Lys Gln Ser Gly Asp Glu Asp Arg His Asp Trp Tyr Ala
305                 310                 315                 320

Ile Gly Ala Tyr Asp Val Val His Asp Lys Trp Tyr Pro Asp Asp Pro
                325                 330                 335

Glu Met Asp Leu Gly Ile Gly Leu Arg Tyr Asp Tyr Gly Lys Phe Tyr
            340                 345                 350

Ala Ser Lys Thr Phe Tyr Asp Pro Ser Lys Lys Arg Arg Val Leu Trp
        355                 360                 365

Gly Tyr Val Gly Glu Thr Asp Pro Gln Lys Asp Asp Leu Glu Lys Gly
    370                 375                 380

Trp Ala Asn Ile Leu Asn Val Pro Arg Thr Val Val Leu Asp Thr Lys
385                 390                 395                 400

Thr Gln Ser Asn Leu Ile Gln Trp Pro Val Glu Glu Thr Glu Thr Leu
                405                 410                 415

Arg Ser Glu Glu Tyr Asp Glu Phe Lys Asp Val Glu Leu Arg Pro Gly
            420                 425                 430

Ser Leu Val Pro Leu Asp Ile Gly Ser Ala Thr Gln Leu Asp Ile Ser
        435                 440                 445

Ala Ser Phe Glu Val Asp Glu Ala Leu Leu Gly Ala Thr Leu Glu Ala
    450                 455                 460

Asp Val Leu Phe Asn Cys Thr Thr Ser Glu Gly Ser Ala Met Arg Gly
465                 470                 475                 480

Val Leu Gly Pro Phe Gly Leu Val Val Leu Ala Asp Ser Ala Leu Ser
                485                 490                 495

Glu Gln Thr Pro Val Tyr Phe Tyr Ile Ala Lys Asn Leu Asp Gly Thr
            500                 505                 510

Ser Arg Thr Tyr Phe Cys Ala Asp Glu Ser Arg Ser Ser Lys Leu Leu
        515                 520                 525

Asp Val Gly Lys Met Val Tyr Gly Ser Ser Val Pro Val Leu His Gly
    530                 535                 540

Glu Asn Tyr Asp Met Arg Leu Leu Val Asp His Ser Ile Val Glu Ser
545                 550                 555                 560

Phe Ala Gln Gly Gly Arg Thr Val Ile Thr Ser Arg Val Tyr Pro Thr
                565                 570                 575

Met Ala Ile Tyr Asp Ala Ala Lys Val Phe Val Phe Asn Asn Ala Thr
            580                 585                 590

Gly Ile Thr Val Lys Ala Ser Leu Lys Ile Trp Lys Met Gly Gly Ala
        595                 600                 605

Gln Leu Asn Pro Phe Pro Phe
    610                 615

<210> SEQ ID NO 3
<211> LENGTH: 1982
<212> TYPE: DNA
```

-continued

```
<213> ORGANISM: Cichorium intybus
<220> FEATURE:
<221> NAME/KEY: CDS
<222> LOCATION: (40)..(1890)

<400> SEQUENCE: 3
tcgcggccgc gtcgacactt ggcccatttc cctcgaaca atg aaa aca gcc gaa        54
                                             Met Lys Thr Ala Glu
                                             1               5 ccc tta agt gac ctt gag gat gca tcc aac cgc act ccc cta cta gac      102
Pro Leu Ser Asp Leu Glu Asp Ala Ser Asn Arg Thr Pro Leu Leu Asp
            10                  15                  20 cac cct gca cca cca ccg gcc gcc gtg aaa aag cag tcg ttc gtc agg      150
His Pro Ala Pro Pro Pro Ala Ala Val Lys Lys Gln Ser Phe Val Arg
        25                  30                  35 gtt ctg tcc agt atc act ttg gtg tct ctg ttc ttc gtt tta gct ttc      198
Val Leu Ser Ser Ile Thr Leu Val Ser Leu Phe Phe Val Leu Ala Phe
    40                  45                  50 gta ctc atc gtc ctg aac cag caa gat tcc acg aac gcc act gcc aat      246
Val Leu Ile Val Leu Asn Gln Gln Asp Ser Thr Asn Ala Thr Ala Asn
55                  60                  65 tta gca ctg ccg gag aaa tct tcg gct caa cac tat cag tcc gat cgc      294
Leu Ala Leu Pro Glu Lys Ser Ser Ala Gln His Tyr Gln Ser Asp Arg
70                  75                  80                  85 ctg aca tgg gaa aga aca gct tac cat ttt cag cca gcc aaa aat ttc      342
Leu Thr Trp Glu Arg Thr Ala Tyr His Phe Gln Pro Ala Lys Asn Phe
                90                  95                 100 atc tac gat ccc aat ggg cca ctg ttc cac atg ggt tgg tac cat ctt      390
Ile Tyr Asp Pro Asn Gly Pro Leu Phe His Met Gly Trp Tyr His Leu
            105                 110                 115 ttc tat caa tac aac ccg tac gct cca att tgg ggc aac atg tca tgg      438
Phe Tyr Gln Tyr Asn Pro Tyr Ala Pro Ile Trp Gly Asn Met Ser Trp
        120                 125                 130 ggt cac gcc gtg tcc aaa gac atg atc aac tgg ttc gag ctt ccc gta      486
Gly His Ala Val Ser Lys Asp Met Ile Asn Trp Phe Glu Leu Pro Val
    135                 140                 145 gcc ttg aca cca acc gag tgg tac gat atc gag ggc gtc tta tcc ggg      534
Ala Leu Thr Pro Thr Glu Trp Tyr Asp Ile Glu Gly Val Leu Ser Gly
150                 155                 160                 165 tcc acc acg gcc ctc ccc aac ggt caa atc ttt gca ttg tac acc gga      582
Ser Thr Thr Ala Leu Pro Asn Gly Gln Ile Phe Ala Leu Tyr Thr Gly
                170                 175                 180 aat gct aat gat ttc tct caa cta caa tgc aaa gct gtt ccg tta aac      630
Asn Ala Asn Asp Phe Ser Gln Leu Gln Cys Lys Ala Val Pro Leu Asn
            185                 190                 195 aca tct gac cca ctc ctt ctc gag tgg gtc aaa tac gag aat aac cca      678
Thr Ser Asp Pro Leu Leu Leu Glu Trp Val Lys Tyr Glu Asn Asn Pro
        200                 205                 210 atc ttg ttc act cca cca ggg att gga tta aaa gac tat cgg gac ccg      726
Ile Leu Phe Thr Pro Pro Gly Ile Gly Leu Lys Asp Tyr Arg Asp Pro
    215                 220                 225 tct aca gtt tgg acg ggt cct gat gga aaa cat cgg atg atc atg ggc      774
Ser Thr Val Trp Thr Gly Pro Asp Gly Lys His Arg Met Ile Met Gly
230                 235                 240                 245 act aaa ata aat cgt act gga ctc gta ctt gtt tac cat act acc gac      822
Thr Lys Ile Asn Arg Thr Gly Leu Val Leu Val Tyr His Thr Thr Asp
                250                 255                 260 ttc aca aac tat gta atg ttg gag gag ccg ttg cat tcg gtt ccc gat      870
Phe Thr Asn Tyr Val Met Leu Glu Glu Pro Leu His Ser Val Pro Asp
            265                 270                 275
```

-continued

| | | |
|---|---|---|
| acc gat atg tgg gaa tgt gtt gac ttg tac cct gtg tca aca att aat<br>Thr Asp Met Trp Glu Cys Val Asp Leu Tyr Pro Val Ser Thr Ile Asn<br>280                        285                  290 | 918 |
| gac agc gca ctt gat atc gcg gct tat ggt ccc gat atg aag cat gtg<br>Asp Ser Ala Leu Asp Ile Ala Ala Tyr Gly Pro Asp Met Lys His Val<br>     295                     300                  305 | 966 |
| att aaa gaa agt tgg gag gga cat ggg atg gac tgg tac tcg att ggg<br>Ile Lys Glu Ser Trp Glu Gly His Gly Met Asp Trp Tyr Ser Ile Gly<br>310                        315                  320                  325 | 1014 |
| aca tat gat gtg ata aac gat aag tgg acc ccg gat aac ccg gaa ttg<br>Thr Tyr Asp Val Ile Asn Asp Lys Trp Thr Pro Asp Asn Pro Glu Leu<br>                    330                  335                  340 | 1062 |
| gac gtg ggt att ggg tta aga gtc gat tac ggg agg ttt ttt gca tca<br>Asp Val Gly Ile Gly Leu Arg Val Asp Tyr Gly Arg Phe Phe Ala Ser<br>345                        350                  355 | 1110 |
| aag agt ctt tat gac ccg ttg aag aaa cgg agg gtc act tgg ggt tat<br>Lys Ser Leu Tyr Asp Pro Leu Lys Lys Arg Arg Val Thr Trp Gly Tyr<br>                  360                  365                  370 | 1158 |
| gtt gca gaa tcg gac agt gcg gac cag gac ctt aat aga ggg tgg gct<br>Val Ala Glu Ser Asp Ser Ala Asp Gln Asp Leu Asn Arg Gly Trp Ala<br>375                        380                  385 | 1206 |
| act att tac aac gtt gca aga acc att gtg cta gat aga aag acc gga<br>Thr Ile Tyr Asn Val Ala Arg Thr Ile Val Leu Asp Arg Lys Thr Gly<br>390                        395                  400                  405 | 1254 |
| acc cat cta ctt cat tgg cct gtt gag gaa att gag agt ttg aga tat<br>Thr His Leu Leu His Trp Pro Val Glu Glu Ile Glu Ser Leu Arg Tyr<br>                    410                  415                  420 | 1302 |
| gat ggt cgt gaa ttt aaa gag atc gag ctt gca ccg gtt cg atc atg<br>Asp Gly Arg Glu Phe Lys Glu Ile Glu Leu Ala Pro Gly Ser Ile Met<br>425                        430                  435 | 1350 |
| cca ctc gac ata ggc ccg gct acg cag ttg gac ata gtt gcc aca ttt<br>Pro Leu Asp Ile Gly Pro Ala Thr Gln Leu Asp Ile Val Ala Thr Phe<br>                    440                  445                  450 | 1398 |
| gag gtg gaa caa gag acg ttt atg agg aca agt gac aca aat ggt gaa<br>Glu Val Glu Gln Glu Thr Phe Met Arg Thr Ser Asp Thr Asn Gly Glu<br>455                        460                  465 | 1446 |
| tac ggt tgc acc acg agc gcg ggt gca acc gaa agg gga agt ttg gga<br>Tyr Gly Cys Thr Thr Ser Ala Gly Ala Thr Glu Arg Gly Ser Leu Gly<br>470                        475                  480                  485 | 1494 |
| ccg ttt ggg atc gcg gtt ctt gct gat gga aca ctc tcg gaa tta act<br>Pro Phe Gly Ile Ala Val Leu Ala Asp Gly Thr Leu Ser Glu Leu Thr<br>                    490                  495                  500 | 1542 |
| cct gtg tat ttc tat att tct aaa aag aca gat gga agc gtt gca aca<br>Pro Val Tyr Phe Tyr Ile Ser Lys Lys Thr Asp Gly Ser Val Ala Thr<br>505                        510                  515 | 1590 |
| cat ttt tgt acc gat aag cta agg tca tca ctg gat tat gac ggg gag<br>His Phe Cys Thr Asp Lys Leu Arg Ser Ser Leu Asp Tyr Asp Gly Glu<br>     520                     525                  530 | 1638 |
| aga gtg gta tac ggg agc act gtc cct gta ctc gat ggt gaa gaa ctc<br>Arg Val Val Tyr Gly Ser Thr Val Pro Val Leu Asp Gly Glu Glu Leu<br>535                        540                  545 | 1686 |
| aca atg agg tta ctg gtg gat cat tca gta gtg gag ggg ttt gca atg<br>Thr Met Arg Leu Leu Val Asp His Ser Val Val Glu Gly Phe Ala Met<br>550                        555                  560                  565 | 1734 |
| gga gga agg aca gta atg aca tca cga gtg tat ccc aca aag gca ata<br>Gly Gly Arg Thr Val Met Thr Ser Arg Val Tyr Pro Thr Lys Ala Ile<br>                    570                  575                  580 | 1782 |
| tat gaa gga gcc aag atc ttc ttg ttc aac aat gcg act cat acc agt<br>Tyr Glu Gly Ala Lys Ile Phe Leu Phe Asn Asn Ala Thr His Thr Ser<br>585                        590                  595 | 1830 |

-continued

```
gtg aag gca tct ctc aag atc tgg caa ata gct tct gta cga atc cag     1878
Val Lys Ala Ser Leu Lys Ile Trp Gln Ile Ala Ser Val Arg Ile Gln
            600                 605                 610 cct tac cct ttt tagttatttc gtttcatgaa catgctcttt tattatatat          1930
Pro Tyr Pro Phe
    615 attcatgtat tttattttcc ttctaggtaa aaaaaaaaaa aaaaaaaaaa aa            1982
```

<210> SEQ ID NO 4
<211> LENGTH: 617
<212> TYPE: PRT
<213> ORGANISM: Cichorium intybus

<400> SEQUENCE: 4

```
Met Lys Thr Ala Glu Pro Leu Ser Asp Leu Glu Asp Ala Ser Asn Arg
  1               5                  10                  15

Thr Pro Leu Leu Asp His Pro Ala Pro Pro Ala Ala Val Lys Lys
             20                  25                  30

Gln Ser Phe Val Arg Val Leu Ser Ser Ile Thr Leu Val Ser Leu Phe
         35                  40                  45

Phe Val Leu Ala Phe Val Leu Ile Val Leu Asn Gln Gln Asp Ser Thr
     50                  55                  60

Asn Ala Thr Ala Asn Leu Ala Leu Pro Glu Lys Ser Ser Ala Gln His
 65                  70                  75                  80

Tyr Gln Ser Asp Arg Leu Thr Trp Glu Arg Thr Ala Tyr His Phe Gln
                 85                  90                  95

Pro Ala Lys Asn Phe Ile Tyr Asp Pro Asn Gly Pro Leu Phe His Met
            100                 105                 110

Gly Trp Tyr His Leu Phe Tyr Gln Tyr Asn Pro Tyr Ala Pro Ile Trp
        115                 120                 125

Gly Asn Met Ser Trp Gly His Ala Val Ser Lys Asp Met Ile Asn Trp
    130                 135                 140

Phe Glu Leu Pro Val Ala Leu Thr Pro Thr Glu Trp Tyr Asp Ile Glu
145                 150                 155                 160

Gly Val Leu Ser Gly Ser Thr Thr Ala Leu Pro Asn Gly Gln Ile Phe
                165                 170                 175

Ala Leu Tyr Thr Gly Asn Ala Asn Asp Phe Ser Gln Leu Gln Cys Lys
            180                 185                 190

Ala Val Pro Leu Asn Thr Ser Pro Leu Leu Glu Trp Val Lys
        195                 200                 205

Tyr Glu Asn Asn Pro Ile Leu Phe Thr Pro Gly Ile Gly Leu Lys
    210                 215                 220

Asp Tyr Arg Asp Pro Ser Thr Val Trp Thr Gly Pro Asp Gly Lys His
225                 230                 235                 240

Arg Met Ile Met Gly Thr Lys Ile Asn Arg Thr Gly Leu Val Leu Val
                245                 250                 255

Tyr His Thr Thr Asp Phe Thr Asn Tyr Val Met Leu Glu Glu Pro Leu
            260                 265                 270

His Ser Val Pro Asp Thr Asp Met Trp Glu Cys Val Asp Leu Tyr Pro
        275                 280                 285

Val Ser Thr Ile Asn Asp Ser Ala Leu Asp Ile Ala Ala Tyr Gly Pro
    290                 295                 300

Asp Met Lys His Val Ile Lys Glu Ser Trp Glu Gly His Gly Met Asp
305                 310                 315                 320
```

```
Trp Tyr Ser Ile Gly Thr Tyr Asp Val Ile Asn Asp Lys Trp Thr Pro
            325                 330                 335

Asp Asn Pro Glu Leu Asp Val Gly Ile Gly Leu Arg Val Asp Tyr Gly
            340                 345                 350

Arg Phe Phe Ala Ser Lys Ser Leu Tyr Asp Pro Leu Lys Lys Arg Arg
            355                 360                 365

Val Thr Trp Gly Tyr Val Ala Glu Ser Asp Ser Ala Asp Gln Asp Leu
    370                 375                 380

Asn Arg Gly Trp Ala Thr Ile Tyr Asn Val Ala Arg Thr Ile Val Leu
385                 390                 395                 400

Asp Arg Lys Thr Gly Thr His Leu Leu His Trp Pro Val Glu Glu Ile
            405                 410                 415

Glu Ser Leu Arg Tyr Asp Gly Arg Glu Phe Lys Glu Ile Glu Leu Ala
            420                 425                 430

Pro Gly Ser Ile Met Pro Leu Asp Ile Gly Pro Ala Thr Gln Leu Asp
            435                 440                 445

Ile Val Ala Thr Phe Glu Val Glu Gln Glu Thr Phe Met Arg Thr Ser
    450                 455                 460

Asp Thr Asn Gly Glu Tyr Gly Cys Thr Thr Ser Ala Gly Ala Thr Glu
465                 470                 475                 480

Arg Gly Ser Leu Gly Pro Phe Gly Ile Ala Val Leu Ala Asp Gly Thr
            485                 490                 495

Leu Ser Glu Leu Thr Pro Val Tyr Phe Tyr Ile Ser Lys Lys Thr Asp
            500                 505                 510

Gly Ser Val Ala Thr His Phe Cys Thr Asp Lys Leu Arg Ser Ser Leu
            515                 520                 525

Asp Tyr Asp Gly Glu Arg Val Val Tyr Gly Ser Thr Val Pro Val Leu
    530                 535                 540

Asp Gly Glu Glu Leu Thr Met Arg Leu Leu Val Asp His Ser Val Val
545                 550                 555                 560

Glu Gly Phe Ala Met Gly Gly Arg Thr Val Met Thr Ser Arg Val Tyr
            565                 570                 575

Pro Thr Lys Ala Ile Tyr Glu Gly Ala Lys Ile Phe Leu Phe Asn Asn
            580                 585                 590

Ala Thr His Thr Ser Val Lys Ala Ser Leu Lys Ile Trp Gln Ile Ala
            595                 600                 605

Ser Val Arg Ile Gln Pro Tyr Pro Phe
    610                 615

<210> SEQ ID NO 5
<211> LENGTH: 2157
<212> TYPE: DNA
<213> ORGANISM: Cichorium intybus
<220> FEATURE:
<221> NAME/KEY: CDS
<222> LOCATION: (22)..(1941)

<400> SEQUENCE: 5
cgcggccgcg tcgaccccca c atg gct tcc tct acc acc gcc acc acc cct       51
                        Met Ala Ser Ser Thr Thr Ala Thr Thr Pro
                          1               5                  10 ctc atc ctc cgt gat gag act caa atc agc cca caa cta gct gga tct       99
Leu Ile Leu Arg Asp Glu Thr Gln Ile Ser Pro Gln Leu Ala Gly Ser
                15                  20                  25 ccg gtg ggt cgg cgt tta tcc atg gcc aat atc ctt tcc ggg atc ctc      147
Pro Val Gly Arg Arg Leu Ser Met Ala Asn Ile Leu Ser Gly Ile Leu
        30                  35                  40
```

-continued

| | | |
|---|---|---|
| gtt ttc gtc ctt gtc atc tgt gtt ctg gtt gct gtt atc cac gac caa<br>Val Phe Val Leu Val Ile Cys Val Leu Val Ala Val Ile His Asp Gln<br>              45                    50                    55 | | 195 |
| tca caa caa aca atg gcg acc aac aac cat cag gga gaa gat aaa ccc<br>Ser Gln Gln Thr Met Ala Thr Asn Asn His Gln Gly Glu Asp Lys Pro<br>   60                        65                        70 | | 243 |
| acc tcc gcc gcc acg ttc aca gct ccg ttg cta caa gtt gat ctc aaa<br>Thr Ser Ala Ala Thr Phe Thr Ala Pro Leu Leu Gln Val Asp Leu Lys<br>75                    80                    85                    90 | | 291 |
| cgg gtt ccc gga aag ttg gaa tcc aat gct gat gtt gag tgg caa cgc<br>Arg Val Pro Gly Lys Leu Glu Ser Asn Ala Asp Val Glu Trp Gln Arg<br>              95                    100                 105 | | 339 |
| tca gct tac cat ttt caa ccc gat aag aat ttc atc agc gat cct gat<br>Ser Ala Tyr His Phe Gln Pro Asp Lys Asn Phe Ile Ser Asp Pro Asp<br>        110                        115                 120 | | 387 |
| ggt cca atg tat cac atg ggg tgg tac cat ctc ttc tac cag tac aac<br>Gly Pro Met Tyr His Met Gly Trp Tyr His Leu Phe Tyr Gln Tyr Asn<br>           125                      130                 135 | | 435 |
| cca gaa tca gcc ata tgg ggc aac atc aca tgg ggc cac tcc gta tca<br>Pro Glu Ser Ala Ile Trp Gly Asn Ile Thr Trp Gly His Ser Val Ser<br>    140                        145                 150 | | 483 |
| cga gac atg atc aac tgg ttc cat ctc cca ttc gcc atg gtc ccg gac<br>Arg Asp Met Ile Asn Trp Phe His Leu Pro Phe Ala Met Val Pro Asp<br>155                    160                    165                 170 | | 531 |
| cat tgg tac gac atc gaa ggg gtc atg acc gga tcc gcc acg gta ctc<br>His Trp Tyr Asp Ile Glu Gly Val Met Thr Gly Ser Ala Thr Val Leu<br>                175                      180                 185 | | 579 |
| ccc aac ggt cag atc atc atg ctc tac act ggc aac gcg tac gat ctc<br>Pro Asn Gly Gln Ile Ile Met Leu Tyr Thr Gly Asn Ala Tyr Asp Leu<br>                    190                      195                 200 | | 627 |
| tcc cag tta cag tgc tta gca tac gcc gtc aac tca tct gat cct ctc<br>Ser Gln Leu Gln Cys Leu Ala Tyr Ala Val Asn Ser Ser Asp Pro Leu<br>        205                        210                 215 | | 675 |
| ctt ctg gaa tgg aaa aag tac gaa gga aac cca att ttg ttc cca ccg<br>Leu Leu Glu Trp Lys Lys Tyr Glu Gly Asn Pro Ile Leu Phe Pro Pro<br>        220                        225                 230 | | 723 |
| cct ggt gtg gga tac aaa gat ttt cga gat cca tcc aca tta tgg atg<br>Pro Gly Val Gly Tyr Lys Asp Phe Arg Asp Pro Ser Thr Leu Trp Met<br>235                    240                    245                 250 | | 771 |
| ggt cct gat ggg gaa tgg aga atg gta atg ggg tcc aaa cac aat gaa<br>Gly Pro Asp Gly Glu Trp Arg Met Val Met Gly Ser Lys His Asn Glu<br>                255                      260                 265 | | 819 |
| act att ggt tgt gca ttg gtc tac cgt act act aat ttt acg cat ttt<br>Thr Ile Gly Cys Ala Leu Val Tyr Arg Thr Thr Asn Phe Thr His Phe<br>                    270                      275                 280 | | 867 |
| gaa ctg aat gag gag gta ctc cac gca gtc ccc cat act ggt atg tgg<br>Glu Leu Asn Glu Glu Val Leu His Ala Val Pro His Thr Gly Met Trp<br>        285                        290                 295 | | 915 |
| gaa tgt gtg gac cta tac cct gtg tcc acc acg cac acg aat ggg ttg<br>Glu Cys Val Asp Leu Tyr Pro Val Ser Thr Thr His Thr Asn Gly Leu<br>300                    305                    310 | | 963 |
| gac atg aag gat aat ggg ccg aat gtt aaa tat att ttg aaa caa agt<br>Asp Met Lys Asp Asn Gly Pro Asn Val Lys Tyr Ile Leu Lys Gln Ser<br>315                    320                    325                 330 | | 1011 |
| gga gac gaa gac cga cat gat tgg tat gcg gtt ggg act ttt gac cct<br>Gly Asp Glu Asp Arg His Asp Trp Tyr Ala Val Gly Thr Phe Asp Pro<br>                    335                      340                 345 | | 1059 |
| gag aaa gat aag tgg tac cct gac gac cct gaa aac gat gtg gga atc<br>Glu Lys Asp Lys Trp Tyr Pro Asp Asp Pro Glu Asn Asp Val Gly Ile | | 1107 |

```
                350                 355                 360
ggg ttg aga tac gac tac gga aag ttc tat gcg tca aag aca ttt tat      1155
Gly Leu Arg Tyr Asp Tyr Gly Lys Phe Tyr Ala Ser Lys Thr Phe Tyr
        365                 370                 375 gat caa cat gaa aag cgg agg gta ctt tgg ggt tat gtt ggt gaa acc      1203
Asp Gln His Glu Lys Arg Arg Val Leu Trp Gly Tyr Val Gly Glu Thr
        380                 385                 390 gac ccc cct aag tcc gat ctt tta aag gga tgg gct aac atc ttg aat      1251
Asp Pro Pro Lys Ser Asp Leu Leu Lys Gly Trp Ala Asn Ile Leu Asn
395                 400                 405                 410 atc cca agg tcc gtt gtt ttg gac acg caa acc gga acc aat ttg att      1299
Ile Pro Arg Ser Val Val Leu Asp Thr Gln Thr Gly Thr Asn Leu Ile
                415                 420                 425 caa tgg ccg att gat gaa gtg gaa aaa ttg aga tca aca aaa tat gac      1347
Gln Trp Pro Ile Asp Glu Val Glu Lys Leu Arg Ser Thr Lys Tyr Asp
        430                 435                 440 gaa ttc aaa gac gtg gag ctc cga ccc gga tca ctc gtt ccc ctc gaa      1395
Glu Phe Lys Asp Val Glu Leu Arg Pro Gly Ser Leu Val Pro Leu Glu
        445                 450                 455 att ggc aca gcg aca cag ttg gac ata agt gcg aca ttt gaa atc gat      1443
Ile Gly Thr Ala Thr Gln Leu Asp Ile Ser Ala Thr Phe Glu Ile Asp
        460                 465                 470 caa aag aag tta caa tca acg ctt gaa gcc gat gtt ttg ttc aac tgt      1491
Gln Lys Lys Leu Gln Ser Thr Leu Glu Ala Asp Val Leu Phe Asn Cys
475                 480                 485                 490 aca act agc gaa ggt tca gtc cgg aag ggt gtg ttg gga cca ttt gga      1539
Thr Thr Ser Glu Gly Ser Val Arg Lys Gly Val Leu Gly Pro Phe Gly
                495                 500                 505 atc gtg gtt cta gcg gat gcc aac cgc tct gag caa ctt cct gtg tat      1587
Ile Val Val Leu Ala Asp Ala Asn Arg Ser Glu Gln Leu Pro Val Tyr
        510                 515                 520 ttc tat att gcc aaa gac acc gat gga acc tca aaa act tac ttc tgt      1635
Phe Tyr Ile Ala Lys Asp Thr Asp Gly Thr Ser Lys Thr Tyr Phe Cys
        525                 530                 535 gct gat gaa tca agg tca tcg acg gac aaa tac gtt gga aaa tgg gta      1683
Ala Asp Glu Ser Arg Ser Ser Thr Asp Lys Tyr Val Gly Lys Trp Val
        540                 545                 550 tac gga agc agt gtt cct gtt ctt gaa ggt gaa aat tac aac atg agg      1731
Tyr Gly Ser Ser Val Pro Val Leu Glu Gly Glu Asn Tyr Asn Met Arg
555                 560                 565                 570 tta ctg gtg gat cat tcg ata gtg gaa ggg ttc gca caa gga gga aga      1779
Leu Leu Val Asp His Ser Ile Val Glu Gly Phe Ala Gln Gly Gly Arg
                575                 580                 585 acg gtg gtg aca tca aga gtg tac ccc acg aag gcc atc tat ggc gct      1827
Thr Val Val Thr Ser Arg Val Tyr Pro Thr Lys Ala Ile Tyr Gly Ala
        590                 595                 600 gct aag ata ttt ttg ttc aac aac gcc acc gga att agc gtc aag gca      1875
Ala Lys Ile Phe Leu Phe Asn Asn Ala Thr Gly Ile Ser Val Lys Ala
        605                 610                 615 tct ctc aag atc tgg aaa atg gcg gaa gca caa ctc gat cca ttc cct      1923
Ser Leu Lys Ile Trp Lys Met Ala Glu Ala Gln Leu Asp Pro Phe Pro
        620                 625                 630 ctt tct ggg tgg agt tct tgattattag aattcgtcat ccctctctat             1971
Leu Ser Gly Trp Ser Ser
635                 640 ttgtgtgtta tgttgtgaa atatggtagc atgattgcgg gtttagtggg ggtattatgg     2031
tagtttgtta atggtggttg tggtactgca tttgtgagat tataaattga attgttattc    2091
ctgtttacaa cttttctaag caaatggtat gtcatgtttt gatcaaaaaa aaaaaaaaa     2151
``` aaaaaa                                                                                                    2157

<210> SEQ ID NO 6
<211> LENGTH: 640
<212> TYPE: PRT
<213> ORGANISM: Cichorium intybus

<400> SEQUENCE: 6

```
Met Ala Ser Ser Thr Ala Thr Thr Pro Leu Ile Leu Arg Asp Glu
  1               5                  10                  15

Thr Gln Ile Ser Pro Gln Leu Ala Gly Ser Pro Val Gly Arg Arg Leu
                 20                  25                  30

Ser Met Ala Asn Ile Leu Ser Gly Ile Leu Val Phe Val Leu Val Ile
             35                  40                  45

Cys Val Leu Val Ala Val Ile His Asp Gln Ser Gln Gln Thr Met Ala
         50                  55                  60

Thr Asn His Gln Gly Glu Asp Lys Pro Thr Ser Ala Ala Thr Phe
 65                  70                  75                  80

Thr Ala Pro Leu Leu Gln Val Asp Leu Lys Arg Val Pro Gly Lys Leu
                 85                  90                  95

Glu Ser Asn Ala Asp Val Glu Trp Gln Arg Ser Ala Tyr His Phe Gln
                100                 105                 110

Pro Asp Lys Asn Phe Ile Ser Asp Pro Asp Gly Pro Met Tyr His Met
                115                 120                 125

Gly Trp Tyr His Leu Phe Tyr Gln Tyr Asn Pro Glu Ser Ala Ile Trp
            130                 135                 140

Gly Asn Ile Thr Trp Gly His Ser Val Ser Arg Asp Met Ile Asn Trp
145                 150                 155                 160

Phe His Leu Pro Phe Ala Met Val Pro Asp His Trp Tyr Asp Ile Glu
                165                 170                 175

Gly Val Met Thr Gly Ser Ala Thr Val Leu Pro Asn Gly Gln Ile Ile
                180                 185                 190

Met Leu Tyr Thr Gly Asn Ala Tyr Asp Leu Ser Gln Leu Gln Cys Leu
            195                 200                 205

Ala Tyr Ala Val Asn Ser Ser Asp Pro Leu Leu Leu Glu Trp Lys Lys
        210                 215                 220

Tyr Glu Gly Asn Pro Ile Leu Phe Pro Pro Gly Val Gly Tyr Lys
225                 230                 235                 240

Asp Phe Arg Asp Pro Ser Thr Leu Trp Met Gly Pro Asp Gly Glu Trp
                245                 250                 255

Arg Met Val Met Gly Ser Lys His Asn Glu Thr Ile Gly Cys Ala Leu
            260                 265                 270

Val Tyr Arg Thr Thr Asn Phe Thr His Phe Glu Leu Asn Glu Glu Val
        275                 280                 285

Leu His Ala Val Pro His Thr Gly Met Trp Glu Cys Val Asp Leu Tyr
    290                 295                 300

Pro Val Ser Thr Thr His Thr Asn Gly Leu Asp Met Lys Asp Asn Gly
305                 310                 315                 320

Pro Asn Val Lys Tyr Ile Leu Lys Gln Ser Gly Asp Glu Asp Arg His
                325                 330                 335

Asp Trp Tyr Ala Val Gly Thr Phe Asp Pro Glu Lys Asp Lys Trp Tyr
            340                 345                 350

Pro Asp Asp Pro Glu Asn Asp Val Gly Ile Gly Leu Arg Tyr Asp Tyr
        355                 360                 365
```

-continued

```
Gly Lys Phe Tyr Ala Ser Lys Thr Phe Tyr Asp Gln His Glu Lys Arg
        370                 375                 380

Arg Val Leu Trp Gly Tyr Val Gly Glu Thr Asp Pro Pro Lys Ser Asp
385                 390                 395                 400

Leu Leu Lys Gly Trp Ala Asn Ile Leu Asn Ile Pro Arg Ser Val Val
                405                 410                 415

Leu Asp Thr Gln Thr Gly Thr Asn Leu Ile Gln Trp Pro Ile Asp Glu
                420                 425                 430

Val Glu Lys Leu Arg Ser Thr Lys Tyr Asp Glu Phe Lys Asp Val Glu
            435                 440                 445

Leu Arg Pro Gly Ser Leu Val Pro Leu Glu Ile Gly Thr Ala Thr Gln
        450                 455                 460

Leu Asp Ile Ser Ala Thr Phe Glu Ile Asp Gln Lys Lys Leu Gln Ser
465                 470                 475                 480

Thr Leu Glu Ala Asp Val Leu Phe Asn Cys Thr Thr Ser Glu Gly Ser
                485                 490                 495

Val Arg Lys Gly Val Leu Gly Pro Phe Gly Ile Val Val Leu Ala Asp
                500                 505                 510

Ala Asn Arg Ser Glu Gln Leu Pro Val Tyr Phe Tyr Ile Ala Lys Asp
            515                 520                 525

Thr Asp Gly Thr Ser Lys Thr Tyr Phe Cys Ala Asp Glu Ser Arg Ser
        530                 535                 540

Ser Thr Asp Lys Tyr Val Gly Lys Trp Val Tyr Gly Ser Ser Val Pro
545                 550                 555                 560

Val Leu Glu Gly Glu Asn Tyr Asn Met Arg Leu Leu Val Asp His Ser
                565                 570                 575

Ile Val Glu Gly Phe Ala Gln Gly Gly Arg Thr Val Val Thr Ser Arg
                580                 585                 590

Val Tyr Pro Thr Lys Ala Ile Tyr Gly Ala Ala Lys Ile Phe Leu Phe
            595                 600                 605

Asn Asn Ala Thr Gly Ile Ser Val Lys Ala Ser Leu Lys Ile Trp Lys
        610                 615                 620

Met Ala Glu Ala Gln Leu Asp Pro Phe Pro Leu Ser Gly Trp Ser Ser
625                 630                 635                 640
```